United States Patent
Harrington et al.

(10) Patent No.: US 7,767,454 B2
(45) Date of Patent: Aug. 3, 2010

(54) METHODS FOR MUTATING GENES IN CELLS USING INSERTIONAL MUTAGENESIS

(75) Inventors: John Joseph Harrington, Mentor, OH (US); Paul David Jackson, Shaker Heights, OH (US); Li Jiang, Hudson, OH (US)

(73) Assignee: ABT Holding Company, Cleveland, OH (US)

( * ) Notice: Subject to any disclaimer, the term of this patent is extended or adjusted under 35 U.S.C. 154(b) by 609 days.

(21) Appl. No.: 10/288,555

(22) Filed: Nov. 4, 2002

(65) Prior Publication Data

US 2003/0134421 A1 Jul. 17, 2003

Related U.S. Application Data

(60) Provisional application No. 60/330,978, filed on Nov. 2, 2001.

(51) Int. Cl.
C12N 15/00 (2006.01)
(52) U.S. Cl. ...................................... 435/455; 435/440
(58) Field of Classification Search ........................ None
See application file for complete search history.

(56) References Cited

U.S. PATENT DOCUMENTS

| | | | |
|---|---|---|---|
| 5,487,992 A | 1/1996 | Capecchi et al. | |
| 5,843,742 A | 12/1998 | Natsoulis et al. | |
| 5,994,503 A | 11/1999 | Xu et al. | |
| 6,136,566 A * | 10/2000 | Sands et al. | 435/69.7 |
| 6,361,972 B1 | 3/2002 | Harrington et al. | |
| 6,410,266 B1 | 6/2002 | Harrington et al. | |
| 2003/0224519 A1 | 12/2003 | Harrington et al. | |
| 2004/0018624 A1 | 1/2004 | Harrington et al. | |

FOREIGN PATENT DOCUMENTS

| | | |
|---|---|---|
| WO | WO 93/23534 | 11/1993 |
| WO | WO 99/15650 | 4/1999 |
| WO | WO 00/36088 | 6/2000 |
| WO | WO 00/73510 A1 | 12/2000 |

OTHER PUBLICATIONS

Mullin and Mullin. Clinical invest. 1996, vol. 97, No. 7, pp. 1557-1559.*
Campell and Wilmut. Theriogenology, 1997. vol. 47, pp. 63-72.*
Bradley et al. Biotechnology, 1992, vol. 10. pp. 534-539.*
NIH report 2000 Stem Cell: scientific progress and future research directions. Chapter 2: The embryonic stem cell.*
Amsterdam et al., "A large-scale insertional mutagenesis screen in zebrafish." *Genes Dev.* Oct. 15, 1999;13(20):2713-24.
Brown et al. "Bypass of senescence after disruption of p21$^{CIP1/WAF1}$ gene in normal diploid human fibroblasts." *Science.* Aug. 8, 1997;277(5327):831-4.
Cui et al. "Structure-function analysis of the inverted terminal repeats of the *sleeping beauty* transposon." *J Mol Biol.* May 17, 2002;318(5):1221-35.
Friedrich et al. "Insertional mutagenesis by retroviruses and promoter traps in embryonic stem cells." *Methods Enzymol.* 1993;225:681-701.
Friedrich et al. "Promoter traps in embryonic stem cells: a genetic screen to identify and mutate developmental genes in mice." *Genes Dev.* Sep. 1991;5(9):1513-23.
Gogos et al. "Selection for retroviral insertions into regulated genes." *J Virol.* Feb. 1997;71(2):1644-50.
Lefebvre "Selection for transgene homozygosity in embryonic stem cells results in extensive loss of heterozygosity." *Nat Genet.* Mar. 2001;27(3):257-8.

(Continued)

*Primary Examiner*—Anne-Marie Falk
(74) *Attorney, Agent, or Firm*—Thompson Hine LLP

(57) ABSTRACT

The present invention is in the fields of molecular biology, cell biology, and genetics. The invention is directed generally to mutating genes in cells in vitro and in multi-cellular organisms. The invention encompasses methods for mutating genes in cells using polynucleotides that act as insertional mutagens. Such methods are used to achieve mutation of a single gene to achieve a desired phenotype as well as mutation of multiple genes, required cumulatively to achieve a desired phenotype, in a cell or in a multi-cellular organism. The invention is also directed to methods of identifying one or more mutated genes, made by the methods of the invention, in cells and in multi-cellular organisms, by means of a tagging property provided by the insertional mutagen(s). The insertional mutagen thus allows identification of one or more genes that are mutated by insertion of an insertional mutagen. The invention is also directed to methods for correlating a phenotype with a gene by screening or selecting cells that have been mutated by an insertional mutagen incorporated into one or more genes in a cell and identifying the gene or genes causing the phenotype by means of a tagging property in one or more of the insertional mutagens.

Figure 1A:
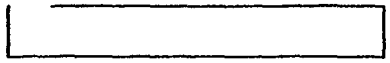
Figure 1B:
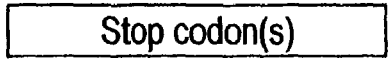
Figure 1C:
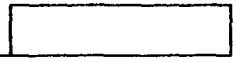
Figure 1D:
Figure 1E:
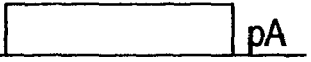
Figure 1F:
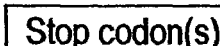
Figure 1G:
Figure 1H:
Figure 1I:
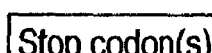
Figure 1J:
Figure 2A:
Figure 2B:
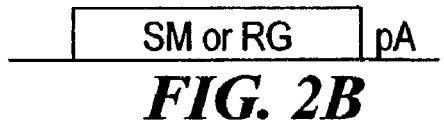
Figure 2C:
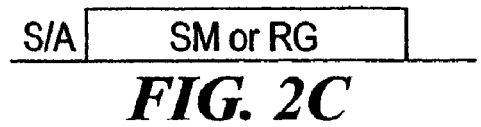
Figure 2D:
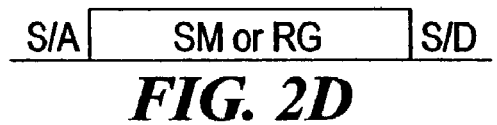
Figure 2E:
Figure 2F:
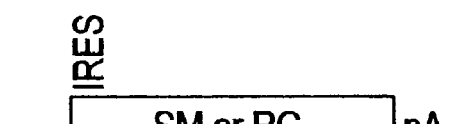
Figure 2G:
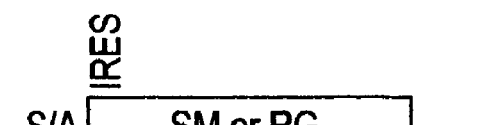
Figure 2H:

The invention is also directed to cells and multi-cellular organisms created by the methods of the invention and uses of the cells and multicellular organisms. The invention is also directed to libraries of cells created by the methods of the invention and uses of the libraries.

17 Claims, 17 Drawing Sheets

OTHER PUBLICATIONS

Mansour et al. "Introduction of a *lacZ* reporter gene into the mouse *int-2* locus by homologous recombination." *PNAS USA*. Oct. 1990;87(19):7688-92.

Milstone et al. "Simultaneous Cre catalyzed recombination of two alleles to restore neomycin sensitivity and facilitate homozygous mutations." *Nucleic Acids Res*. Aug. 1, 1999;27(15):e10i-e10iii.

Mortensen et al. "Production of homozygous mutant ES cells with a single targeting construct." *Mol Cell Biol*. May 1992;12(5):2391-5.

te Riele et al. "Consecutive inactivation of both alleles of the *pim-1* proto-oncogene by homologous recombination in embryonic stem cells." *Nature* 1990 13;348(6302):649-51.

Varmus et al. "Retroviruses as mutagens: insertion and excision of a nontransforming provirus alter expression of a resident transforming provirus." *Cell*. Jul. 1981;25(1):23-36.

von Melchner et al. "Selective disruption of genes expressed in totipotent embryonal stem cells." *Genes Dev*. 1992;6:919-927.

Voss et al. "Efficiency assessment of the gene trap approach." *Dev Dyn*. Jun. 1998;212(2):171-80.

Yue et al. "Genetic analysis of viable Hsp90 alleles reveals a critical role in *Drosophila spermatogenesis*." *Genetics*. Mar. 1999;151(3):1065-79.

Zambrowicz et al. "Disruption of overlapping transcripts in the ROSA βgeo 26 gene trap strain leads to widespread expression of β-galactosidase in mouse embryos and hematopoietic cells." *PNAS USA*. Apr. 15, 1997;94(8):3789-94.

Berns, A. "Tumorigenesis in transgenic mice: identification and characterization of synergizing oncogenes." *J Cell Biochem*. Oct. 1991; 47(2):130-5.

Klinakis, A. G. et al. "Genome-wide insertional mutagenesis in human cells by the *Drosophila* mobile element *Minos*" *EMBO Reports*, vol. 1, No. 51, pp. 416-421 (2000).

Vilen et al., "Construction of gene-targeting vectors: a rapid Mu in vitro DNA transposition-based strategy generating null, potentially hypomorphic, and conditional alleles" Transgenic Research 10:69-80 (2001).

\* cited by examiner

| S/A | SM or RG | pA |

FIG. 3A

| S/A | IRES SM or RG | pA |

FIG. 3B

(A)

I II (B)

I

II III

IV (D)

I

II

III

IV

METHODS FOR MUTATING GENES IN CELLS USING INSERTIONAL MUTAGENESIS

CROSS-REFERENCE TO RELATED APPLICATIONS

The present application claims the benefit of U.S. Provisional Application No. 60/330,978 filed Nov. 2, 2001, the entire disclosure of which is incorporated herein by reference.

STATEMENT REGARDING FEDERALLY-SPONSORED RESEARCH AND DEVELOPMENT

Not applicable.

REFERENCE TO MICROFICHE APPENDIX/SEQUENCE LISTING/TABLE/COMPUTER PROGRAM LISTING APPENDIX

Not applicable.

BACKGROUND OF THE INVENTION

1. Field of the Invention

The present invention is in the fields of molecular biology, cell biology, and genetics. The invention is directed generally to mutating genes in cells in vitro and in multi-cellular organisms. The invention encompasses methods for mutating genes in cells using polynucleotides that act as insertional mutagens. Such methods are used to achieve mutation of a single gene to achieve a desired phenotype as well as mutation of multiple genes, required cumulatively to achieve a desired phenotype, in a cell or in a multi-cellular organism. The invention is also directed to methods of identifying one or more mutated genes, made by the methods of the invention, in cells and in multi-cellular organisms, by means of a tagging property provided by the insertional mutagen(s). The insertional mutagen thus allows identification of one or more genes that are mutated by insertion of an insertional mutagen. The invention is also directed to methods for correlating a phenotype with a gene by screening cells that have been mutated by an insertional mutagen incorporated into one or more genes in a cell and identifying the gene or genes causing the phenotype by means of a tagging property in one or more of the insertional mutagens.

The invention is also directed to cells and multi-cellular organisms created by the methods of the invention and uses of the cells and multicellular organisms. The invention is also directed to libraries of cells created by the methods of the invention and uses of the libraries.

2. Background

Mutagenesis has been used to identify the function of a large and growing number of genes. Mutation of one or more genes in a multi-cellular organism or cell allows the artisan to study the mutant organism or cell and compare it to the non-mutagenized (which may be wildtype) parent organism or cell. By identifying phenotypes associated with the mutant organism or cell, the function of the mutated gene(s) can be ascertained. Furthermore, mutagenesis provides a means for altering the genetic make up of a cell or multi-cellular organism to obtain a desired result. For example, it may be desirable to create a physiological disorder in a eukaryotic organism by mutating one more genes and then to identify one or more of the relevant genes. Thus, mutations that have a desired use (e.g., for commercial production of proteins, foodstuffs, or pharmaceuticals, or for production of transgenic animals as models of certain diseases) can be identified and selected. The possibilities for use of this technology, whether in vitro, ex vivo, or in vivo, are well known in the art.

Identification of novel genes and characterization of their function using mutagenesis has also been shown to be productive in identifying new drugs and drug targets Creating in vitro cellular models that exhibit phenotypes that are clinically relevant provides a valuable substrate for target identification and screening for compounds that modulate not only the phenotype but also the target(s) that controls the phenotype. Modulation of such a target can provide information that validates the target as important for therapeutic intervention in a clinical disorder when such modulation of the target serves to modulate a clinically relevant phenotype.

Animal models exhibiting clinically relevant phenotypes are also valuable for drug discovery and development and for drug target identification. For example, mutation of somatic or germ cells facilitates the production of genetically modified offspring or cloned animals having a phenotype of interest. Such animals have a number of uses, for example as models of physiological disorders (e.g., of human genetic diseases) that are useful for screening the efficacy of candidate therapeutic compounds or compositions for treating or preventing such physiological disorders. Furthermore, identifying the gene(s) responsible for the phenotype provides potential drug targets for modulating the phenotype and, when the phenotype is clinically relevant, for therapeutic intervention. In addition, the manipulation of the genetic makeup of organisms and the identification of new genes have important uses in agriculture, for example in the development of new strains of animals and plants having higher nutritional value or increased resistance to environmental stresses (such as heat, drought, or pests) relative to their wildtype or non-mutant counterparts.

Since most eukaryotic cells are diploid, two copies of most genes are present in each cell. As a consequence, homozygous mutation is usually required to produce a desired phenotype, since mutating only one copy of a gene may not produce a sufficient change in the level of gene expression or activity of the gene product from that in the non-mutated or wildtype cell or multicellular organism, and since the remaining wildtype copy would still be expressed at sufficient levels to produce a functional gene product. Thus, to create a desired change in the level of gene expression and/or function in a cell or multicellular organism, at least two mutations, one in each copy of the gene, are required in the same cell.

In other instances, mutations in multiple genes are required to produce a desired phenotype. Phenotypes have been reported to result from trans-heterozygous mutations in which a single allele of each of two or more distinct genes are mutated (Yue L, *Genetics*. March 1999; 151(3):1065-79. Aubin J, *Dev Dyn*. May 1998; 212(1):141-56. Fedorowicz G M, *Genetics*. April 1998; 148(4):1885-91. Price J V, *Genetics*. November 1997; 147(3):1139-53. Ruden D M, *Dev Biol*. Nov. 15, 1997; 191(2):284-96. White-Cooper H, *Genetics*. November 1996; 144(3):1097-111).

In some instances, a mutation in one copy of a gene may affect the expression levels of the gene but not the activity of the gene product to a desired extent, so that the desired physiological effects on the cell or multi-cellular organism is not achieved. However, a mutation in a second gene, even in only one copy of that second gene, can reduce gene expression levels of the second gene to produce a cumulative phenotypic effect in combination with the first mutation, if the expression levels of both genes are sufficiently low. This effect can alter the function of a cell or multi-cellular organism. An example of this phenomenon is the synergy between blood clotting Factors VIII and IX. A mutation in either gene alone could result in levels that are severely reduced but with no effect on the clotting function. Severe reductions in the level of expression of both genes, however, can have a major impact. This principle can be extended to other instances where mutations in multiple (two, three, four, or more, for example) genes are required cumulatively to produce an effect on activity of a gene product or on another phenotype in a cell or multi-cellular organism. It should be noted that, in this instance, such genes may all be expressed in the same cell type and therefore, all of the required mutations occur in the same cell. However, the genes may normally be expressed in different cell types (for example, secreting the different gene products from the different cells). In this case, the gene products are expressed in different cells but still have a biochemical relationship such that one or more mutations in each gene is required to produce the desired phenotype.

Unfortunately, few methods exist for creating cultured cells that contain multiple gene mutations that produce, cumulatively, a desired phenotype. Such methods often are time-consuming and prone to error. In addition, it is often very difficult or impossible to identify the genes that have been mutated using such methods.

Further, methods for making homozygous mutations in cultured cells followed by identification of the mutations that cause phenotypes are not known to currently exist where the mutated genes are not known in advance of mutation. Without a way to identify a homozygous mutation, the artisan cannot associate the phenotype with a given mutation. Currently, to associate a desired phenotype with a homozygous mutation in a cultured cell, the location, structure and/or function of the gene must be known to the artisan in advance. Hence, the methods of mutation known in the art are not suitable for homozygously mutating a cell to achieve a desired phenotype and identifying the gene(s) responsible for the phenotype. Nor are there methods suitable for making cells with multiple mutations that cumulatively produce a desired phenotype and identifying the genes responsible for the phenotype.

Several approaches for introducing mutations into eukaryotic genes are currently in use. Each has significant limitations.

One approach is homologous recombination to mutate the level of gene expression or activity of a gene product in a cell. 1: Montgomery et al., *Cell*. Feb. 22, 1991; 64(4):693-702; 2: te Riele et al. *Nature*. Dec. 13, 1990; 348(6302):649-51; 3: Mansour et. al., *Proc Natl Acad Sci USA*. October 1990; 87(19):7688-92; 4: Koller et al., *Proc Natl Acad Sci USA*. November 1989; 86(22):8927-31; 5: Capecchi M R. *Science*. Jun. 16, 1989; 244(4910):1288-92; 6: Zimmer A, Gruss P. *Nature*. Mar. 9, 1989; 338(6211):150-3; 7: Joyner A L, Skarnes W C, Rossant J. *Nature*. Mar. 9, 1989; 338(6211):153-6; 8: Thompson S, et al. *Cell*. Jan. 27,1989; 56(2):313-21; 9: Doetschman T, Maeda N, Smithies O. *Proc Natl Acad Sci USA*. November 1988; 85(22):8583-7; 10: Doetschman T, et al. *Nature*. 1987 Dec. 10-16; 330(6148):576-8; 11: Thomas K R, Capecchi M R. *Cell*. Nov. 6, 1987; 51(3):503-12.

Typically, this approach is taken in embryonic stem cells or embryonic germ cells, which are then used to make transgenic animals carrying the mutation of interest. An important limitation of this approach is that the gene to be mutated must be known in advance of mutation, cloned and sequenced to ensure that the mutagenic vector used in homologous recombination contains the appropriate targeting sequences. Furthermore, the process is laborious and results in only one mutant copy of the gene of interest in the cell. Where a phenotype depends on homozygosity for expression, the heterozygous cell, therefore, cannot be used to screen for a change in a phenotype of interest unless additional work is carried out to eliminate the second copy of the gene by homologous recombination (Brown, J. P. et al, *Science*, 277: 831-834 (1997)) or by homozygosis of the mutant chromosome (e.g., Mortensen, R. M. et al., *Mol. Cell. Biol.*, 12:2391-2395 (1992)) Milstone D S, *Nucleic Acids Res*. Aug. 1, 1999; 27(15):e10. Lefebvre L, *Nat Genet*. March 2001; 27(3):257-8). This additional work is time consuming and expensive, and more importantly can only be done on genes that are known to the artisan in advance.

Such mutated heterozygous cells can be used to make transgenic animals. However, such animals will also be heterozygous and may not express a phenotype different from the wildtype or non-mutant animal. Further breeding of the animals to homozygosity is therefore required if one desires to analyze the phenotypic effect of the mutation. Such breeding is time consuming and expensive.

Another approach involves chemical mutagenesis of cells and/or organisms (see, e.g., Brown et al., *Hum. Mol. Genet.* 7:1627-1633 (1998); Chen et al., *Nature Gen.* 24:314-317 (2000); Munroe et al., *Nature Gen.* 24:318-321 (2000); Nolan et al., *Nature Gen.* 25:440-443 (2000); the disclosures of all of which are incorporated herein by reference in their entireties for teaching the use of ENU to generate mutations that result in detectable phenotypes in cells or animals). This approach relies upon the use of one or more chemical mutagens that are able to produce one or more mutations in the genome. As is the case for mutation by homologous recombination, however, chemical mutagenesis also typically results in mutagenesis of only a single copy of a given gene. Since in cases where homozygous mutation is required to achieve a desired phenotype, both copies of a given gene must be mutated before a desired phenotype can be achieved, cells or organisms that undergo a single round of chemical mutagenesis typically do not show a desired change in phenotype. Hence, these cells or organisms generally are not useful for achieving for a desired phenotype.

A further problem is that while chemical mutagenesis results in the mutation of one or more genes in a cell, there is no straightforward way to determine the mutated gene(s) responsible for the phenotype. This approach also fails to provide a method for making multiple mutations that cumulatively provide a desired phenotype that also permits the genes responsible for the phenotype to be easily identified.

As discussed above (for homologous recombination mutagenesis) mutated heterozygous cells prepared by chemical mutagenesis can be used to create transgenic animals. However, the animals will also be heterozygous and may not, therefore, manifest a change in a desired phenotype from the wildtype. Time-consuming and costly breeding of the animals to homozygosity is required. Even if a change in the desired phenotype is observed in the transgenic animals (even in homozygous transgenic animals), it is very difficult, if not impossible, to identify the mutated gene(s) responsible for the phenotype. Therefore, a large number of breedings must be carried out to clone the mutated gene by standard positional cloning methods. Hence, this process is slow, expensive, difficult to carry out on large numbers of mutant animals, and has a high failure rate. Thus, chemical mutagenesis fails to provide homozygous mutations in cultured cells (and hence, in transgenic animals produced from such cells) and fails to provide a simple way to identify the mutated gene(s) responsible for a phenotype in cultured cells or in multi-cellular organisms.

Another approach that has been used to mutate genes involves the use of insertional mutagens, such as gene trap vectors, to mutate genes (e.g., Amsterdam et al., *Genes Dev.* 13:2713-2724 (1999); von Melcher et al., *Genes Dev.* 6:919-927 (1992); Gogos et al., *J. Virol.* 71:1644-1650 (1997); Voss et al., *Dev. Dyn.* 212:171-180 (1998); Zambrowicz et al., *Proc. Natl. Acad. Sci. USA* 94:3789-3794 (1997); Friedrich et al., *Genes Dev.* 5:1513-1523 (1991); the disclosures of all of which are incorporated herein by reference in their entireties for teaching the use of gene traps as a mutagenesis technique). These vectors are typically inserted into the genome of a cell by non-homologous recombination. Upon insertion, these vectors are designed to disrupt transcription and/or translation of a gene. Unfortunately, gene trap vectors and other insertional mutagens are inefficient mutagens and have been used to mutate only one copy of a given gene. As a result, it is believed that homozygous mutations cannot be created in cell culture with such mutagens. In animals, the mutant animal must be bred to homozygosity of the mutant gene prior to phenotypic analysis. Since it is difficult and expensive to breed large numbers of animals to homozygosity, this approach has only been used on a relatively small number of genes to date.

This approach also fails to provide a method for making multiple mutations that cumulatively provide a desired phenotype and where the genes responsible for the phenotype can be identified. The probabilities of achieving, in a single cell, insertions in each of the genes required, is low and decreases with the number of genes required to be mutated in order to achieve the desired phenotype. Thus, gene traps and other insertional mutagens have failed to mutate multiple genes and failed to efficiently create homozygous mutations in cultured cells.

Accordingly, there exists a need in the art to create homozygous gene mutations on a genome-wide basis in cell culture and in multicellular organisms without knowledge of the gene in advance and to provide a way to identify the mutated gene. There is also a need for a method of mutating multiple genes in a cell, required cumulatively to achieve a desired phenotype and to identify one or more of the mutated genes. There is also a need to provide these mutations in a workable number of cells and to be able to select cells having mutations so as to reduce the background of cells not having mutations that produce a phenotype. The ability to mutate multiple genes or to mutate both copies of the same gene in cultured cells or multi-cellular organisms, coupled with the ability to identify the mutant gene(s) would be a highly useful approach to identify novel genes, correlate genes with functions, and use the mutant genes, their wildtype counterparts, and other variants, for example, in drug screening and development, transgenic animal and plant production and in the production of desirable gene products.

Copending U.S. application Ser. No. 10/277,612, entitled Compositions and Methods for Making Mutations in Cell Lines and Animals, filed Oct. 22, 2002, based on U.S. provisional application No. 60/336,491, filed Oct. 22, 2001, discloses a combination of insertional mutagenesis and physicochemical mutagenesis that can be used to create homozygous gene mutations on a genome-wide basis in cell culture and in multi-cellular organisms, methods for mutating multiple genes in a cell required cumulatively to achieve a desired phenotype and where the methods provide for the identification of one or more mutated alleles or genes. However, the mutation methods described to achieve those goals involve a combination of insertional mutagenesis and physicochemical mutagenesis. The present invention, on the other hand, achieves these goals using insertional mutagenesis alone, and accordingly, the methods do not involve physicochemical mutagenesis and the compositions are not produced using physicochemical mutagenesis. Using insertional mutagenesis alone is advantageous because any mutation can be identified by means of the insertional mutagen.

The present invention provides a solution to the needs identified above by providing methods of efficiently mutating multiple genes in the same cell and tagging at least one of the mutated genes in cells that contain the mutated multiple genes, so that the identity of one or more of the mutated genes can be achieved. The present invention also provides methods of making homozygous gene mutations and tagging the mutated gene. The present invention also provides a way to reduce background by providing a means to select for cells that have an insertion, and especially an insertion in an active gene.

BRIEF SUMMARY OF THE INVENTION

Accordingly, the present invention is generally directed to methods for creating mutated cells and multicellular organisms using two or more polynucleotides that act as insertional mutagens. The polynucleotide can be used as a tag to identify the cell containing the tag and/or the mutated gene and/or to identify the mutated gene itself. One aspect of the invention encompasses methods for mutating multiple genes that cumulatively produce a desired phenotype, within the same cell, and tagging at least one of the mutated genes. Another aspect of the invention encompasses methods of creating one or more homozygous mutations in a cell that sufficiently alter the mutated gene function to generate a desired phenotype and that tag one or both of the mutated alleles.

Thus, the present invention utilizes insertional mutagenesis to achieve multiple mutations (that cumulatively produce a desired phenotype) within a cell, such that at least one of the mutated genes in each cell containing the multiple mutations can be identified by means of the insertion. In the case of homozygous mutations, at least one of the mutated alleles of the gene can be identified by means of the insertion.

Two or more insertional mutagens are inserted into the genome of the cell or organism in such a manner as to alter the expression of a functional gene product (e.g., an RNA or protein) of one or more cellular genes. At least one of the two or more inserted mutagens also has the property of "tagging" the insertionally mutated gene, thereby allowing it to be identified. By carrying out two insertional mutagenesis events, a cell is created in which one or more genes have been mutated by the insertional mutagens. In one such embodiment of the invention, a cell is created in which both alleles of a given gene have been mutated by the insertions, thereby creating cells that carry homozygous mutations in that gene. Such mutations can produce desired phenotypes. The mutant cell can be screened or selected for the production of desired phenotypes and the tag can be used to identify the gene responsible for the phenotype.

Using this mutational approach, cells are also provided that contain mutations in more than one gene which cumulatively act to produce a desired phenotype. At least one of the mutated genes that contributes to causing the phenotype is tagged by an insertional mutagen so that it can be identified. Taking a simple case in which two genes are required to be mutated, the invention includes, but is not limited to, the following scenarios (1) Gene #1 is mutated by a first insertional mutagenesis event and Gene #2 is mutated by a second insertional mutagenesis event in a first cell. Gene #2 is tagged for identification. (2) Gene #1 is mutated by a first insertional mutagenesis event and Gene #2 is mutated by a second insertional mutagenesis event in a second cell. Gene #1 is tagged for identification. Both cells exhibit the desired phenotype, which is caused by the mutation of two genes cumulatively. In the first cell, Gene #2 is identified by the tag. In the second cell, Gene #1 is identified by the tag. These two cells, however, provide complete information about the identity of the genes that must be mutated to achieve the desired phenotype. It is also possible to tag both genes in both cells, thereby allowing both genes to be identified in either cell or from both cells.

The two mutational events can be carried out in either order, or simultaneously. The mutational events can also be repeated, such that a given cell, population of cells or organism can be subjected to insertional mutagenesis one or more (e.g., two, three, four, five, six, seven, eight, nine, ten, fifteen, twenty, etc.) times, in any order or simultaneously.

Accordingly, the present invention is directed to a method for making a cell that has a homozygous mutation in an endogenous gene by integrating a first insertional mutagen into the genome of a cell to mutate one allele of the endogenous gene and also integrating a second insertional mutagen into the genome of the cell to mutate the second allele of the gene.

In one embodiment, the mutagens are introduced simultaneously. Alternatively, the mutagens can be introduced sequentially.

In one embodiment, the first mutagen is identical to the second mutagen. Alternatively, the two mutagens are not identical.

In one embodiment, the cell is in vitro. Alternatively, the cell is in vivo. In another embodiment one mutagen is introduced in vitro and one is introduced in vivo.

In one embodiment, one or both insertional mutagens is incorporated by non-homologous recombination.

Where the mutagens are introduced sequentially, cells can be screened or selected for incorporation of a mutagen after any or all exposures to a mutagen. Cells having the incorporated mutagen can be isolated and/or cloned.

The cell exposed to the mutagen can be screened or selected for mutation of a specific desired gene or for any other desired phenotype produced in a cell or in an animal. When the mutagens are introduced sequentially, screening or selection can be performed after exposure to any or all of the mutagens. Cells having the mutation or phenotype can be isolated and/or cloned.

When the mutagens are introduced sequentially, the mutated cell can be isolated and cloned after any of the mutagens is incorporated. In one embodiment, the cell is cloned after insertion of the first insertional mutagen. In another embodiment the cell is cloned after insertion of the second insertional mutagen. In another embodiment, the cell is cloned after both the first and second insertional mutagenesis events.

Screening or selection for mutation of a desired gene or phenotype can also be carried out after screening or selection for incorporation of a mutagen. Likewise, screening or selection for incorporation of a mutagen can also be carried out after screening or selection for a phenotype or mutation of a desired gene. These screens or selections can be on isolated and/or cloned cells or on a library.

The mutated gene can be isolated or identified from cells that are identified as having a desired phenotype or from cells that are identified as containing one or both of the insertional mutagens.

Cells can be selected or screened that contain a desired phenotype and/or that contain one or both of the insertional mutagens. Accordingly, selection or screening can be carried out after the first insertional mutagen is introduced, after the second insertional mutagen is introduced, or after each of the insertional mutagens is introduced. Thus the mutagens provide a way to eliminate cells that do not contain an incorporated mutagen.

Cells identified as containing one or more insertional mutagens can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens integrated into an endogenous gene (i.e., cells containing a gene trap event) can be isolated and cloned.

Cells identified as having a specific mutated gene or a desired phenotype can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

The invention is also directed to methods for making a cell that contains a mutation in two or more genes that are cumulatively required to produce a phenotype in the cell or in an animal, the method comprising integrating at least one insertional mutagen into at least one allele of each of the two or more genes.

In one embodiment, the mutagens are introduced simultaneously. Alternatively, the mutagens can be introduced sequentially.

In one embodiment, the mutagens are identical. Alternatively, two or more of the mutagens are different.

In one embodiment, the cell is in vitro. Alternatively, the cell is in vivo.

In one embodiment, one or more of the insertional mutagens is incorporated by non-homologous recombination.

The mutated cell can be screened or selected for mutation of a specific desired gene or for any other desired phenotype produced in a cell or in an animal. When the mutagens are introduced sequentially, screening or selection can be after incorporation of one or more of the insertional mutagens.

The mutated cell can be isolated and cloned. When the mutagens are introduced sequentially, the mutated cell can be isolated and cloned after one or more of the mutagens is introduced.

The mutated gene can be isolated or identified from cells that are identified as having a desired phenotype or from cells that are identified as containing all the required insertional events.

Cells can be selected or screened that contain a desired phenotype and/or that contain one or more of the insertional mutagens. Accordingly, selection can be carried out after one or more of the insertional mutagens is introduced.

Cells identified as containing one or more insertional mutagens can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens integrated into an endogenous gene (i.e., cells containing a gene trap event) can be isolated and cloned.

Cells identified as having a specific mutated gene or a desired phenotype can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

Screening or selection for mutation of a desired gene or phenotype can also be carried out after screening or selection for incorporation or a mutagen. Likewise, screening or selection for incorporation of a mutagen can also be carried out after screening or selection for a phenotype or mutation of a desired gene. These screens or selections can be on isolated and/or cloned cells or on a library.

The invention accordingly is also directed to cells that are produced by any of the methods of the invention.

The invention is directed to a cell comprising at least two different insertional mutagens integrated into its genome by non-homologous recombination. Optionally, one or more of the insertional mutagens lacks targeting sequences.

The invention is directed to a cell comprising a gene with a homozygous mutation, the mutation resulting from the integration of an insertional mutagen into both alleles of the gene. It is understood that the mutation in each allele is achieved by the incorporation of an insertional mutagen independently into each allele. Thus the homozygous mutation results from independent insertion events.

In one embodiment, the insertional mutagen in the first allele is identical to the insertional mutagen in the second allele. Alternatively, the insertional mutagens in each allele are different.

In one embodiment, the cell is in vitro. Alternatively, the cell can be in vivo.

In one embodiment, one or both of the insertional mutagenesis events occurs by incorporation of the insertional mutagen by non-homologous recombination.

Cells identified as containing one or more insertional mutagens can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens integrated into an endogenous gene (i.e., cells containing a gene trap event) can be isolated and cloned.

Cells identified as having a specific mutated gene or a desired phenotype can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

The invention is also directed to a cell containing an insertional mutation in two or more genes, wherein the two or more genes each are mutated by incorporation of an insertional mutagen, and wherein the mutations in the two or more genes are required cumulatively to produce a phenotype in the cell or in a multi-cellular organism.

In one embodiment, the mutagens are identical. Alternatively, two or more of the mutagens are different.

In one embodiment, the cell is in vitro. Alternatively, the cell is in vivo.

In one embodiment, one or more insertional mutagens is incorporated by non-homologous recombination.

The mutated cell can be screened or selected for mutation a specific desired gene or for any other desired phenotype produced in the cell or in an animal. When the mutagens are introduced sequentially, screening or selection can be after incorporation of one or more of the insertional mutagens.

The mutated cell can be isolated and/or cloned. When the mutagens are introduced sequentially, the mutated cell can be isolated and cloned after one or more of the mutagens is introduced.

Cells identified as containing one or more insertional mutagens can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens integrated into an endogenous gene (i.e., cells containing a gene trap event) can be isolated and cloned.

Cells identified as having a specific mutated gene or a desired phenotype can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

The invention is directed to methods for making a library of cells containing two or more mutated endogenous genes by introducing a single insertional mutagen into cells under conditions in which multiple integrations of the insertional mutagen can occur in a cell. In one embodiment the library contains a sufficient number of clones so that both alleles of an endogenous gene are mutated in a single cell and/or multiple genes are mutated in a single cell wherein the multiple mutations are required cumulatively to produce a desired phenotype.

The invention is directed to methods for making libraries of cells by subjecting a plurality of cells to insertional mutagenesis such that at least one cell in the library contains a homozygous mutation of a gene caused by insertional mutagenesis in each of both alleles of the gene.

In one embodiment the mutation is the result of mutagens that are introduced to the plurality of cells simultaneously. Alternatively, the mutagens can be introduced sequentially.

When the mutagens are introduced sequentially, cells can be screened or selected for having a desired phenotype after any insertion event.

Cells can also be screened or selected for having an insertional mutagen incorporated after any insertion event. Cells can be selected or screened on the basis of one or both of these two features and can be used for further insertional mutagenesis events or for identifying the mutated gene(s).

In one embodiment the mutagen in the first allele is identical to the mutagen in the second allele. Alternatively, the two mutagens can be different.

In one embodiment one or more of the insertional mutagens is incorporated by non-homologous recombination.

After one or more insertional mutagenesis events, a cell can be isolated and cloned. This cell can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens integrated into an endogenous gene (i.e., cells containing a gene trap event) can be isolated and cloned.

Cells identified as having a specific mutated gene or a desired phenotype can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

In a preferred embodiment, a library is produced in which there is a mutation in one allele of every gene that requires a homozygous mutation in order to manifest a phenotype. These cells are then exposed to an insertional mutagen, different from the inserted insertional mutagens, such that one gene per cell is mutated and the library comprises sufficient cells so that all of the second alleles of the genes are mutated.

The invention is directed to methods for making libraries of mutated cells by subjecting a plurality of cells to insertional mutagens such that at least two cells in the library contain two or more mutations, the mutations being cumulatively required to produce a phenotype.

In one embodiment, the mutagens are identical. Alternatively, two or more of the mutagens are different.

In one embodiment, one or more insertional mutagens is incorporated by non-homologous recombination.

In one embodiment the mutation is the result of mutagens that are introduced to the plurality of cells simultaneously. Alternatively, the mutagens can be introduced sequentially. When the mutagens are introduced sequentially, cells can be screened or selected for having a desired phenotype after any insertion event.

Cells can also be screened or selected for having an insertional mutagen incorporated after any insertion event. Cells can be selected or screened on the basis of one or both of these two features and can be used for further insertional mutagenesis events or for identifying the mutated gene(s).

In one embodiment one or more of the insertional mutagens is incorporated by non-homologous recombination.

After one or more insertional mutagenesis events, a cell can be isolated and cloned. This cell can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

Cells identified as containing one or more insertional mutagens integrated into an endogenous gene (i.e., cells containing a gene trap event) can be isolated and cloned.

Cells identified as having a specific mutated gene or a desired phenotype can be isolated and cloned. Cells then can be used as a substrate for further mutagenesis events, analyzed for a desired phenotype or expression of a specific desired gene, analyzed for the presence of an insertional mutagen, or used to identify a gene that is mutated by insertion of an insertional mutagen.

In preferred embodiments, a library is produced where there is an insertion in every gene of a gene set except one gene per set, where all mutations in a set are required cumulatively to produce a phenotype. These cells are then subjected to an insertional mutagen, different from the previous insertional mutagen(s), such that an insertional mutation occurs in a sufficient number of cells so that the one insertional mutation mutates the gene required to complete the set of mutated genes cumulatively required to produce a phenotype.

The invention is also directed to a method for making a library of cells containing two or more mutated endogenous genes by integrating a first insertional mutagen into the genome of a plurality of cells by non-homologous recombination, selection or screening cells for integration of the first insertional mutagen into a transcriptionally active gene, and integrating a second insertional mutagen into the genome of the cells containing the first insertional mutagen, thereby producing a library of cells comprising two or more insertional mutagens. Optionally, selection or screening can be carried out for cells containing the second insertional mutagen integrated into a transcriptionally active gene.

The first and second insertional mutagens can be introduced into the cell simultaneously or sequentially.

The first and second insertional mutagens can be identical or can be different from one another.

The method can be carried out on one or more cells in vitro or in vivo.

Cells can be screened for mutation of a desired gene or for another desired phenotype. Cells containing an incorporated insertional mutagen or mutated in a desired gene or displaying a desired phenotype can be isolated and/or cloned.

One or more mutated genes can be identified or isolated from cells containing the insertional mutagen or displaying a desired phenotype. Cells containing an insertional mutagen of interest, displaying a phenotype of interest, or mutated in a desired gene, can be used to produce a multicellular organism, such as a transgenic animal, or can be transferred into an animal by adoptive transfer.

The invention is also directed to libraries of cells made by the methods of the invention.

Libraries comprise a plurality of clones, two or more of the clones having at least two genes mutated in the genome of the cells.

Libraries can also encompass a plurality of clones, each clone having at least one insertional mutagen incorporated into its genome and where at least one clone contains a homozygous mutation produced as a result of an insertional mutagen incorporating into both alleles of a gene.

A library can also encompass a plurality of clones, two or more of the clones containing an insertional mutagen incorporated into the genome of the cells, where at least one clone contains a mutation in two or more genes, the mutations required cumulatively to produce a phenotype in a cell or in an animal.

In a preferred embodiment, two or more clones in the library contain two insertional mutations from mutagens integrated into the genome such that two alleles of the same endogenous gene are mutated to produce a phenotype. In other preferred embodiments, the library contains at least two or more clones having insertional mutagens integrated into the genome of the cell such that two or more genes are mutated, wherein the mutations are cumulatively required to produce a phenotype in a cell or in an animal. In further preferred embodiments, there are ten such clones. In highly preferred embodiments there are 100 such clones.

The population of cells used to produce the library can all be the same (as in a cell line), or can comprise different subpopulations (as, for example, in cell populations prepared from tissues). Each clone in such libraries may contain a set of mutated genes that is distinct from the set of mutated genes in other clones within the library. Alternatively, the same genes may be mutated in different clones but the type of mutation of each gene could be different. For example, all three genes, Genes #1, #2, and #3, could be mutated in three different clones but the type of polynucleotide used for insertional mutation could differ. Such libraries of cells therefore, are useful to rapidly screen or select for desired phenotypes (e.g., changes from the wildtype or nonmutant phenotype) that result from various single mutations or various combinations of mutations.

A library can also encompass a population (two or more, preferably $10^2$-$10^5$) of clones that has been subjected to a first insertional mutagenesis event but not a second. These libraries serve as a population of cells that form a substrate for further mutation by the second mutagenic process of the invention.

The invention also provides methods of using the cells and libraries to screen or select for phenotypes that are created by the mutagenesis methods of the invention and to identify one or more mutations responsible for the phenotype.

In one embodiment, mutated cells are clonally expanded. Optionally the cells may be isolated. Clonal expansion (and isolation) can be following any or all mutation events and can precede or follow any screening or selection step (e.g. via selectable or screenable marker or other phenotype) or further mutagenesis steps.

Accordingly, an object of the invention is to provide a library of cells wherein one or more of the cells is "primed" by insertional mutagenesis events. In such a "primed" cell, a homologous mutation is achieved by subjecting the cell to additional insertional mutagenesis so that one or more insertions occur in the non-mutated allele. In preferred embodiments, when the cells are "primed", cells contain multiple mutations so that genome-wide mutation of every gene in one allele is achieved. The event in which the second allele is mutated preferably is the result of few insertions per cell, for example, 1-5. The gene that is mutated can then be more easily identified by means of the insertional mutagen in the second allele. Accordingly, the priming event can create multiple insertions, for example 1-100.

In such a "primed" cell, mutation of a set of genes can be achieved where a mutation in each of the genes in the set is required in order for a phenotype to be produced. This can be done by subjecting the primed cell, having mutations in less than the complete set, to additional insertional mutagenesis so that one or more insertions occur in the non-mutated members of the set. Accordingly, a plurality of cells is exposed to an insertional mutagen to produce multiple insertions in the cells. As described above, the "priming" event will preferably involve multiple mutations per cell so that the library contains cells in which there are mutations in all genes that form a set of genes that is cumulatively required to produce a desired phenotype, with the proviso that for every one of these sets, at least one gene of the set remains unmutated. Then, an additional insertional mutagenesis is performed on these cells so that the non-mutated genes in each of the sets becomes mutated so that the phenotype can manifest. This event is preferably characterized by relatively few insertions per cell, for example 1-5, so that the mutated gene can be more easily identified by means of the insertional mutagen that mutates the remaining gene.

The insertional mutagen can be the same or different insertional mutagens. Mutagenesis can be simultaneous or sequential. Cells can be selected or screened for presence of the insertional mutagen after any or all of the insertional mutagen exposures. Further, cells can be selected or screened for any phenotype after any and all exposures.

The number of insertions may be greater than the number of gene mutations since, in many organisms, much of the genome does not contain gene sequences. Therefore, in the "priming" step the goal is to achieve a number of insertions that would lead to mutations in a desired number of genes.

In one embodiment, the "primed" cell may contain very few mutations, e.g. 1-10. This cell can then be expanded and the expanded cells subjected to further insertional mutagenesis to mutate a desired gene or achieve a desired phenotype. The further mutagenesis event can be achieved by introducing multiple insertions into the cells or one or less insertions per cell. It is understood that when multiple insertions are made, the number of cells that must be screened for mutation of a desired gene or for a desired phenotype would be less than the number that must be screened when one or less insertion per cell is made. One example is a cell in which one allele of a gene is mutated by a vector containing a targeting sequence, e.g., by homologous recombination. This cell is expanded and the progeny are subjected to further insertional mutagenesis by non-homologous recombination to produce a cell with a mutation in the second allele of the gene. In the case of a trans-heterozygous mutation, a cell can contain a mutation in one gene of the set and the cell can then be expanded and subjected to further insertional mutagenesis to produce a cell with mutations in each gene in the set.

The cells can also be used to produce a transgenic animal or otherwise introduced into an animal, such as by adoptive transfer.

The invention is directed to methods for making a multicellular organism containing a cell that is homozygous for mutation in an endogenous gene by integrating a first insertional mutagen into the genome of the cell to mutate one allele of the endogenous gene and integrating a second insertional mutagen into the genome of the cell containing the first insertional mutagen to mutate the second allele of the gene and producing a transgenic organism from the mutated cell.

The invention is also directed to methods for making an organism containing a cell containing two or more mutations in an endogenous gene by integrating an insertional mutagen into the two or more genes and producing a transgenic organism from the mutated cell.

In one embodiment, the first mutagen is identical to the second mutagen. Alternatively, the two mutagens are different.

In one embodiment, one or both of the insertional mutagens is incorporated by non-homologous recombination.

In one embodiment, the cell is screened or selected for mutation of a specific desired gene or other desired phenotype prior to producing the transgenic organism. Alternatively, the organism can be screened or selected for mutation of a specific desired gene or phenotype.

In one embodiment, one or both alleles of the homozygous mutation are mutated in vitro. Alternatively, one or both are mutated in vivo.

In the embodiment wherein the cell contains two or more mutations required cumulatively to achieve a desired phenotype, one or more of the insertional mutagenesis events can be achieved in vitro. One or more event can also be achieved in vivo.

The invention accordingly, is also directed to multi-cellular organisms that are produced by any of the methods of the invention.

The invention is also directed to a multi-cellular organism containing at least one cell that comprises a homozygous mutation in a gene, in which both alleles of the gene are mutated by incorporation of an insertional mutagen.

In one embodiment, the first mutagen is identical to the second mutagen. Alternatively, the two mutagens are different.

In one embodiment, one or both of the insertional mutagens is incorporated by non-homologous recombination.

The organism can be screened or selected for mutation of a specific desired gene or for any other desired phenotype.

In one embodiment the first mutagen is identical to the second mutagen. Alternatively, the two mutagens are different.

In one embodiment one or both of the insertional mutagens is incorporated by non-homologous recombination.

Accordingly, the invention is directed to a transgenic animal containing at least one cell that comprises a homozygous mutation wherein both alleles of a gene are mutated by incorporation of an insertional mutation.

In one embodiment the first mutagen is identical to the second mutagen. Alternatively, the two mutagens are different.

In one embodiment one or both of the insertional mutagens is incorporated by non-homologous recombination.

The invention is also directed to a multi-cellular organism containing a cell that comprises a mutation in two or more genes, the mutations being caused by incorporation of an insertional mutagen into the two or more genes, where the mutations are required cumulatively to produce a phenotype in the cell or in the organism.

In one embodiment two or more of the insertional mutagens are identical. Alternatively, two or more of the insertional mutagens are not identical.

In one embodiment one or more of the insertional mutagens is incorporated by non-homologous recombination.

Accordingly, the invention is directed to a transgenic animal containing at least one cell that comprises a mutation in two or more genes, the mutations being caused by incorporation of an insertional mutagen into the two or more genes, and in which the mutations are required cumulatively to produce a phenotype in the cell or in the animal.

In one embodiment two or more of the insertional mutagens are identical. Alternatively, two or more of the insertional mutagens are not identical.

In one embodiment one or more of the insertional mutagens is incorporated by non-homologous recombination.

The invention is also directed to methods for identifying the gene or genes responsible for the phenotypes created by the mutational methods described herein. Identification of the gene or genes is accomplished because the insertional mutagens can be identified and can be used to identify the mutated gene.

The invention is, therefore, directed to a method for identifying a nucleic acid sequence associated with a mutation in a cell. In one embodiment the mutated gene is identified by producing cDNA from the mutated cell, hybridizing it to polynucleotides corresponding to sequences present in the insertional mutagen, and sequencing the cDNA or portion thereof. In another embodiment, the mutated gene is identified by isolating genomic DNA from the mutated cell, hybridizing it to polynucleotides corresponding to sequences present in the insertional mutagen and sequencing the genomic DNA flanking the vector insertion site.

The invention is also directed to a method for identifying a mutated gene in a cell containing a homozygous mutation of an endogenous gene, the method comprising introducing one or more insertional mutagens under conditions suitable for integration of at least two insertional mutagens into the genome of the cell, thereby producing a homozygous disruption of an endogenous gene, isolating RNA from the cell, producing cDNA from the RNA, and hybridizing the cDNA to a sequence from the one or more insertional mutagens, thereby identifying the insertionally mutated gene. The invention is directed to this method further comprising isolating the cDNA that hybridizes to the sequence from the one or more insertional mutagens. The invention is also directed to this method further comprising sequencing the isolated cDNA.

The invention is directed to a method for identifying a mutated gene in a cell containing a homozygous mutation of an endogenous gene, the method comprising, introducing one or more insertional mutagens under conditions suitable for integration of at least two insertional mutagens into the genome of the cell, thereby producing a homozygous disruption of an endogenous gene, isolating genomic DNA from the cell, hybridizing the DNA to a sequence from the one or more insertional mutagens, and sequencing DNA flanking the insertional mutagen thereby identifying the mutated gene.

The invention is directed to a method for identifying a mutated gene present in a cell comprising two or more insertional mutations, the method comprising, introducing one or more insertional mutagens under conditions suitable for integration of at least two insertional mutagens into the genome of the cell, thereby disrupting two or more endogenous genes, isolating RNA from the cell, producing cDNA from the RNA, and hybridizing the cDNA to a sequence from the one or more insertional mutagens, thereby identifying the insertionally mutated gene. The invention is directed to this method further comprising isolating the identified cDNA. The invention is also directed to this method further comprising sequencing the isolated cDNA.

The invention is directed to a method for identifying a mutated gene present in a cell comprising two or more insertional mutations, the method comprising, introducing one or more insertional mutagens under conditions suitable for integration of at least two insertional mutagens into the genome of the cell, thereby disrupting two or more endogenous genes, isolating genomic DNA from the cell, hybridizing the DNA to a sequence from the one or more insertional mutagens, and sequencing DNA flanking the insertional mutagen thereby identifying the mutated gene.

Recovery of cells with mutations in genes can be greatly facilitated by using insertional mutagens that provide a tag for gene sequences and especially active genes. These mutagens will generally disrupt transcription and/or translation and provide for the formation of a fusion RNA or protein. These fusion molecules contain sequences from the mutagen and sequences from the mutated gene. Such fusion transcripts also allow screening for sequences of desired genes and for the identification of mutated genes.

In a preferred embodiment, the insertional mutagen comprises a splice acceptor sequence that may or may not be operably-linked to a promoter sequence. In another preferred embodiment, the insertional mutagen comprises a selectable or screenable marker. This marker may or may not be operably-linked to a promoter or polyadenylation signal. In another preferred embodiment, the splice acceptor sequence is transcriptionally operably-linked to a selectable or screenable marker which may or may not be operably-linked to a promoter or polyadenylation signal. In a further preferred embodiment, the insertional mutagen comprises a 3' gene trap.

In a further preferred embodiment, the insertional mutagen contains site-specific recombination signals. At any stage after a phenotype is produced by mutation, the presence of site-specific recombination sequences on the insertional mutagen can be used to ascertain whether the insertion caused the phenotype. If the excision of the insertional mutagen reverts the phenotype, this indicates that the mutation causing the phenotype was caused by an insertion.

In other preferred embodiments, the insertional mutagen comprises one or more of the following elements: stop codons in all three frames found 3' to a splice acceptor not operably linked to a promoter, an internal ribosome entry site, a selectable marker, and a 3' gene trap. 3' gene traps are described in detail in U.S. application Ser. No. 09/276,820 herein incorporated by reference for the teaching of 3' gene traps (i.e., the "activation" vectors disclosed therein). In the above embodiment, the selectable marker preferably is operably-linked to a polyadenylation signal. In other preferred embodiments, the insertional mutagen contains retrovirus sequences that allow the retrovirus replication and infection cycle. In other preferred embodiments, the insertional mutagen contains sequences necessary for transposition. In a highly preferred embodiment, the insertional mutagen contains a splice acceptor that is not operably-linked to a promoter, the splice acceptor having an optimal branch point, stop codons in all three frames, an internal ribosome entry site that includes an exonic splicing enhancer, a selectable marker with a polyadenylation signal, a 3' gene trap, and wherein these elements are contained in a retrovirus vector or contain transposition signal sequences. In a further preferred embodiment, the insertional mutagen contains a splice acceptor not operably-linked to a promoter, the splice acceptor containing an optimal branch point, stop codons in all three frames, an internal ribosome entry site, a selectable marker with a polyadenylation signal operably linked to it, and wherein the insertional mutagen is a retrovirus vector or contains transposition signals. Furthermore, in any of the embodiments herein and especially in the preferred embodiments of above, preferred insertional mutagens also contain recombination sites for site specific recombination as described herein.

The use of 5' gene trap vectors allows the selection or screening for insertion into transcriptionally active genes. This also results in the ability to considerably reduce the library size. The gene trap can be used to identify cells in which the gene is active when the gene trap is introduced. It is also possible however, with the use of these gene traps, to identify a mutation in a gene that manifests under conditions not present when the insertional mutagen is first incorporated. For example, such a gene may be activated by the presence of external conditions to which the cell is subjected in cell culture (for example, inducible genes) or may manifest when this cell is present in vivo, such as in a transgenic animal.

Expression of the sequences on the mutagen can be a function of insertion into a gene or active gene. Cells can be screened or selected for expression of the sequences on the mutagen. If the sequence affects cell survival, cells expressing the sequence will not even survive (e.g., if the mutagen contains a marker that is a negatively selectable marker) or will survive (e.g., if the mutagen contains a marker that is a positive selectable marker). Accordingly, cells having mutations in active genes can be selected for by having a positive selectable marker on the vector, wherein expression of the positive selectable marker depends on active expression of the endogenous gene. Cells will survive only if the marker is expressed and the marker is expressed only if the gene is active.

A negative selectable marker can be used for selecting cells with insertional mutations in transcriptionally silent genes. The marker is placed on the vector so that the expression of the marker depends on active expression of a gene. After exposure to the mutagen, cells that have insertions in transcriptionally active genes and which, therefore, express the marker, can be eliminated when the cells are subjected to negative selection. Cells containing insertions in silent genes will survive since the marker is not expressed. Accordingly, a library of cells with mutations in silent genes can be recovered. The number can be relatively small.

When multiple insertional mutagens are used, each mutagen can comprise a different marker, allowing cells with the different selectable markers to be selected independently.

The invention also provides methods of using the cells, organisms, and libraries to select or screen for phenotypes that are created by the mutagenesis methods of the invention and to identify one or more mutations responsible for the phenotype.

The methods of the invention provide a way to establish the function of a gene. With the methods it is possible to determine the function of any specific desired gene. Cells can be mutated and screened or selected for a mutation in a specific desired gene with any assay that can be used to specifically detect a mutation in that gene. The effect of the mutation on the cell or animal can then be ascertained. In this case, the tagged insertional mutagen is useful for identification of cells containing mutation of the gene of interest.

Alternatively, mutated cells can be screened or selected at random for a desired phenotype, or for production of a desired phenotype in a multi-cellular organism made from the cell, and the phenotype can be then correlated with mutation in one or more genes by means of the tag. Alternatively, a cell that is mutated can be selected or screened on the basis of the phenotype it has or confers on an organism made from the cell, and that phenotype can then be correlated with mutation in one or more genes by means of the tag. Thus, any change in phenotype of the cell (or of multicellular organism derived from the cell) from that of the non-mutated cell (or cellular organism) can be ascribed to the mutated gene. Mutated genes that give rise to desired phenotypes can be identified, and characterized e.g., cloned, sequenced, mapped, etc. According to this aspect of the invention, the function of any gene can be identified and assessed. Thus, a phenotype can be correlated with a gene that is known in the art (previously identified, e.g., mapped, cloned, sequenced, or otherwise characterized) or with a gene that is not known in the art.

The invention also encompasses the use of the mutant cells for drug screening. In this embodiment, mutant cells are exposed to test compounds or compositions which may have therapeutic potential, to determine the effect of the compound or composition on a desired phenotype induced by one or more mutations in the mutant cells, including the level of expression or activity of the mutated gene or protein. Furthermore, the wildtype genes or other variants that correspond to the mutated gene or genes, also can be used to identify drugs, that affect a phenotype caused by the gene or genes, including the level of expression or activity of the wildtype or variant gene or protein of interest.

Other preferred embodiments of the present invention will be apparent to one of ordinary skill in light of what is known in the art, in light of the following drawings and description of the invention, and in light of the claims.

BRIEF DESCRIPTION OF THE DRAWINGS/FIGURES

FIGS. 1A-1J: Non-limiting examples of 5' gene trap insertional mutagens vectors useful in the present invention. Each insertional mutagen is illustrated schematically in its linear form; however, insertional mutagens of the invention can have any geometry (linear, circular, coiled, supercoiled, etc.). Horizontal lines and boxes indicate polynucleotides, such as DNA or RNA. Stop codons can be present in any reading frame, or nested such that they are present in all reading frames. S/A represents a splice acceptor site. S/D represents a splice donor site. pA represents a polyadenylation signal. ET represents an epitope tag.

FIGS. 2A-2H: Non-limiting examples of 5' gene trap insertional mutagens useful in the present invention. Each insertional mutagen is illustrated schematically in its linear form. Horizontal lines and boxes indicate polynucleotides such as DNA or RNA. SM and RG represent selectable marker and reporter gene, respectively. S/A represents a splice acceptor site. S/D represents a splice donor site. pA represents a polyadenylation signal. IRES represents internal ribosomal entry site.

Figures 3A, 3B:
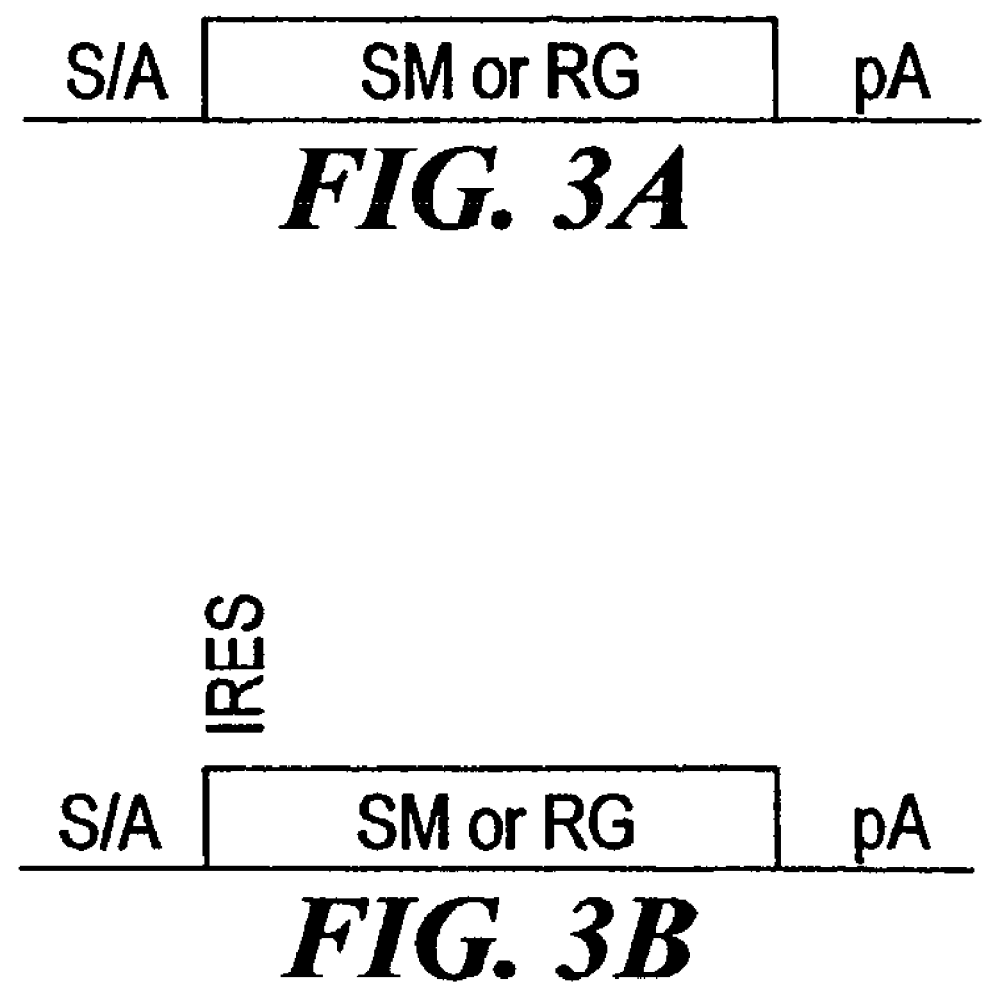

FIGS. 3A-3B: Non-limiting examples of 5' gene trap insertional mutagens useful in the present invention. Each insertional mutagen is illustrated schematically in its linear form. Horizontal lines and boxes indicate polynucleotides such as DNA or RNA. SM and RG represent selectable marker and reporter gene, respectively. S/A represents a splice acceptor site. pA represents a polyadenylation signal. IRES represents internal ribosomal entry site.

Figure 4A:
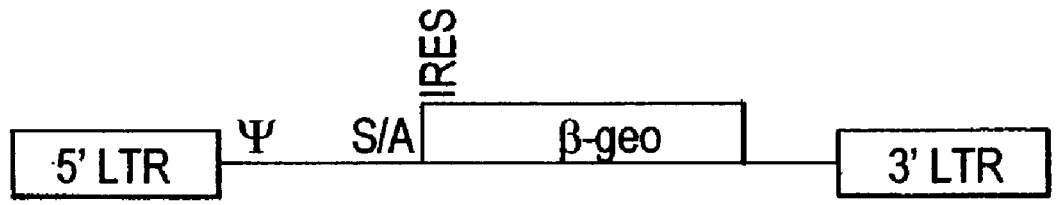
Figure 4B:
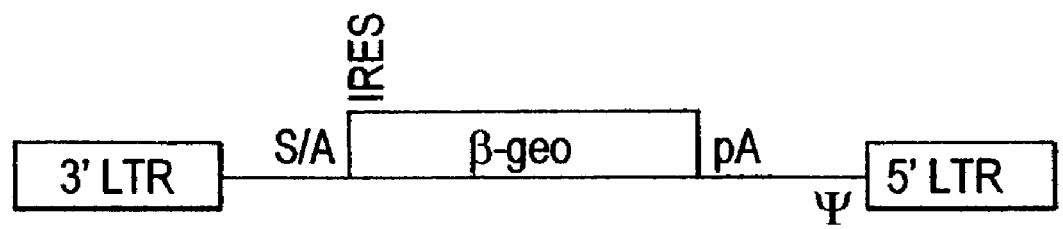
Figure 4C:
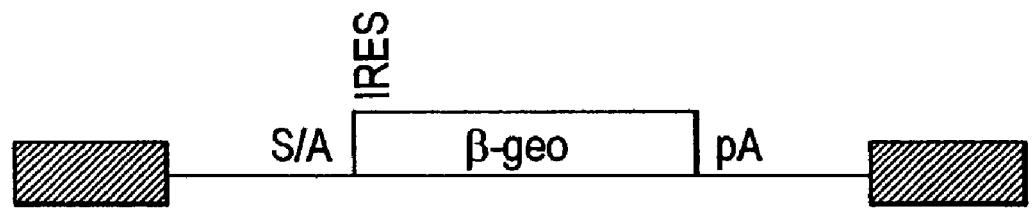

FIGS. 4A-4C: Non-limiting examples of 5' gene trap insertional mutagens useful in the present invention. Each insertional mutagen is illustrated schematically in its linear form. Horizontal lines and boxes indicate polynucleotides such as DNA or RNA. β-geo is a fusion of the neomycin resistance gene and β-galactosidase gene. S/A represents a splice acceptor site. pA represents a polyadenylation signal. IRES represents internal ribosomal entry site. 5' LTR and 3' LTR represent retroviral long terminal repeats. ψ represents retroviral packaging signal. In FIG. 4B, the 5' LTR, 3' LTR, and ψ are shown upside down to indicate that the retroviral sequence is in reverse orientation relative to the splice acceptor site and β-geo gene. In FIG. 4C, the solid boxes represent transposon signals.

Figure 5A:
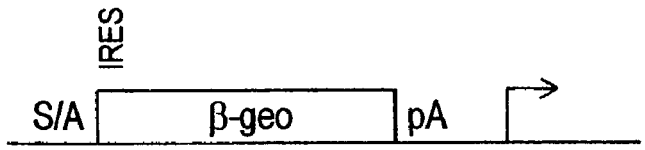
Figure 5B:
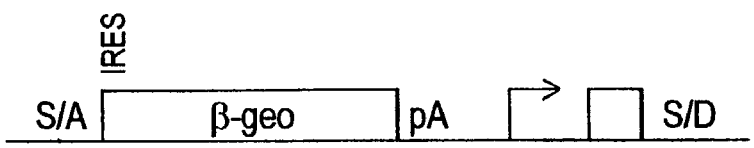
Figure 5C:
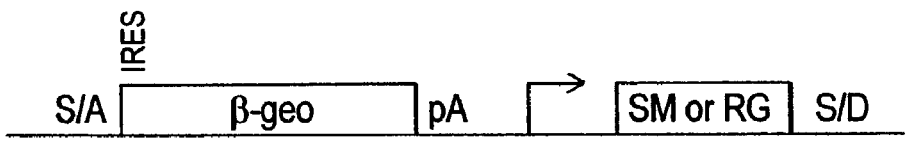
Figure 5D:
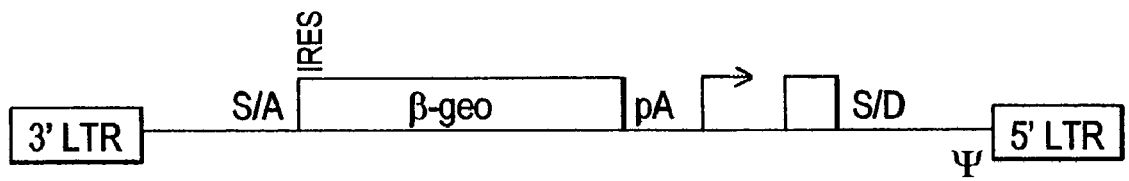
Figure 5E:
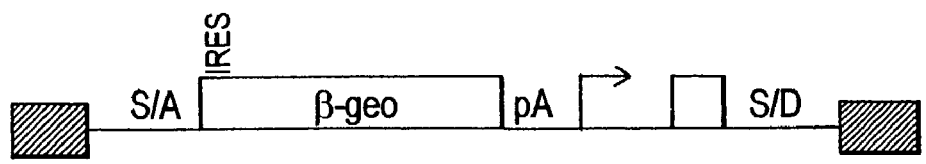

FIGS. 5A-5E: Non-limiting examples of 5' gene trap insertional mutagens containing a 3' gene trap component. Each insertional mutagen is illustrated schematically in its linear form. Horizontal lines and boxes indicate polynucleotides such as DNA or RNA. Arrows represent promoters. SM and RG represent selectable marker and reporter gene, respectively. β-geo is a fusion of the neomycin resistance gene and β-galactosidase gene. S/A represents a splice acceptor site. S/D represents a splice donor site. pA represents a polyadenylation signal. IRES represents internal ribosomal entry site. 5' LTR and 3' LTR represent retroviral long terminal repeats. ψ represents retroviral packaging signal. In FIG. 5D, the 5' LTR, 3' LTR, and ψ are shown upside down to indicate that the retroviral sequence is in reverse orientation relative to the splice acceptor site and β-geo gene. In FIG. 5E, the solid boxes represent transposon signals.

Figure 6A:
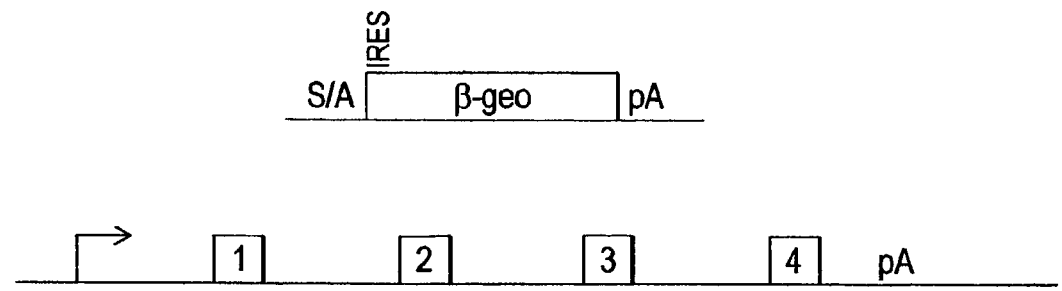
Figure 6B:
Figure 6B:
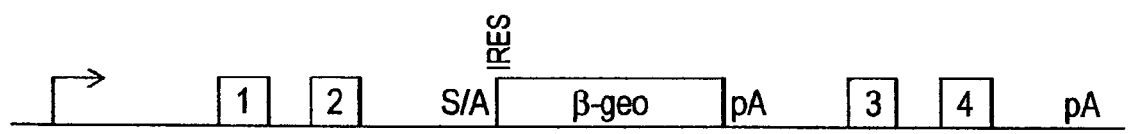
Figure 6C:
Figure 6C:
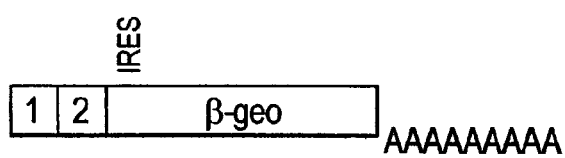

FIGS. 6A-6C: Proposed mechanism of gene mutation using a 5' gene trap. Vector is illustrated schematically in its linear form. Horizontal lines and boxes indicate polynucleotides such as DNA or RNA. Arrows represent promoters. β-geo is a fusion of the neomycin resistance gene and β-galactosidase gene. S/A represents a splice acceptor site. pA represents a polyadenylation signal. IRES represents internal ribosomal entry site. FIG. 6A shows the insertional mutagen and the endogenous gene prior to vector insertion. FIG. 6B shows the endogenous gene following insertion of the insertional mutagen. FIG. 6C shows the fusion mRNA produced from the endogenous gene.

Figure 7A:
Figure 7B:
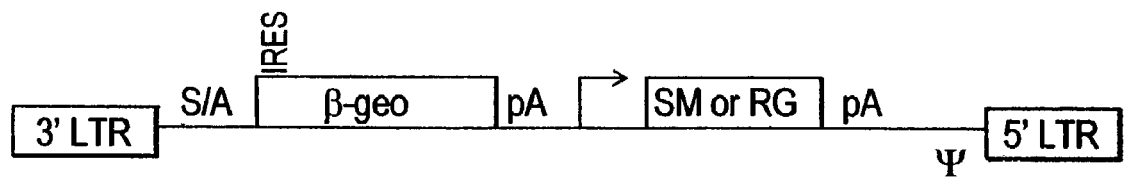

FIGS. 7A-7B: Non-limiting examples of 5' gene trap insertional mutagens containing a promoter linked to a selectable marker or reporter gene followed by a polyadenylation signal. Each insertional mutagen is illustrated schematically in its linear form. Horizontal lines and boxes indicate polynucleotides, such as DNA or RNA. Arrows represent promoters. SM and RG represent selectable marker and reporter gene, respectively. β-geo is a fusion of the neomycin resistance gene and β-galactosidase gene. S/A represents a splice acceptor site. pA represents a polyadenylation signal. IRES represents internal ribosomal entry site. 5' LTR and 3' LTR represent retroviral long terminal repeats. ψ represents retroviral packaging signal. In FIG. 7B, the 5' LTR, 3' LTR, and ψ are shown upside down to indicate that the retroviral sequence is in reverse orientation relative to the splice acceptor site and β-geo gene. The presence of the promoter operably linked to a selectable marker/reporter gene and polyadenylation signal allows selection of integrated insertional mutagens independent of whether or not integration has occurred in a transcriptionally active region of the genome. The figure is illustrative of several insertional mutagen types containing selectable markers; however, the promoter/selectable marker/polyadenylation signal unit can be used on any of the insertional mutagens described herein.

Figure 8A:
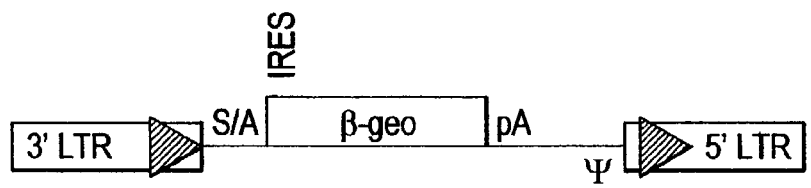
Figure 8B:
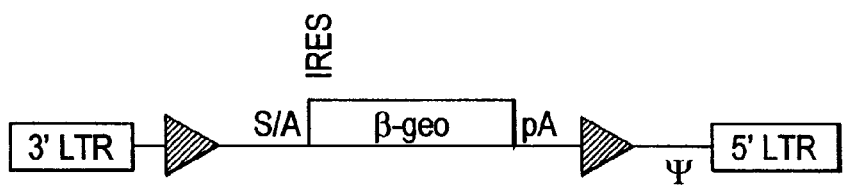
Figure 8C:
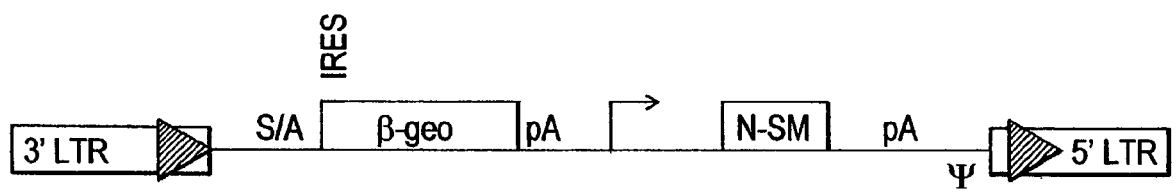

FIGS. 8A-8C: Non-limiting examples of 5' gene trap insertion insertional mutagens containing site-specific recombination signals. Each insertional mutagen is illustrated schematically in its linear form. Horizontal lines and boxes indicate polynucleotides such as DNA or RNA. Arrows represent promoters. Filled triangles represent site-specific recombination signals. The site-specific recombination signals can be in any orientation relative to one another. The figure depicts an orientation that promotes excision of the insertional mutagen from the genome. If the signals are placed on the insertional mutagen in the opposite direction relative to each other, the insertional mutagen would be inverted in the genome following site specific recombination. N-SM represents a negative selectable marker gene. β-geo is a fusion of the neomycin resistance gene and β-galactosidase gene. S/A represents a splice acceptor site. pA represents a polyadenylation signal. IRES represents internal ribosomal entry site. 5' LTR and 3' LTR represent retroviral long terminal repeats. ψ represents retroviral packaging signal. In each example, the 5' LTR, 3' LTR, and ψ are shown upside down to indicate that the retroviral sequence is a reverse orientation relative to the splice acceptor site and β-geo gene. The position of the site-specific recombination signals in FIGS. 8A and 8C is shown in the viral LTRs such that most of the viral insertional mutagen can be excised (see, e.g., Ishida, *Nucl. Acids Res.* 27: e35 (1999)). The presence of the promoter operably linked to a negative selectable marker and polyadenylation signal allows selection for cells in which the integrated insertional mutagen has been excised. The present figure is illustrative of several insertional mutagen types containing site-specific recombination signals; however, the site-specific recombination signals can be used on any of the insertional mutagens described herein, including the non-viral insertional mutagens.

FIGS. 9A-9H: Non-limiting examples of 5' gene trap insertional mutagens containing site-specific recombination signals (also equivalently referred to herein as recombination sites). Each insertional mutagen is illustrated schematically in its linear form (although insertional mutagens can exist in any conformation, including linear, circular, coiled, supercoiled, branched, etc.). Horizontal lines and boxes indicate polynucleotides such as DNA or RNA. Arrows represent promoters. Filled triangles represent site-specific recombination signals. The site-specific recombination signals can be in any orientation relative to one another. Recombination sites shown in opposite orientation relative to one another (e.g., FIGS. 9D-9F and 9H) produce an inversion following recombination, whereas recombination sites shown in the same orientation relative to one other (e.g., FIGS. 9A-9C and 9G) produce a deletion upon recombination. N-SM represents a negative selectable marker gene, while P-SM represents a positive selectable marker gene. Neo represents a neomycin resistance gene. TK represents a herpes virus thymidine kinase (HSV-TK) gene. S/A represents a splice acceptor site. pA represents a polyadenylation signal. IRES represents an internal ribosome entry site. The presence of the promoter operably linked to a negative selectable marker and polyadenylation signal allows selection for cells in which the integrated insertional mutagen has been excised. Where the positive selectable marker and/or the negative selectable marker lack a promoter on the insertional mutagen, the marker can be expressed from an endogenous promoter upon integration of the insertional mutagen into the genome of the host cell. The present figure is illustrative of several insertional mutagen types containing site-specific recombination signals; however, the recombination sites can be used on any of the insertional mutagens described herein, including the non-viral insertional mutagens. In addition, any of the insertional mutagens shown in this figure can optionally contain no (or only one) site-specific recombination signal(s). The insertional mutagens depicted in FIGS. 9A-9F can optionally lack the S/A, IRES and/or pA signal. Each of the insertional mutagens shown optionally can be configured as a viral insertional mutagen and therefore can contain 5' and 3' LTRs and packaging signals. As one of ordinary skill will readily appreciate, other insertional mutagen elements described herein and/or recognized in the art can be included in the insertional mutagens in addition to the elements illustrated in the figures.

Figure 9A:
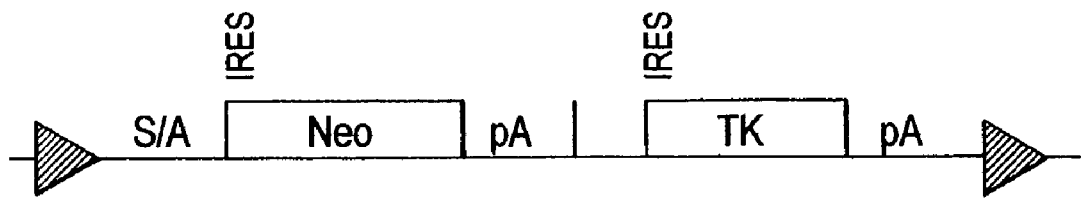
Figure 9B:
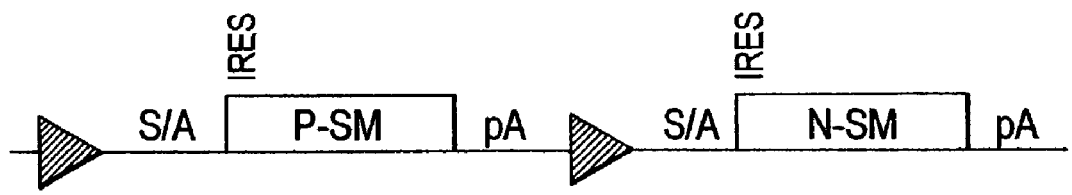
Figure 9C:
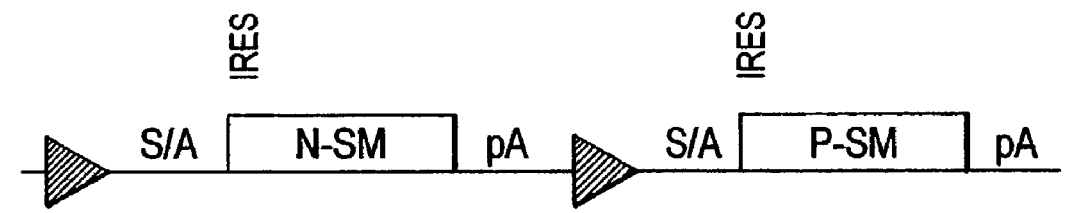
Figure 9D:
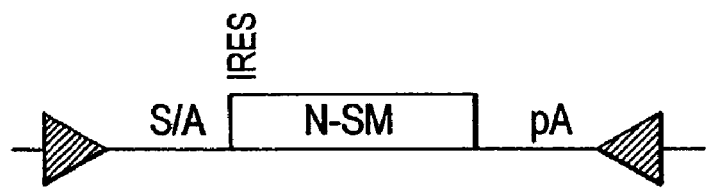
Figure 9E:
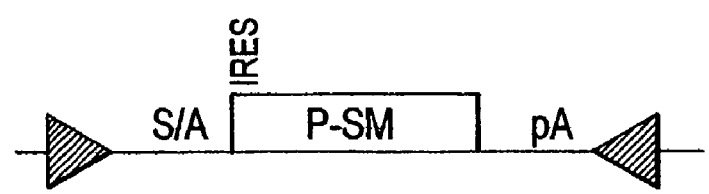
Figure 9F:
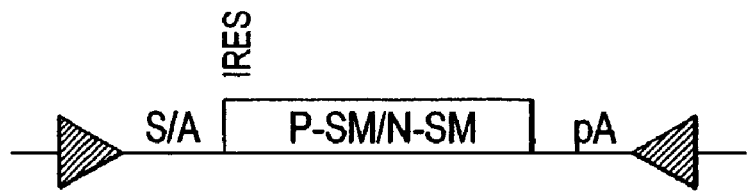
Figure 9G:
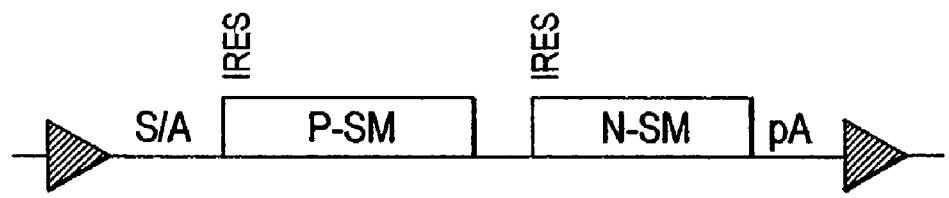
Figure 9H:
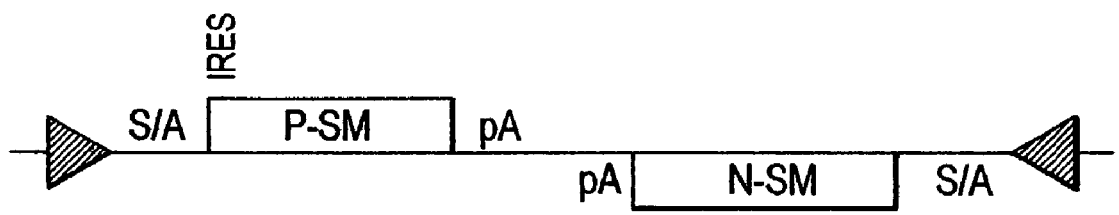
Figure 10A:
Figure 10B:
Figure 10C:
Figure 10D:
Figure 10E:
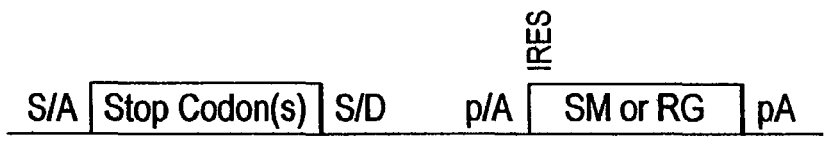
Figure 10F:
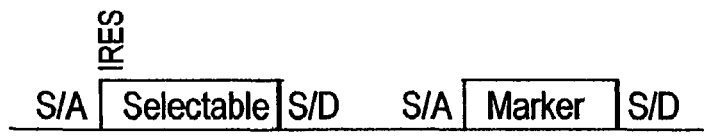
Figure 10G:
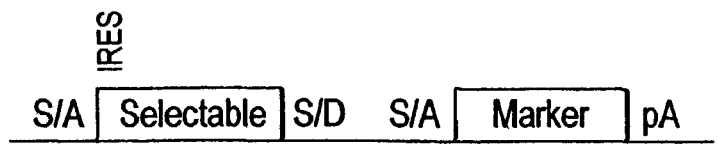

FIGS. 10A-10G: Non-limiting examples of 5' gene trap insertional mutagens containing multiple exons. Each insertional mutagen is illustrated schematically in its linear form (although vectors can exist in any conformation, including linear, circular, coiled, supercoiled, branched, etc.). Horizontal lines and boxes indicate polynucleotides such as DNA or RNA. Arrows represent promoters. S/A represents a splice acceptor site, and S/D represents a splice donor site. pA represents a polyadenylation signal. IRES represents an internal ribosome entry site. SM indicates a positive or negative selectable marker. A reporter gene can be substituted for the SM on any of the insertional mutagens shown in this figure. In FIG. 10F and 10G, the selectable marker open reading frame has been separated onto different exons. Upon transcription from an endogenous gene, followed by splicing, the open reading frame will be reconstituted to produce a functional SM. It will be recognized by the ordinarily skilled artisan that each of the insertional mutagens depicted in this figure can optionally contain one or more site-specific recombination signals (see FIG. 9). Optionally, the insertional mutagens depicted in this figure can lack the S/A, IRES, S/D and/or pA signal. Each of the insertional mutagens shown optionally can be configured as a viral insertional mutagen and therefore can contain 5' and 3' LTRs and packaging signals. As one of ordinary skill will readily appreciate, other elements described herein and/or recognized in the art can be included in the insertional mutagens in addition to the elements illustrated in the figures.

Figure 11:
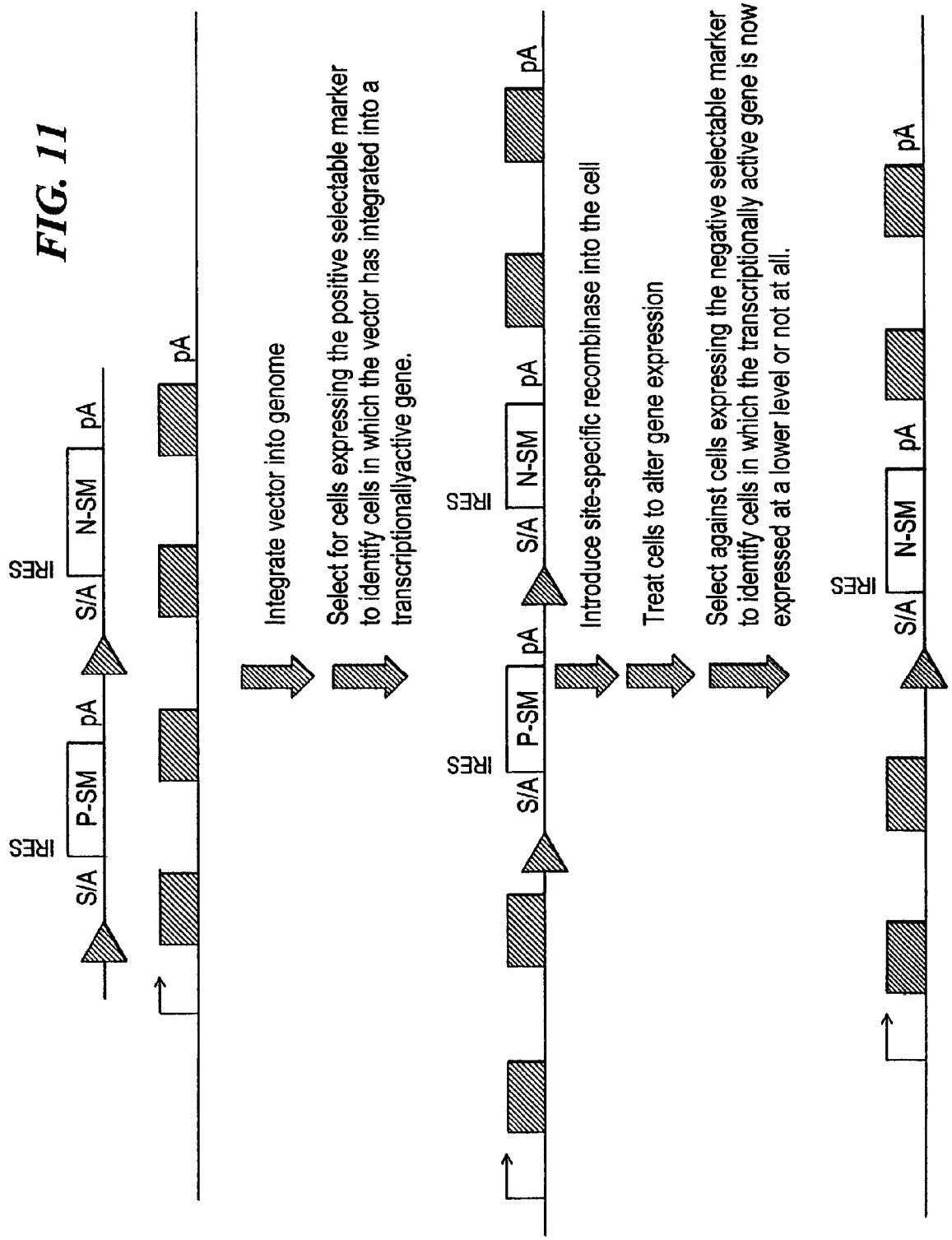

FIG. 11: Method for detecting gene trap insertions that occur in developmentally regulated genes. In this example, cells are identified in which a transcriptionally active gene became down regulated or silenced in response to specific treatments or environmental stimuli to the cells. DNA is illustrated schematically in its linear form. Horizontal lines and boxes indicate polynucleotides such as DNA or RNA. Arrows represent promoters. Filled triangles represent site-specific recombination signals. The site-specific recombination signals are depicted in an orientation that promotes excision of the positive selectable marker from the genome. P-SM and N-SM represent positive selectable marker and negative selectable marker, respectively. S/A represents a splice acceptor site. S/D represents a splice donor site. pA represents a polyadenylation signal. IRES represents internal ribosomal entry site.

Figure 12:
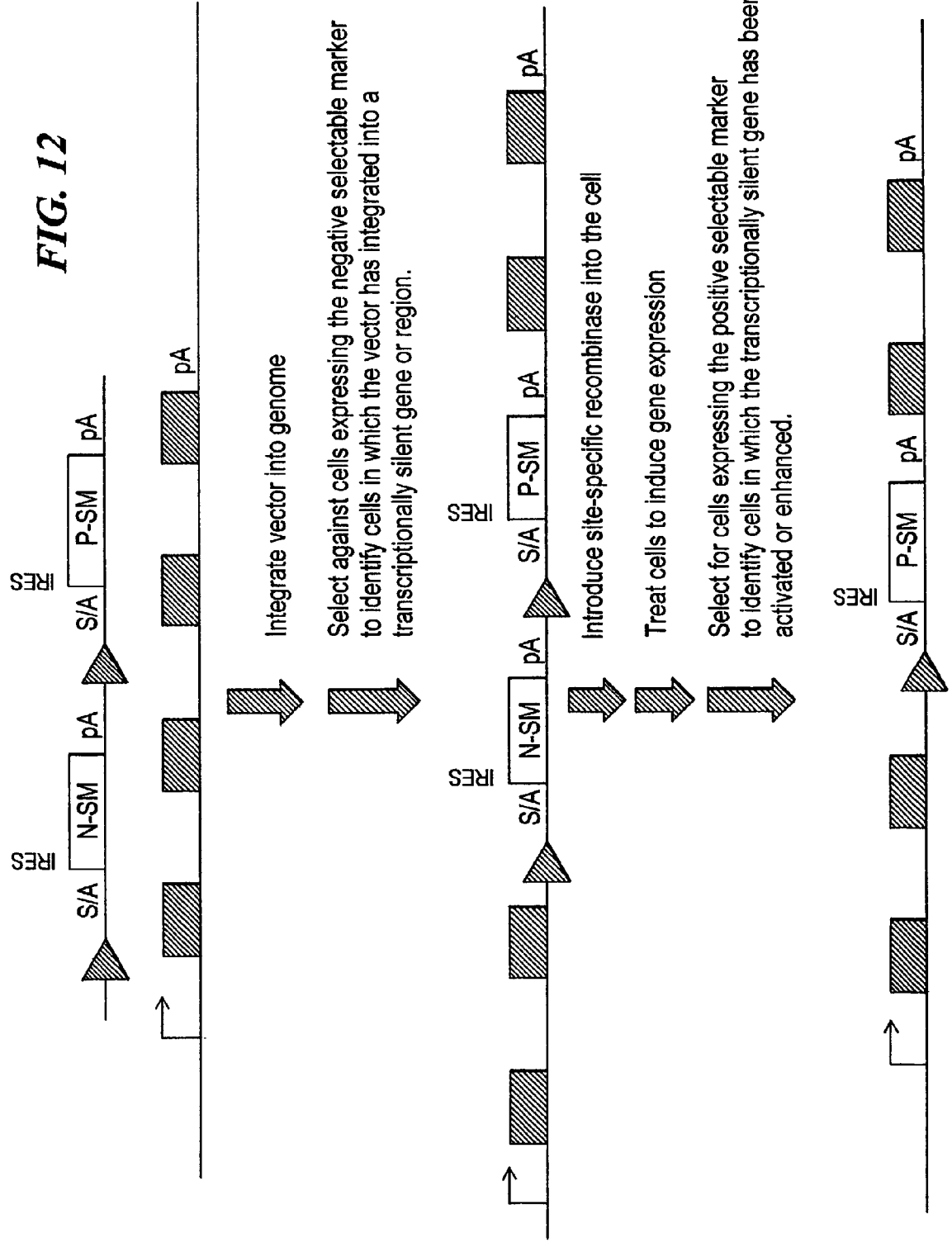

FIG. 12: Method for detecting gene trap insertions that occur in developmentally regulated genes. In this example, cells are identified in which a transcriptionally silent gene (or minimally expressed gene) became turned on or enhanced in response to specific treatments or environmental stimuli to the cells. DNA is illustrated schematically in its linear form. Horizontal lines and boxes indicate polynucleotides such as DNA or RNA. Arrows represent promoters. Filled triangles represent site-specific recombination signals. The site-specific recombination signals are depicted in an orientation that promotes excision of the negative selectable marker from the genome. P-SM and N-SM represent positive selectable marker and negative selectable marker, respectively. S/A represents a splice acceptor site. S/D represents a splice donor site. pA represents a polyadenylation signal. IRES represents internal ribosomal entry site.

Figure 13:
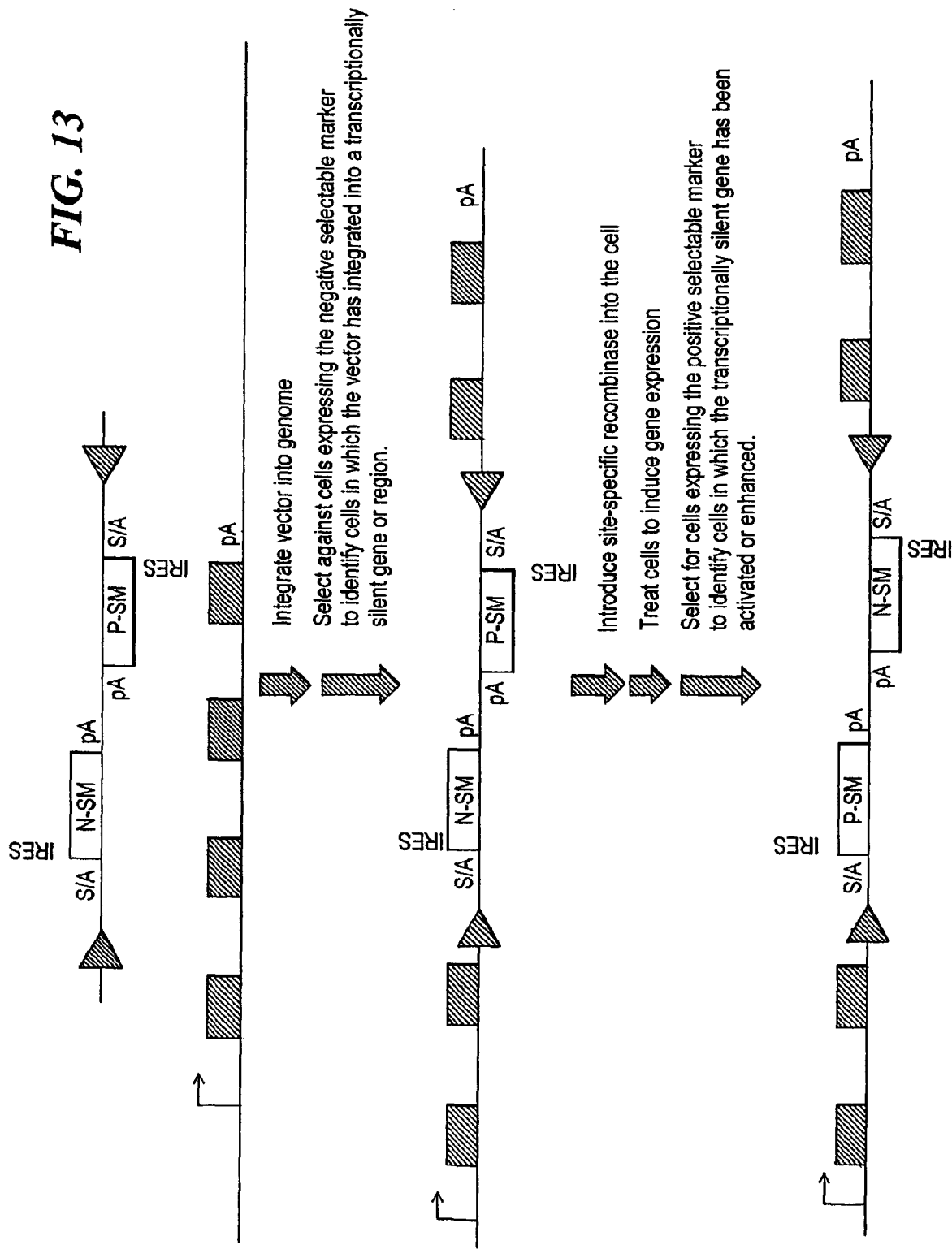

FIG. 13: Method for detecting gene trap insertions that occur in developmentally regulated genes. In this example, cells are identified in which a transcriptionally silent gene (or minimally expressed gene) became turned on or enhanced in response to specific treatments or environmental stimuli to the cells. In other examples, it is possible to identify cells in which a transcriptionally active gene became down regulated or silenced in response to specific treatments or environmental stimuli to the cells. This is accomplished using the vector shown in this figure in combination with the selection scheme shown in FIG. 11 (i.e. selection for the positive selectable marker, then treatment of cells with an agent capable of altering its expression pattern, and selecting against cells expressing the negative selectable marker). DNA is illustrated in its linear form. Horizontal lines and boxes indicate polynucleotides such as DNA or RNA. Arrows represent promoters. Filled triangles represent site-specific recombination signals. The site-specific recombination signals are depicted in an orientation that promotes inversion of the positive and negative selectable markers within the genome. P-SM and N-SM represent positive selectable marker and negative selectable marker, respectively. S/A represents a splice acceptor site. S/D represents a splice donor site. pA represents a polyadenylation signal. IRES represents internal ribosomal entry site.

Figure 14:
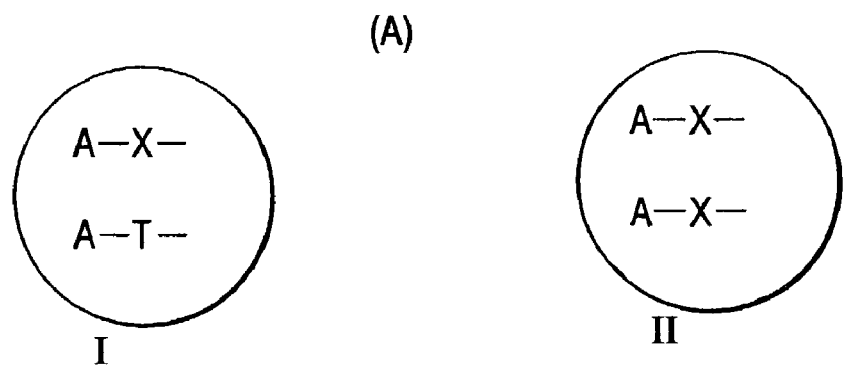
Figure 14:
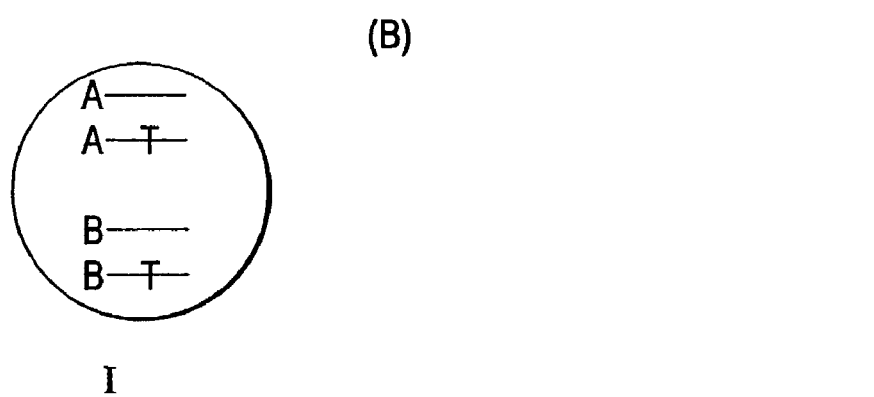
Figure 14:
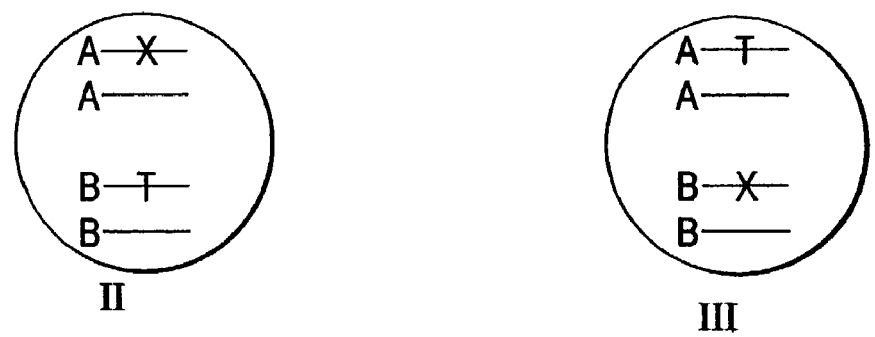
Figure 14:
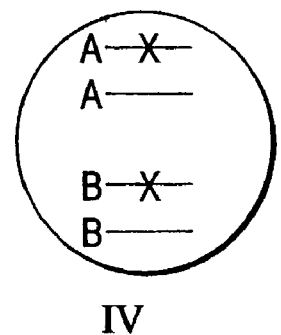
Figure 14:
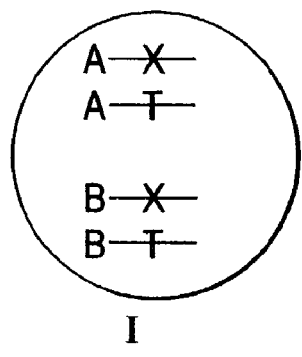
Figure 14:
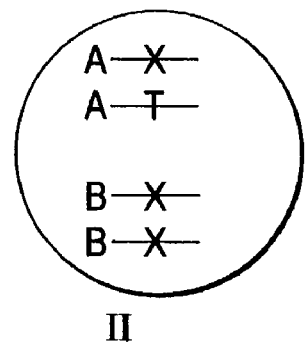
Figure 14:
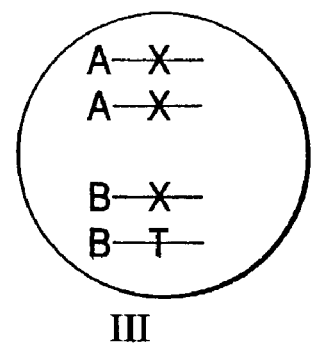
Figure 14:
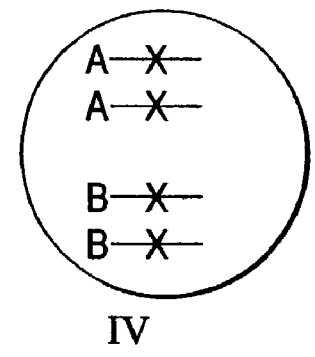

FIG. 14: The Figure schematically shows non-limiting examples of cells that result from mutagenesis according to the present invention and examples of how genes could be tagged for detection. "X" denotes one insertional event. "T" denotes a tag introduced by another insertional mutagenesis event, which can be used to identify a gene associated with a phenotype.

(A) Phenotype results from homozygous mutation of single gene. Both copies of gene A contain a mutation. The gene can be identified by the tag on one copy. Only one cell is required to identify the gene responsible for the phenotype (I). Cell II can be discarded.

(B) Phenotype results from heterozygous mutation of two different genes. Cell I allows identification, in the same cell, of the two genes responsible for the phenotype. Cells II and III are used in combination to identify both genes responsible for the phenotype or separately to identify one of the genes responsible for phenotype. Cell IV can be discarded.

(C) Phenotype results from heterozygous mutation of Gene A and homozygous mutation of Gene B. Cell I allows identification, in the same cell, of the two genes responsible for the phenotype. Cells II and III are used in combination to identify both genes responsible for the phenotype or separately to identify one of the genes responsible for phenotype. Cell IV can be discarded.

(D) Phenotype results from homozygous mutation of two different genes. Cell I allows identification, in the same cell, of the two genes responsible for the phenotype. Cells II and III are used in combination to identify both genes responsible for the phenotype or separately to identify one of the genes responsible for phenotype. Cell IV can be discarded.

Figure 15:
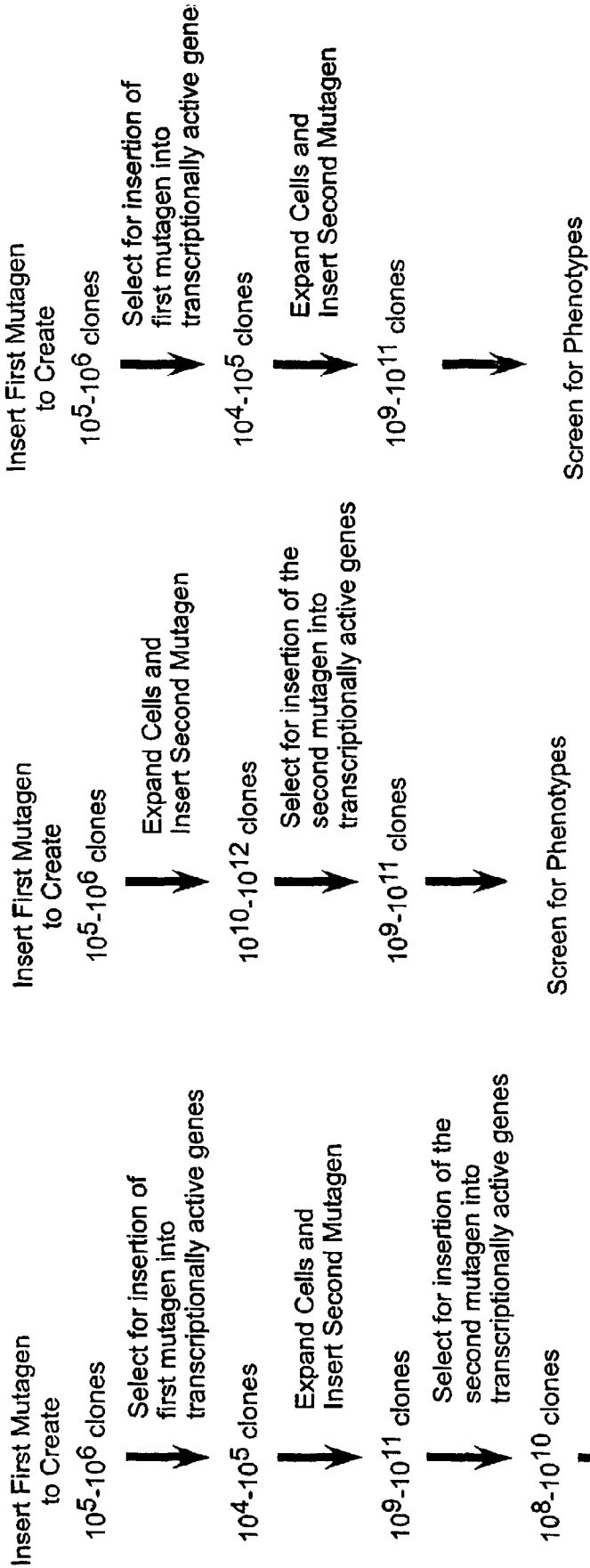

FIG. 15: Non-limiting examples of mutagenic processes and numbers of clones useful in mammalian cells (see FIG. 4B for an example of a vector useful in selecting transcriptionally active genes). In process number 1, a first insertional mutagen is inserted into the genome of a population of cells to produce the specified number of clones (cells with one or more insertions in the genome). Cells containing the first mutagen are then placed under selection for insertion of the mutagen into a transcriptionally active gene by means of a selectable marker present on the insertional mutagen. Cells are then expanded so that each clone now contains a number of cells sufficient for insertion of a second mutagen to produce $10^9$-$10^{11}$ clones. The first mutagen and the second mutagen typically contain different selectable markers to allow gene traps from each mutagen to be selected independently. Following insertion of the second mutagen, cells are then selected for insertion of the mutagen into a transcriptionally active gene. Every finally selected clone, therefore, contains both insertional mutagens, each integrated into transcriptionally active genes. Cells can then be screened for phenotypes of interest.

In process number 2, a first insertional mutagen is inserted into the genome of a population of cells to produce the specified number of clones. Clones containing the first mutagen are not selected. These cells are expanded such that each clone now contains a number of cells sufficient for insertion of a second mutagen to produce $10^{10}$-$10^{12}$ clones. Following insertion of the second mutagen, cells are then selected for insertion of the mutagen into a transcriptionally active gene. Cells that are finally produced contain both insertional mutagens. Every cells contains the first mutagen integrated throughout the genome (i.e., in transcriptionally active and silent genes and in non-genic regions) and every cell contains the second mutagen integrated into only transcriptionally active genes. Cells can then be screened for phenotypes of interest.

In process number 3, a first insertional mutagen is inserted into the genome of a population of cells to produce the specified number of clones. Cells containing the first mutagen are then placed under selection for insertion of the mutagen into a transcriptionally active gene by means of the selectable marker present on the insertional mutagen. Cells are then expanded such that each clone now contains a number of cells sufficient for insertion of a second mutagen to produce $10^9$-$10^{11}$ clones. Cells that are finally produced in this process contain both insertional mutagens. Every cell contains the first mutagen integrated into only transcriptionally active genes and every cell contains the second mutagen integrated throughout the genome (i.e., in transcriptionally active and silent genes and in non-genic regions). These cells can be screened for phenotypes of interest.

DETAILED DESCRIPTION OF THE INVENTION

Definitions

In the description that follows, a number of terms used in recombinant DNA technology are utilized extensively. In order to provide a clear and consistent understanding of the specification and claims, including the scope to be given such terms, the following definitions are provided.

"Insertional mutagenesis", as it relates to the invention, means a process in which a polynucleotide is inserted into the genome of a cell in such a way so as to mutate an endogenous gene. As used herein the terms "incorporation" or "integration" or "insertion" into an endogenous gene are used synonymously. Introduction of an insertional mutagen can be exogenously or may occur following activation of an endogenous insertional mutagen, such as a transposon. Therefore, the event that causes the homozygous mutation by mutation in the second allele, or which causes mutation in a gene to complete the mutation of a set of genes, where the mutation is cumulatively required to produce a phenotype in a cell or animal, may not be an insertion event that results directly from insertion of an insertional mutagen introduced exogenously. This mutagenesis event can occur from insertions of an endogenous insertional mutagen, such as a transposon.

Insertional mutagenesis can occur when an insertional mutagen is introduced into a cell exogenously and, as a result of the exogenous introduction, becomes incorporated into the genome so as to mutate one or more endogenous genes. The invention, however, is also directed to mutagenesis events that occur when an endogenous insertional mutagen is caused to insert into new locations in addition to or in place of its insertion in the original location. Thus, it is induced or activated endogenously, such as in the case of a transposable element which is induced to further transposition by the action of a transposase, introduced exogenously or already present in the cell but induced to be expressed. Accordingly, in one embodiment of the invention, insertional mutation of an allele or a gene results from transposition of an endogenous insertional mutagen. This endogenous insertional mutagen may be naturally-occurring in the cell or may have been introduced into the cellular genome or the genome of a precursor cell such as a precursor cell in vitro or precursor cell in vivo.

In one aspect of simultaneous introduction of different mutagens to a cell, one or more of the mutagens is produced endogenously. One or more mutagens is present in the genome of the cell and can provide for further insertion into the genome at one or more new locations. Thus, simultaneous mutagenesis can occur by causing the new insertions of one or more different mutagens from within the cell and can also occur when this endogenous introduction is concurrent in time with the introduction of an exogenous mutagen.

The mutation can result in a change in the expression level of a gene or level of activity of a gene product. "Activity" encompasses all functions of a gene product, e.g. structural, enzymatic, catalytic, allosteric, and signaling. In one embodiment, mutation results in a decrease or elimination of gene expression levels (RNA and/or protein) or a decrease or elimination of gene product activity (RNA and/or protein). In another embodiment, the insertional mutagen increases expression or activity of a gene or gene product. Thus, an insertional mutagen can also act to increase or to qualitatively change (e.g. altered substrate on binding specificity, or regulation of protein activity) the activity of the product of the mutated gene.

The insertional mutagens can also be used to "tag" the mutated gene at least at the DNA level, and in one embodiment, at the RNA or protein level, depending on the insertional mutagen. The mutagenic sequence may by itself be detectable so as to "tag" the insertionally mutated gene or product of the gene.

Thus, as used herein, the term "tag" refers to a structural or functional feature (typically, a nucleotide sequence) contained on an insertional mutagen of the invention, which permits the location (in DNA, RNA, cDNA, etc.) of the insertional mutagen to be determined once it has been inserted into a target nucleic acid molecule via recombination (e.g., into the genome of a target cell). The tag, accordingly, not only enables location of the insertional mutagen, it enables the gene into which the vector has inserted to be identified. Examples of tags include, but are not limited to, nucleotide sequences encoding a reporter gene (e.g., β-lactamase, β-galactosidase, luciferase, chloramphenicol acetyl transferase, green fluorescent protein and its derivatives, yellow fluorescent protein and its derivatives, blue fluorescent protein and its derivatives, cyan fluorescent protein and its derivatives, red fluorescent protein and its derivatives, and the like), and nucleotide sequences encoding a selectable marker (which may be a positive selectable marker or a negative selectable marker). It should be recognized however that a tag, for purposes of the invention need not encode a protein. It simply provides a sequence that allows detection of either the tag itself or of a nucleotide sequence adjacent to or otherwise linked to the tagged sequence.

The "tag" can also provide the property that the insertional mutagen can be detected such that a cell containing the insertional mutagen can be detected (and isolated, if desired, or otherwise specifically manipulated).

"5' gene traps" are insertional mutagens that are designed to prevent or reduce functional expression of a given endogenous gene upon insertion of the mutagen into the gene. 5' gene traps alter gene expression by interrupting the normal splicing or exon structure of the primary transcripts of mutated genes. Splicing interruption is accomplished by splicing of upstream exons of the mutated gene onto splice acceptor sequences within the insertional mutagen. This change in splicing often disrupts the protein coding of transcripts of the mutated gene. Alternatively, the insertional mutagen can insert directly into and disrupt the coding potential of exons of the mutated gene.

"3' gene traps" are insertional mutagens that are designed to activate or otherwise enhance transcription of, and optionally translation of, endogenous exons of the gene in which the mutagenic vector is inserted. 3' gene traps function by initiating transcription of mutated genes at promoter sequences located within the insertional mutagen. Transcripts initiated in the mutagenic vector continue 3' of the insertion site to include downstream exons of the mutated gene in chimeric primary transcripts. Exons containing vector sequence can optionally splice onto exons of the mutated gene to generate chimeric transcripts that encode proteins including all or C-terminal fragments of the normal protein product of the mutated gene.

As disclosed herein, the invention is also directed to producing mutations in a set of genes in which mutation of each gene in the set is required cumulatively to produce the mutant phenotype. The mutations may be heterozygous. Such mutations are known in the art as "trans-heterozygous" mutations.

As used herein, "gene knock-out" means that the expression of a gene has been eliminated. "Gene knock-down" means that the expression of a gene has been decreased.

As used herein, "decrease" means that a given gene has been mutated such that the level of gene expression or level of activity of a gene product in a cell or organism is reduced from that observed in the wildtype or non-mutated cell or organism. This is often accomplished by reducing the amount of mRNA produced from transcription of a gene, or by mutating the mRNA or protein produced from the gene such that the expression product is less abundant or less active.

The term "gene disruption" as used herein refers to a gene knock-out or knock-down in which an insertional mutagen is integrated into an endogenous gene thereby producing a mutated transcript or protein. A fusion transcript or fusion protein comprising endogenous exon sequence and sequence in the insertional mutagen may be produced. Alternatively, the transcript or protein may be less than full length or may be entirely absent.

As used herein, and unless otherwise indicated, "a" or "an" means one or more.

In referring to a cell that is insertionally mutated, it is understood that sequential mutagenesis events in a cell can be in a parental cell and/or in its clonal progeny.

As used herein, the term "mutated clone" refers to one or more progeny cells arising from a mutated parent cell created with mutagenesis methods of the invention. A "clone" is understood to refer to one or more cells with the same genotype with respect to the integration site(s) of insertional mutagen(s).

As used herein, "homozygous mutant" refers to a cell in which two or more copies (typically two in most eukaryotic cells, although certain filamentous yeasts, and some higher eukaryotic cell lines, may have more than two copies) of a given gene are mutated.

As used herein, "copies" of genes are also known in the art as "alleles". This latter term signifies the naturally-occurring copy of a given gene in a cell. Usually there are two copies of a gene in a diploid cell. In some situations (e.g., trisomy 21) there are three copies, but four or more copies of one or more entire chromosomes, or extra copies of genes or chromosomal fragments are also encountered naturally. Cells may also be experimentally altered to change the number or expression of specific genes.

The methods and the compositions of the invention may involve insertional mutagens that contain target nucleotide sequences for homologous recombination. As used herein a "target sequence" allows homologous recombination of an insertional mutagenic nucleotide with cellular DNA at a predetermined site on the cellular DNA, the site having homology for sequences in the insertional mutagen, the homologous recombination at the predetermined site resulting in the introduction of the insertional mutagen into the genome and subsequent mutation. A target sequence may have homology to the sequence or sequences within the gene to be mutated or upstream or downstream of the gene to be mutated. The use of targeting sequences has been disclosed in many U.S. patent applications, including U.S. Pat. Nos. 5,641,670, 6,270,989, and 5,733,761, all incorporated by reference for teaching a target sequence.

As used herein, "non-homologous recombination" (which may also be referred to equivalently as "illegitimate recombination") means the joining (exchange or redistribution) of genetic material through a mechanism that does not involve homologous recombination (e.g., recombination directed by targeting sequences) and that does not involve site-specific recombination (e.g., recombination directed by site-specific recombination signals and a corresponding site-specific recombinase). Examples of non-homologous recombination include integration of exogenous DNA into chromosomes at non-homologous sites, chromosomal translocations and deletions, DNA end joining, double strand break repair, bridge-break-fusion, concatemerization of transfected polynucleotides, retroviral insertion, and transposition. In most cases, non-homologous recombination is thought to occur through the joining of "free DNA ends." Free ends are DNA molecules that contain an end capable of being joined to a second DNA end either directly, or following repair or processing. The DNA end may consist of a 5' overhang, 3' overhang, or blunt end. Non-homologous recombination methods have been discussed in U.S. Pat. Nos. 6,410,226 and 6,361,972, herein incorporated by reference for teaching non-homologous recombination.

Retroviral vectors integrate into eukaryotic genomes by a distinct mechanism of non-homologous recombination that is catalyzed by the action of the virally encoded integrase enzyme, and the mechanism of viral integration, replication and infection has been well described (reference 0). The mutagenic ability of retroviruses and retroviral vectors and their ability to enable the rapid identification of mutated genes through the linkage of retroviral tag sequences within the transcripts of mutagenized genes are well known in the art (reference 2-5).

General reference for mechanisms of retroviral infection, replication, and integration: 0: In: *Retroviruses*. Coffin, J M.; Hughes, S H.; Varmus, H E. Plainview (N.Y.): Cold Spring Harbor Laboratory Press; c1997; Use of wildtype retroviruses as mutagens: 1: Varmus H E, Quintrell N, Ortiz S. *Cell*. July 1981; 25(1):23-36; Use of retrovirus promoter traps as mutagens and to isolate trapped genes: 2: Friedrich G, Soriano P. *Methods Enzymol*. 1993; 225:681-701; 3: Gossler A, Joyner A L, Rossant J, Skarnes W C. *Science*. Apr. 28, 1989; 244(4903):463-5; 4: Friedrich G, Soriano P. *Genes Dev*. September 1991; 5(9):1513-23; 5: von Melchner H, DeGregori J V, Rayburn H, Reddy S, Friedel C, Ruley H E. *Genes Dev*. June 1992; 6(6):919-27; Randomness of retroviral insertion: 6: King W, Patel M D, Lobel L I, Goff S P, Nguyen-Huu M C. *Science*. May 3, 1985; 228(4699):554-8; 7: Hubbard S C, Walls L, Ruley H E, Muchmore E A. *J Biol Chem*. Feb. 4, 1994; 269(5):3717-24.

Like retroviruses, transposons and transposon vectors can also be used to integrate sequences that can act as insertional mutagens. Also like retroviruses, transposons integrate by enzymatically catalyzed non-homologous recombination in which transposase enzymes catalyze the genomic integration and transposition of transposon DNA (reference 1, 2, 12, 13). Numerous transposons have been characterized that function in insects (reference 13-15), plants (reference 16-20) and vertebrates (including mammals, reference 3-12). In particular, the TC1/mariner derivative transposon, Sleeping Beauty, has been demonstrated to integrate efficiently in mammals. Transposons have been shown to function as efficient insertional mutagens in numerous systems (reference 5, 15, 17, 24-26), and to exhibit broad target specificity (reference 21-23). Transposase catalyzes SB transposition and integration: 1: Cui Z, Geurts A M, Liu G, Kaufman C D, Hackett P B. *J Mol Biol*. May 17, 2002; 318(5):1221-35; 2: Izsvak Z, Khare D, Behlke J, Heinemann U, Plasterk R H, Ivics Z. *J Biol Chem*. Jun. 24, 2002 SB transposon can transpose and act as an insertional mutagen in mammals: 3: Dupuy A J, Clark K, Carlson C M, Fritz S, Davidson A E, Markley K M, Finley K, Fletcher C F, Ekker S C, Hackett P B, Horn S, Largaespada D A. *Proc Natl Acad Sci USA*. Apr. 2, 2002; 99(7):4495-9; 4: Horie K, Kuroiwa A, Ikawa M, Okabe M, Kondoh G, Matsuda Y, Takeda J. *Proc Natl Acad Sci USA*. Jul. 31, 2001; 98(16):9191-6; 5: Dupuy A J, Fritz S, Largaespada D A. *Genesis*. June 2001; 30(2):82-8; 6: Fischer S E, Wienholds E, Plasterk R H. *Proc Natl Acad Sci USA*. Jun. 5, 2001; 98(12): 6759-64; 7: Ivics Z, Hackett P B, Plasterk R H, Izsvak Z. *Cell*. Nov. 14, 1997; 91(4):501-10. Other transposons also function in mammals: 8: Zagoraiou L, Drabek D, Alexaki S, Guy J A, Klinakis A G, Langeveld A, Skavdis G, Mamalaki C, Grosveld F, Savakis C. *Proc Natl Acad Sci USA*. Sep. 25, 2001; 98(20):11474-8; 9: Sherman A, Dawson A, Mather C, Gilhooley H, Li Y, Mitchell R, Finnegan D, Sang H. *Nat Biotechnol*. November 1998; 16(11):1050-3; 10: Kawakami K, Shima A, Kawakami N. *Proc Natl Acad Sci USA*. Oct. 10, 2000; 97(21):11403-8; 11: Fadool J M, Hartl D L, Dowling J E. *Proc Natl Acad Sci USA*. Apr. 28, 1998; 95(9):5182-6; 12: Plasterk R H. *Cell*. Sep. 10, 1993; 74(5):781-6. P elements developed as insertional mutagen in invertebrates: 13: Kaufman P D, Rio D C. *Nucleic Acids Res*. Nov. 25, 1991; 19(22): 6336; 14: Rubin G M, Spradling A C. *Nucleic Acids Res*. Sep. 24, 1983; 11(18):6341-51; 15: Spradling A C, Rubin G M. *Science*. Oct. 22, 1982; 218(4570):341-7. Ac and Ds and other plant transposons transpose, integrate and are used as insertional mutagens in plants: 16: Grevelding C, Becker D, Kunze R, von Menges A, Fantes V, Schell J, Masterson R. *Proc Natl Acad Sci USA*. Jul. 1, 1992; 89(13):6085-9; 17: Walbot V. *Curr Opin Plant Biol*. April 2000; 3(2):103-7; 18: Pereira A, Aarts M G. *Methods Mol Biol*. 1998; 82:329-38; 19: Cooley M B, Goldsbrough A P, Still D W, Yoder J I. *Mol Gen Genet*. Aug. 27, 1996; 252(1-2):184-94; 20: Bhatt A M, Page T, Lawson E J, Lister C, Dean C. *Plant J*. June 1996; 9(6):935-45. P element transposon can integrate broadly throughout genomes: 21: Kassis J A, Noll E, VanSickle E P, Odenwald W F, Perrimon N. *Proc Natl Acad Sci USA*. Mar. 1, 1992; 89(5):1919-23; 22: Berg C A, Spradling A C. *Genetics*. March 1991; 127(3):515-24; 23: Tower J, Karpen G H, Craig N, Spradling A C. *Genetics*. February 1993; 133(2):347-59; 24: Cooley L, Berg C, Kelley R, McKearin D, Spradling A. *Prog Nucleic Acid Res Mol Biol*. 1989; 36:99-109; 25: Cooley L, Kelley R, Spradling A. *Science*. Mar. 4, 1998; 239(4844): 1121-8; 26: Spradling A C, Stern D M, Kiss I, Roote J, Laverty T, Rubin G M. *Proc Natl Acad Sci USA*. Nov. 21, 1995; 92(24):10824-30.

As used herein, the term "phenotype" means any property of a cell or organism but may not refer simply to a change in expression of an mRNA or protein. Examples of phenotypes include, but are in no way limited to, cellular, biochemical, histological, behavioral, or whole organismal properties that can be detected by the artisan. Phenotypes include, but are not limited to, cellular transformation, cell migration, cell morphology, cell activation, resistance or sensitivity to drugs or chemicals, resistance or sensitivity to pathogenic protein localization within the cell (e.g. translocation of a protein from the cytoplasm to the nucleus), profile of secreted or cell surface proteins, (e.g., bacterial or viral) infection, post-translational modifications, protein localization within the cell (e.g. translocation of a protein from the cytoplasm to the nucleus), profile of secreted or cell surface proteins, cell proliferation, signal transduction, metabolic defects or enhancements, transcriptional activity, cell or organ transcript profiles (e.g., as detected using gene chips), apoptosis resistance or sensitivity, animal behavior, organ histology, blood chemistry, biochemical activities, gross morphological properties, life span, tumor susceptibility, weight, height/length, immune function, organ function, any disease state, and other properties known in the art. In certain situations and therefore in certain embodiments of the invention, the effects of mutation of one or more genes in a cell or organism can be determined by observing a change in one or more given phenotypes (e.g., in one or more given structural or functional features such as one or more of the phenotypes indicated above) of the mutated cell or organism compared to the same structural or functional feature(s) in a corresponding wildtype or (non-mutated) cell or organism (e.g., a cell or organism that in which the gene(s) have not been mutated).

As used herein, the term "multiploid" means any ploidy greater than haploid. Multiploid encompasses diploid, triploid, tetraploid, and aneuploid.

As used herein "library" means more than one clone. A library may be cells subjected to mutagenesis methods, singly or more than one time. Thus a library includes, but is not limited to, two or more clones of mutated cells or mutated cells where each cell has a different set of mutations. Libraries provide a source of cells to subject to mutagenesis and a source of cells to screen for desired phenotypes following mutagenesis.

A "known" gene is directed to the level of characterization of a gene. The invention allows expression of genes that have been characterized, as well as expression of genes that have not been characterized. Different levels of characterization are possible. These include detailed characterization, such as cloning, DNA, RNA, and/or protein sequencing, and relating the regulation and function of the gene to the cloned sequence (e.g., recognition of promoter and enhancer sequences, functions of the open reading frames, introns, and the like). Characterization can be less detailed, such as having mapped a gene and related function, or having a partial amino acid or nucleotide sequence, or having purified a protein and ascertained a function. Characterization may be minimal, as when a nucleotide or amino acid sequence is known or a protein has been isolated but the function is unknown. Alternatively, a function may be known but the associated protein or nucleotide sequence is not known or is known but has not been correlated to the function. Finally, there may be no characterization in that both the existence of the gene and its function are not known. The invention allows expression of any gene at any of these or other specific degrees of characterization.

Overview

The ability to create tagged mutations in multiple genes in multiploid cells and multicellular organisms would have utility in many areas, including correlating a phenotype with the genes responsible for it by gene identification, gene discovery, determining gene function, creating phenotypes, discovering drug targets, and making human disease models in cells and in multicellular organisms.

The ability to create tagged homozygous mutations in a cell or multicellular organism enables alteration of the genetic make up of a cell and has numerous uses, such as those above as well as correcting genetic defects. The in vitro, ex vivo, and in vivo potential uses of this technology are enormous and will be readily apparent to the skilled artisan.

The present invention, therefore, is directed to methods for mutating a single gene or multiple genes (e.g., two or more) in cells and multicellular organisms. The invention also is directed to insertional mutagens for making the mutant cells and organisms, and which also can be used to analyze the mutations that are made in the cells and organisms. The invention also is directed to methods in which one or more mutated genes is tagged by a tag provided by the insertional mutagen to allow the detection, selection or screening, isolation, and manipulation of a cell with a genome tagged by the insertional mutagen and allows the identification and isolation of the mutated gene(s).

The invention provides methods for making multiple mutations (i.e., mutations in two or more genes that produce a phenotype cumulatively) in cells and organisms and tagging at least one of the mutated genes such that it can be rapidly recovered and identified. Creation of multiple mutations in a cell where at least one of the mutations is tagged is useful in studying gene function. One reason for this is that many phenotypes require multiple gene mutations in order to be manifested. Current methods do not allow for creation of multiple mutations in a cell in a manner that allows easy identification of the mutated genes. The present invention enables multiple mutations to be created in the same cell and allows at least one of the mutations to be tagged.

Libraries that contain the cells mutagenized by insertional mutagenesis can be screened or selected for a phenotype of interest. In cells that have the phenotype of interest, one or more tagged genes can be identified and validated as being responsible for the particular phenotype of interest.

The invention also provides methods for making homozygous mutations in eukaryotic cells and organisms. The homozygously mutated gene is tagged by an insertional mutagen so that it can be identified and, if desired, recovered. Homozygous mutations are useful for discovering functions associated with the mutated gene.

Although the methods of the invention identify a mutated gene, the invention provides a way to correlate the gene with a function and thus provides a way to ascribe a function to the wildtype gene and to use that wildtype gene and gene product. The invention, therefore, provides for use of the wildtype gene or other natural variant of the gene that is identified as described above. This includes, but is not limited to, allelic variants, homologs, orthologs, pseudogenes, and the like. The wildtype gene, that has been identified by means of the mutated version, as well as other variants, can be isolated, for example, from non-mutated cells, using standard recombinant DNA or molecular biological techniques, such as cDNA library screening or PCR. The wildtype gene/protein or other variant can be used, for example, as a therapeutic protein or antibody target. Naturally-occurring mutants are also useful as therapeutic or diagnostic targets, for example, with antibodies or other detectable and/or inhibiting binding reagents.

In a diseased tissue or cell, a naturally-occurring mutant gene gives rise to the disease. Further mutation by the present method can revert the cell or organism to a normal phenotype allowing identification of the mutated disease gene or other genes that, when mutated, restore the cell to a normal phenotype. These genes can also provide drugs or drug targets.

One goal of the present invention is to mutate each gene in combination with at least one other gene in the same cell, and collectively in a library of cells, to mutate each gene in combination with every other gene. Another goal is to mutate both alleles (in the same cell) of endogenous genes without the use of gene sequence information. Another goal is to mutate both alleles (in the same cell) of substantially all genes in a host cell genome. In one embodiment of the invention, another goal is to mutate each expressed gene in combination with every other expressed gene. Accordingly, a further goal is to mutate both alleles of substantially all expressed genes in a host cell genome and all expressed genes that are members of a set of genes that are cumulatively required to be mutated to produce a phenotype.

Libraries produced according to the methods of the invention are generally produced as follows. A plurality of cells, generally in the range, for example, of $10^6$-$10^8$ (retrovirus infection) and $10^8$-$10^{10}$ (transfection) are subjected to insertional mutagenesis events to produce a plurality of cells with a mutation in one allele of every gene that requires a homozygous mutation in order to manifest a phenotype. Such insertion events can be produced by a single vector or different vectors simultaneously or sequentially. At any stage following introduction of an insertional mutagen, cells can be screened or selected for mutation of a specific desired gene or for a desired phenotype. Cells manifesting a phenotype may be further explored or discarded if they contain dominant mutations. Cells could also be screened or selected for incorporation of the insertional mutagen to which they were exposed following any or all exposures to an insertional mutagen. Cells having desired phenotypes or containing an insertional mutagen can be isolated and cloned at any stage in library production.

To produce and identify one or more homozygous mutations in the library, a different insertion vector is exposed to the cells. The insertion of this vector into the second allele of a gene allows the identification of that gene. Optimally, only one gene per cell is mutated with the second insertional mutagen. After exposure to the second insertional mutagen (which can be repeated), cells can be screened or selected for the mutation of a specific desired gene or for a desired phenotype. Cells having the phenotype can then be isolated and cloned and the gene causing the phenotype can be identified by means of the second insertional mutagen. After exposure to the second insertional mutagen, cells can also be screened or selected for having the second insertional mutagen incorporated. The ability to select or screen cells that contain both the first and second insertional mutagens provides a way to decrease background. Using different insertional mutagens facilitates the identification of the gene associated with a homozygous mutation against a background of cells containing insertions that cause heterozygous mutations.

Similarly, when the object is to produce a library containing cells having multiple mutations in genes where the mutations are cumulatively required to produce a phenotype, cells in the library are mutagenized by a first insertional mutagen that creates a substantial number of mutations so that in the case in which mutations in a set of genes are required to produce a phenotype, the mutation level provides cells in which less than all of the genes of the set is mutated. Preferentially, one more gene is required per set. Insertional mutagenesis with a different insertional mutagen completes mutation of the set of genes and allows the identification of a gene in the set. Prior to adding the insertional mutagen that mutates the last gene in the set, any number of insertional mutagenesis events can be applied and one or more different insertional mutagens can also be applied. Cells can be screened or selected for mutation of a desired gene or for a desired phenotype after any exposure to an insertional mutagen. Cells having a phenotype may be further explored or may be discarded so that the remaining cells in the library do not have the phenotype. Furthermore, cells can be screened or selected after each exposure for an incorporated insertional mutagen so that they can be selected and the background of the library (i.e., cells not containing insertional mutagens) can be reduced. Any selected cell can be isolated and cloned and can be subjected to further mutagenesis and screening or selection.

Accordingly, the process can include the following events:

1. expose to mutagen (one or more times)
2. screen or select for desired gene or phenotype
3. screen or select for insertion.

2 and 3 can precede or follow each other and one or both can be performed after every exposure to a mutagen. Further, cells can be isolated and/or cloned following or prior to any performance of 1, 2 or 3 although this is optional. Thus, 1, 2 and 3 can be performed on isolated and/or cloned cells if desired.

In one embodiment of the invention, a library of mutated cells is created by inserting one or more insertional mutagens into the genome of a host cell under conditions allowing two or more mutations per cell. In preferred embodiments, the library contains a sufficient number of clones to produce a homozygous mutation in at least one endogenous gene.

The library may be screened or selected for cells displaying a desired phenotype.

Optionally, cells displaying a desired phenotype can be isolated.

Optionally, the mutated gene responsible for the phenotype can be identified.

Preferably the mutagen is a gene disruption vector.

In another embodiment of the invention, a library of cells is created by introduction of two or more different insertional mutagens into the genome of each cell.

The library can be screened or selected for mutation of a desired endogenous gene. Alternatively, the library can be screened or selected for cells displaying other desired phenotypes.

Optionally, cells containing a specific mutated gene or displaying a desired phenotype may be isolated.

Optionally, the mutated gene responsible for the phenotype can be identified.

Preferably the mutagen is a gene disruption vector.

In another embodiment of the invention, a first insertional mutagen is introduced into one or more cells. The cells containing the first insertional mutagen are then expanded such that each clone contains a larger number of cells. A second insertional mutagen is then inserted into the genome of the cells containing the first mutagen.

The library can be screened or selected for mutation of a desired endogenous gene. Alternatively, the library can be screened or selected for cells displaying other desired phenotypes.

Optionally, cells containing a specific mutated gene or displaying a desired phenotype can be isolated.

Optionally, the mutated gene responsible for the phenotype can be identified.

Preferably the mutagen is a gene disruption vector.

In another embodiment of the invention, a first insertional mutagen containing a selectable marker is introduced into one or more cells. The cells are then selected for integration of the first insertional mutagen integrated into the host cell genome. Cells, optionally, can be expanded such that each clone contains a larger number of cells. A second insertional mutagen is then inserted into the genome of the cells containing the first insertional mutagen. Optionally, the second insertional mutagen can contain a selectable marker and cells in which the second insertional mutagen has integrated into the genome can be selected.

The library can be screened or selected for mutation of a desired endogenous gene. Alternatively, the library can be screened or selected for cells displaying other desired phenotypes.

Optionally, cells containing a specific mutated gene or displaying a desired phenotype can be isolated.

Optionally, the mutated gene responsible for the phenotype can be identified.

Preferably the mutagen is a gene disruption vector.

In another embodiment of the invention, a first insertional mutagen containing a selectable marker lacking its own promoter is introduced into one or more cells. The cells containing the first insertional mutagen are then selected for mutation of a transcriptionally active gene. Cells, optionally, can be expanded such that each clone contains a larger number of cells. A second insertional mutagen is then inserted into the genome of the cells containing the first insertional mutagen. Optionally, the second insertional mutagen can contain a selectable marker lacking its own promoter and cells in which the second insertional mutagen has mutated a transcriptionally active gene can be selected.

The library can be screened or selected for mutation of a desired endogenous gene. Alternatively, the library can be screened or selected for cells displaying other desired phenotypes.

Optionally, cells containing a specific mutated gene or displaying a desired phenotype may be isolated.

Optionally, the mutated gene responsible for the phenotype can be identified.

Preferably the mutagen is a gene disruption vector.

The present invention is also directed to cells and libraries of cells produced by the present invention. The methods of the present invention can be used to mutate any cell.

The cells can be prokaryotic or eukaryotic cells. The cells can be derived from multi-cellular organisms.

The cells may be of vertebrate or invertebrate origin. The cells can be mammalian. The cells can be derived from any species. Examples of species include human, mouse, rat, avian, bovine, porcine, ovine, insect, plant (monocot or dicot), mold and fungal cells.

The methods of the present invention can be used to mutate any eukaryotic cell, including, but not limited to, haploid (in the case of multiple gene mutations), diploid, triploid, tetraploid, or aneuploid. In one embodiment, the cell is diploid. Cells in which the methods of the present invention can be advantageously used include, but are not limited to, primary cells (e.g, cells that have been explanted directly from a donor organism) or secondary cells (e.g., primary cells that have been grown and that have divided for some period of time in vitro, e.g., for 10-100 generations). Such primary or secondary cells can be derived from multi-cellular organisms, or single-celled organisms. The cells used in accordance with the invention include normal cells, terminally differentiated cells, or immortalized cells (including cell lines, which can be normal, established or transformed), and can be differentiated (e.g., somatic cells or germ cells) or undifferentiated (e.g., multipotent, pluripotent or totipotent stem cells).

Examples of tissues from which cells can be isolated for use in the present invention include, without limitation, neuronal tissue (including tissue from the central and peripheral nervous systems), hematopoietic tissue, lymphatic tissue, immune tissue, bone tissue, stromal tissue (including, e.g., bone marrow tissue), mesenchymal tissue, mesothelial tissue, connective tissue (including e.g., cartilage, dermal tissue, subcutaneous tissue, adipose tissue, etc.), endothelial tissue, epithelial tissue, lung tissue, skin tissue, kidney tissue, gastrointestinal tissue (including esophagus, stomach, intestine, etc.), brain tissue, heart tissue, pancreatic tissue, muscle tissue, liver tissue, gonadal tissue, embryonic tissue including embryonic stem cells and embryonic germ cells), zygote tissue, embryonic, and other cells and tissue known in the art.

A variety of cells isolated from the above-referenced tissues, or obtained from other sources (e.g., commercial sources or cell banks), can be used in accordance with the invention. Non-limiting examples of such cells include somatic cells such as blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used in accordance with the invention, as can the progenitors, precursors and stem cells that give rise to the above-described somatic and germ cells. These cells, tissues and organs can be normal, or they can be pathological such as those involved in diseases or physical disorders, including but not limited to infectious diseases (caused by bacteria, fungi or yeast, viruses (including HIV) or parasites), in genetic or biochemical pathologies (e.g., cystic fibrosis, hemophilia, Alzheimer's disease, schizophrenia, muscular dystrophy, multiple sclerosis, etc.), or in carcinogenesis and other cancer-related processes.

The eukaryotic cells used in the methods of the present invention can be animal cells, plant cells (monocot or dicot plants) or fungal cells, such as yeast. Animal cells include those of vertebrate or invertebrate origin. Vertebrate cells are of particular use in the present invention, especially mammalian cells (including, but not limited to, cells obtained or derived from human, simian or other non-human primate, mouse, rat, avian, bovine, porcine, ovine, canine, feline and the like), avian cells, fish cells (including zebrafish cells), insect cells (including, but not limited to, cells obtained or derived from *Drosophila* species, from *Spodoptera* species (e.g., Sf9 obtained or derived from *S. frugiperida*, or HIGH FIVE™ cells) or from *Trichoplusa* species (e.g., MG1, derived from *T. ni*)), worm cells (e.g., those obtained or derived from *C. elegans*), and the like. It will be appreciated by the ordinarily skilled artisan, however, that cells from any species besides those specifically disclosed herein can be advantageously used in accordance with the methods of the present invention, using art-known methods in conjunction with those described herein and without the need for undue experimentation.

Cell lines are also useful in the present invention. Examples of useful cell lines include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (see Van der Blick, A. M. et al., *Cancer Res.* 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171) can also be used. Other mammalian cells and cell lines can be used in accordance with the present invention, including but not limited to CHO cells, COS cells, VERO cells, 293 cells, PER-C6 cells, M1 cells, NS-1 cells, COS-7 cells, MDBK cells, MDCK cells, MRC-5 cells, WI-38 cells, WEHI cells, SP2/0 cells, BHK cells (including BHK-21 cells); these and other cells and cell lines are available commercially, for example from the American Type Culture Collection (P.O.Box 1549, Manassas, Va. 20108 USA). Many other cell lines are known in the art and will be familiar to the ordinarily skilled artisan; such cell lines therefore can be used equally well in the methods of the present invention.

The present invention can be practiced using plant cells. Methods for culturing plant cells, insertionally mutating plant cells, and producing transgenic plants are known in the art (see, e.g., Hall, Robert D., *Plant Cell Culture Protocols*, Humana Press, New Jersey (1999); Gartland and Davey, *Agrobacterium Protocols*, Humana Press, New Jersey (1995); each incorporated herein by reference for teaching methods of culturing, transfecting, mutating, and producing transgenic plants and plant cells).

In certain embodiments of the invention, cells can be mutated within the organism or within the native environment as in tissue explants (e.g., in vivo or in situ). Alternatively, tissues or cells isolated from the organism using art-known methods and genes can be mutated according to the present methods. The tissues or cells are either maintained in culture (e.g., in vitro), or re-implanted into a tissue or organism (e.g., ex vivo).

The invention also encompasses use of the mutated cells to produce transgenic animals.

Transgenic animals can be created from mutant somatic or germ cells, or from mutant stem cells (e.g., embryonic or adult stem cells), that have been produced by methods of the invention. Donor cells (which may be a somatic cell, an adult stem cell, a germ cell or an embryonic stem cell from a donor animal) are subjected to insertional mutagenesis in vitro to produce a mutated donor cell with a single homozygous mutation that produces a desired phenotype in the cell or organism or a mutated donor cell with mutations in multiple genes (that cumulatively will achieve a desired phenotype in the cell or organism). The animal can be made by transferring the nucleus from the donor cell to a recipient cell (which may be, for example, a fertilized oocyte that has been enucleated), and producing a transgenic organism from the recipient cell. Alternatively, the mutant stem cell could be implanted into a blastocyst or the mutant germ cell used to create a mutant zygote through in vitro fertilization or artificial insemination and the resulting mutant zygotes put into a pseudo-pregnant female to produce the transgenic organism.

Genetically modified animals can be created by transplantation of nuclei from cells that have been mutagenized by the techniques of the present invention. Nuclei extracted from mutant cells are then implanted into enucleated fertilized eggs, and the resultant zygote is implanted into a pseudopregnant female to develop into an animal carrying the mutations that were generated in the original mutagenized cell.

Zygotes can also be formed from mutant embryonic or other pluripotent stem cell following the blastocyst fusion protocols that have been developed for the creation of genetically modified mice.

Briefly, the modified stem cells are combined with cells of a diploid or tetraploid morula or the modified cells are injected directly into the blastocoel of a developing blastocyst. The chimeric zygote that results is implanted into a pseudopregnant female to develop into an animal carrying the mutations generated in the stem cell. Genetically modified germ cells can be created by in vitro retroviral-mediated or other gene delivery into spermatogonial stem cells of both adult and immature animals and can result in stable integration of the insertional mutagen in 2-20% of stem cells. After transplantation of the transduced stem cells into the testes of infertile recipient animals, approximately 4.5% of progeny from these males contain the insertional mutagen, and this mutagenic vector is transmitted to and functions in subsequent generations. 1: Chesne P, Adenot P G, Viglietta C, Baratte M, Boulanger L, Renard J P. *Nat Biotechnol*. April 2002; 20(4):366-9; 2: Hosaka K, Ohi S, Ando A, Kobayashi M, Sato K. *Hum Cell*. December 2000; 13(4):237-42; 3: Wolf E, Zakhartchenko V, Brem G. *Biotechnol*. Oct. 27, 1998; 65(2-3):99-110.; In Hogan B, Beddington R, Costantini F, Lacy E. *Manipulating the Mouse Embryo; a Laboratory Manual* Cold Spring Harbor Laboratory Press. 1994; 1: Cecconi F, Gruss P. Methods *Mol Biol*. 2002; 185:335-46. Review; 1: Brinster R L. *Science*. Jun. 21, 2002; 296(5576): 2174-6; 2: Nagano M, Brinster C J, Orwig K E, Ryu B Y, Avarbock M R, Brinster R L. *Proc Natl Acad Sci USA*. Nov. 6, 2001; 98(23):13090-5; 1: Cecconi F, Gruss P. *Methods Mol Biol*. 2002; 185:335-46.

In another embodiment, transgenic organisms can be created from cells chosen because they display a desired phenotype in vitro after being subjected to insertional mutagenesis according to the methods of the invention. The identity of the gene or genes responsible for the phenotype may or may not be known at this stage for the preparation of transgenic animals. In another embodiment transgenic organisms can be created from a cell with a mutation in a specific desired gene. In another embodiment, mutated cells can be chosen at random, used to make the transgenic organism, and the transgenic organism can be screened for a desired phenotype.

The invention also encompasses methods for making transgenic animals and transgenic animals produced by the present methods. Transgenic animals that can be produced by the methods of the invention include, for example, insects (including Drosophila, Spodoptera and Trichoplusa species), birds, worms (including *C. elegans*), fish (including zebrafish), mammals (including humans, and non-human mammals such as simians and other non-human primates, mice, rats, pigs, cows, sheep, dogs, cats, and the like). The transgenic animals can be used, for example, as models for human disease, to study gene function, to screen for phenotypes of interest, for agricultural applications, or for drug testing.

The invention also provides methods of producing transgenic plants, and transgenic plants produced by such methods. Transgenic plants that can advantageously be produced according to such methods include dicotyledonous and monocotyledonous plants.

The present invention is also directed to cell libraries containing a number of clones useful for producing homozygous gene disruptions.

The number of clones in the library containing two insertional mutations depends on the size of the genome of the host cell, its ploidy, gene structure, the average insertion window associated with gene disruption (e.g. size of the gene), the amount of genome coverage that is desired (i.e. % of genes that are insertionally mutated), the number of genes capable of producing a desired phenotype when mutated, and whether the clones in the library have been selected or screened for vector insertion into endogenous genes (i.e., gene traps). Since genome sizes vary among species, it is possible to rely on general guidelines for determining the number of insertions to create a library.

As a general guideline for libraries that are produced without selection or screening for gene trap events, an estimate of a useful number of clones in the library containing two insertions per cell can be determined by the following equation:

$$X=[(\text{size of the host cell genome in base pairs})/10,000]^2;$$

where X is the number of clones that contain 2 or more insertional mutagens.

Typically, the number of clones in the library is at least 0.01X. In preferred embodiments, the number of clones in the library is at least 0.1X, and more preferably at least 1X. In highly preferred embodiments, the number of clones in the library is at least 10X, and often 100X or more.

It is understood, however, that the number of clones in the library can be reduced by selection for gene traps following insertion of the first mutagen, following the insertion of the second mutagen, or following the insertion of the first and the second mutagen. This will reduce the number of clones needed to mutate each gene. The magnitude of reduction in the number of clones depends upon the ratio of gene coding sequences to non-coding sequences in the genome of the host cell and the type of gene trap vector used. In general, a larger ration of non-coding sequence to coding sequence will result in a larger reduction in the number of clones in the library following selection. In mammalian cells, use of gene trap vectors such as the vector described in FIG. 4B will result in a reduction in library size of approximately 100-fold when selection is carried out for two independent gene trap events (e.g., selection or screening for gene traps resulting from the insertion of the first mutagen and selection or screening for gene traps resulting from the insertion of the second mutagen).

Another equation useful in estimating library size is:

$$Y = (\text{\# of genes in host cell genome})^2;$$

where Y is the number of clones that contain 2 or more insertional mutagens.

By this equation, the number of clones in the library is typically at least 0.01Y. In preferred embodiments, the number of clones in the library is at least 0.1Y, and more preferably at least 1Y. In highly preferred embodiments, the number of clones in the library is at least 10Y, and often 100Y or more.

It is understood, however, that the number of clones in the library can be reduced by selection or screening for gene traps following insertion of the first mutagen, following the insertion of the second mutagen, or following the insertion of the first and the second mutagen. This will reduce the number of clones needed to mutate each gene. The magnitude of reduction in the number of clones depends upon the ratio of gene coding sequences to non-coding sequences in the genome of the host cell and the type of gene trap vector used. In general, a larger ration of non-coding sequence to coding sequence will result in a larger reduction in the number of clones in the library following selection. In mammalian cells, use of gene trap vectors such as the vector described in figure X will result in a reduction in library size of approximately 100-fold when selection is carried out for two independent gene trap events (e.g., selection for gene traps resulting from the insertion of the first mutagen and selection for gene traps resulting from the insertion of the second mutagen).

In higher eukaryotic organisms, the genome is typically large. In mouse and human cells, for example, the haploid genome is estimated to be 3,000,000,000 base pairs (6 billion bps for the diploid genome). Statistically, to create a library in which each vector is integrated, on average, once every 10,000 pase pairs, 300,000 clones ($3 \times 10^9 / 10,000$) are required for one vector integrated per cell, and $(300,000)^2$ or $9 \times 10^{10}$ clones are required for two vectors per cell.

A useful number of clones in a library can also be determined empirically. For example, a library of mutated clones can be created and tested for mutation of one or more known genes. The mutation frequency of a known gene can be used to estimate library coverage (i.e. the percentage of genes that have been mutated in the library). For example, if one allele of a known gene is mutated at a frequency of $1/10^6$ clones, then the artisan can predict that the number of clones useful to mutate both alleles of the known gene in the same cell would be $(10^6)^2$ or $10^{12}$ clones. A library containing fewer clones could be used; however, the probability of mutating both alleles of a gene would be reduced. Likewise, if a library containing more clones were produced, then the higher probability of mutating both alleles of a gene would be increased. Thus, empirical determination of mutation rates for one or more test genes can be used to determine or evaluate library clone numbers. Selection or screening for gene traps following insertion of the first mutagen, following the second mutagen, or following both, will reduce the library size.

It is understood, however, that the number of clones in the library can be reduced by selection or screening for gene traps following insertion of the first mutagen, following the insertion of the second mutagen, or following the insertion of the first and the second mutagen. This will reduce the number of clones needed to mutate each gene. The magnitude of reduction in the number of clones depends upon the ratio of gene coding sequences to non-coding sequences in the genome of the host cell and the type of gene trap vector used. In general, a larger ration of non-coding sequence to coding sequence will result in a larger reduction in the number of clones in the library following selection. In mammalian cells, use of gene trap vectors such as the vector described in figure X will result in a reduction in library size of approximately 100-fold when selection is carried out for two independent gene trap events (e.g., selection for gene traps resulting from the insertion of the first mutagen and selection for gene traps resulting from the insertion of the second mutagen).

One method for assessing mutation frequency is to test for gene function of a selectable or screenable marker within the cell. Typically, the marker exists in the cells as a single copy gene; however, multi-copy genes could be useful, particularly to assess high mutation frequencies. The marker gene can be a cellular gene, such as HPRT, or could be an exogenously introduced gene, such as HSV-Thymidine Kinase, green fluorescent protein, luciferase, or a cell surface protein suitable for FACS sorting. Following mutagenesis, the artisan can assay for the absence of marker gene expression or activity. For example, mutation frequency can be assessed in mutagenized cells by selecting against HPRT or HSV-TK using selection with 6-Thioguanine (6-TG) and 1,2'-deoxy-2'-fluoro-β-D-arabinofuranosyl-5-iodouracil (FIAU), respectively. The number of surviving clones divided by the total number of clones plated defines the mutation frequency for single copy genes. Thus, a desired mutation frequency can be obtained in any cell by mutagenizing cells under several conditions, assaying for marker activity, and determining mutation frequency. With respect to the other marker examples descried above, and those known in the art, any suitable assay can be used to test for loss of marker function (or gain of function) including enzyme assays, ELISA, and FACS. Once a desired level of mutation in a cell population is obtained, one or more cells from that population can be used for further insertional mutagenesis to achieve homozygous mutation or mutation in multiple genes.

Another method for assessing mutation frequency involves screening for mutation of specific genes using PCR amplification. In this embodiment, the library can be separated into pools of clones (e.g. 1000 clones per pool). cDNA can be produced from the cells in each pool. Detection of specific disrupted genes can then be carried out by PCR using a vector specific primer and a gene specific primer. If a cell is producing a vector disrupted mRNA from a specific gene, then PCR amplification product will be produced. The number of pools containing a specific disrupted gene divided by the number of clones tested equals the mutation frequency for that gene. This information can be used to assess the coverage of the library. A variety of permutations of this assay are possible and would be recognized by a person of skill in the art. Thus, this assay can be used to select mutagenesis conditions that give rise to a desired mutation frequency.

The mutation frequency can be assessed after a first and a second gene disruption vector are introduced into each cell. In embodiments in which a first gene disruption vector and a second gene disruption vector are introduced into cell sequentially, the mutation frequency can be assessed following the integration of the first vector and/or following the integration of the second vector.

It should be understood that the above methods for estimating library size are useful for determining the number of cells in a library that have two or more insertional mutations.

It should also be understood that the number of clones in a library can be reduced by including marker genes on the gene disruption vectors to allow selection or screening for integration into (a) any location in the genome (b) any gene (c) transcriptionally active genes or (d) transcriptionally silent genes.

In practice, some insertional mutagens (e.g., retroviruses and transposons) show a bias for insertional mutagenesis of genes that are potentially active in the mutagenized cell. Accordingly, $10^4$-$10^5$ 5' gene trap insertions may be sufficient to cumulatively disrupt one allele of all active genes within the population of insertionally-mutagenized cells. Subsequent insertional mutagenesis to disrupt the other alleles needed to create a phenotype by homozygous or trans-heterozygous gene disruption would entail generation of an additional $10^4$-$10^5$ 5' gene trap alleles in each clone of the original insertionally-mutagenized library. With one gene per cell disrupted by each round of insertional mutagenesis, this would require generation of a cumulative library of $10^8$-$10^{10}$ members for genome-wide coverage. Increasing the number of gene trap gene disruptions per cell will proportionately decrease the size of the insertionally-mutagenized cell library that is needed for genome-wide coverage.

In embodiments where the vector contains a selectable marker or reporter gene, cells can be selected or screened for vector integration into the genome by selecting for (or against) expression of a marker gene. If the vector contains a promoter operably linked to a selectable marker and polyadenylation signal (see, for example, FIG. 7), then any cell containing an integrated vector can be recovered. If the vector contains a promoter operably linked to a selectable marker lacking a polyadenylation signal (see, for example, FIG. 5), then any cell containing a vector integrated into or upstream of an endogenous gene can be recovered following selection. If the vector contains a positive selectable marker that is not expressed from a vector encoded promoter, but instead relies on integration downstream of an endogenous promoter for its expression (see FIGS. 2-6 for examples), then any cell containing the vector integrated into a transcriptionally active gene can be recovered following selection. Integration into transcriptionally active genes is desirable because in instances where the cells are going to be screened or selected for a phenotype, disruption of a transcriptionally active gene is more likely to give a phenotype than disruption of a transcriptionally inactive gene. If the vector contains a negative selectable marker that is not expressed from a vector encoded promoter, but instead relies on integration downstream of an endogenous promoter for its expression (see FIGS. 2-6 for examples), then any cell containing the vector integrated into a transcriptionally silent gene or region can be recovered following selection. Selection against a transcriptionally active gene can be useful for removing cells that have insertionally mutated a transcriptionally active gene so that other genes can be studied. For example, after removing cells containing disrupted transcriptionally active genes, cells can be treated with agents that cause a change in gene expression within the cell and the artisan can now look for phenotypes that result from mutation of genes that were previously silent but now active. Reporter genes can also be used to screen for vector integration into the genome and, optionally, into transcriptionally active genes.

Libraries of cells containing two or more gene disruption vectors can be produced using a variety of strategies.

In one embodiment, a gene disruption vector is introduced into one or more host cells under conditions suitable for multiple vector integrations per cell. The number of clones containing two or more copies of the gene disruption vector can range from 1 clone to over $10^{12}$ clones depending on the size of the host cell genome, the intended use of the library, and other parameters discussed above. As an example, the number of mammalian cell clones containing two copies of the gene disruption vector is typically at least $10^8$, and more preferably at least $10^9$, more preferably $10^{10}$, and most preferably at least $10^{11}$. Optionally, the cells can be selected or screened for vector insertion into or disruption of any gene, any transcriptionally active gene, or any transcriptionally silent gene. The library can be screened or selected for mutation of a gene of interest or for a phenotype that results from mutation of a gene of interest. The mutant cell may be cloned or isolated.

Cells having mutation in active genes can be selected after exposure to a mutagen by means of a functional sequence on the mutagen that can only be expressed if the mutagen integrates in an active gene. One example is a selectable or screenable marker that cannot be transcribed unless it becomes operably-linked to an endogenous promoter in an active gene. The ability to select or screen for cells with mutations in genes significantly reduces the background of non-productive insertions (i.e. into non-genic regions that constitute the majority of the genome). When multiple insertional mutagens are used, each insertional mutagen can comprise a different selectable or screenable marker so that cells can be identified that have mutations in multiple genic regions.

In another embodiment, a first gene disruption vector is integrated into the genome of a cell. Optionally, the clone of cells containing an integrated vector can be screened for disruption of a desired gene. The clone of cells is expanded to produce additional cells for insertion of a second vector. A second gene disruption vector is then integrated by non-homologous recombination into the genome of the expanded cells. Each clone within this library contains a first gene disruption vector integrated at the same location in every host cell genome and a second gene disruption vector integrated at a different location in every host cell genome. The number of clones containing the second vector integrated at a unique location in the genome can vary according to the size of the host cell genome and other parameters discussed above. For mammalian cells, the number of clones, typically ranges between $10^3$-$10^7$, and often between $10^4$ and $10^5$. Optionally, the cells can be selected or screened for vector insertion into or disruption of any gene, any transcriptionally active gene, or any transcriptionally silent gene. The library can be screened or selected for mutation of a gene of interest or for a phenotype that results from mutation of a gene of interest. The mutant cell may be cloned or isolated.

In another embodiment, a first insertional mutagen is integrated into more than one cell to produce a library of cells, each cell containing the first gene disruption vector integrated at a different location in the host cell genome. The library of cells containing the first gene disruption vector can be expanded. Once expanded, a second gene disruption vector is integrated into the host cell genome of the cells containing the first gene disruption vector to produce a library of cells containing a first gene disruption vector and a second gene disruption vector. Within this library, each clone of cells contains a different combination of insertion sites for the first and second vectors. The number of clones containing the first vector can range from 1 clone to over 10,000,000 clones depending on the size of the host cell genome, the intended use of the library, and other parameters discussed above. In mammalian cells, the number of clones containing a first gene disruption vector is typically at least $10^5$ and more preferably at least $10^6$. Following expansion, a second gene disruption vector is introduced into the clones containing the first vector to produce a much larger library. The number of clones containing the second vector can vary according to the size of the host cell genome and other parameters discussed above. In mammalian cells, the number of clones containing a first gene disruption vector and a second gene disruption vector is typically at least $10^8$, more preferably at least $10^9$, and most preferably at least $10^{10}$. Optionally, the cells can be selected or screened for vector insertion into or disruption of any gene, any transcriptionally active gene, or any transcriptionally silent gene. The library can be screened or selected for mutation of a gene of interest or for a phenotype that results from mutation of a gene of interest. The mutant cell may be cloned or isolated.

In another embodiment, a first gene disruption vector containing a marker gene is integrated into the genome of one or more cells. The number of clones containing the first vector can range from 1 clone to over 10,000,000 clones depending on the size of the host cell genome, the intended use of the library, and other parameters discussed above. In mammalian cells, the number of clones containing a first gene disruption vector is typically at least $10^5$, and more preferably at least $10^6$. Following integration into the host cell genome, cells are placed under selection to recover cells that contain the first vector integrated into the host cell genome. The cells recovered from selection are then expanded. Following expansion, a second gene disruption vector is integrated into the genome of the cells. The number of clones containing the second vector can vary according to the size of the host cell genome and other parameters discussed above. In mammalian cells, the number of clones containing a first gene disruption vector and a second gene disruption vector is typically at least $10^8$, more preferably at least $10^9$, and most preferably at least $10^{10}$. Optionally, the cells can be selected or screened for insertion of the second vector or for disruption of transcriptionally active genes by the second vector. The library can be screened or selected for mutation of a gene of interest or for a phenotype that results from mutation of a gene of interest. The mutant cell may be cloned or isolated.

The insertional mutagens used in the present invention can comprise any nucleotide sequence capable of altering gene expression levels or activity of a gene product upon insertion into DNA that contains the gene. The insertional mutagens can be any polynucleotide, including DNA and RNA, or hybrids of DNA and RNA, and can be single-stranded or double-stranded, naturally occurring or non-naturally occurring (e.g, phosphorothioate, peptide-nucleic acids, etc.). The insertional mutagens can be of any geometry, including but not limited to linear, circular, coiled, supercoiled, branched, hairpin, and the like, and can be any length capable of facilitating mutation, and tagging of an endogenous gene. Typically, the insertional mutagens are at least 5 nucleotides in length, at least 10 nucleotides in length, at least 15 nucleotides in length, at least 20 nucleotides in length, at least 25 nucleotides in length, at least 50 nucleotides in length, at least 100 nucleotides in length, at least 200 nucleotides in length, at least 250 nucleotides in length, at least 500 nucleotides in length, at least 1000 nucleotides (e.g., at least 1 kb) in length, etc. In some embodiments of the invention, the insertional mutagens can be at least 1 kb in length, at least 2 kb in length, at least 2.5 kb in length, at least 5 kb in length, at least 7.5 kb in length, at least 10 kb in length, or larger. Preferably, the insertional mutagens at least 10-15 nucleotides in length. This length allows the artisan to use nucleotide primers complementary to the inserted polynucleotide to be used to make primer extension products of the insertionally mutated gene to detect or characterize (e.g., sequence) the gene.

In certain embodiments of the invention, the insertional mutagens can comprise one or more nucleotide sequences that provide a desired function. Such nucleotides sequences include, but are not limited to, one or more multiple cloning sites, one or more transcription termination sites, one or more transcriptional regulatory sequences (e.g., one or more promoters, enhancers, or repressors), one or more sequences that encode translational signals, one or more open reading frames (ORFs), one or more sequences mutating ORFs, one or more stop codons, one or more sequences mutating or eliminating stop codons, one or more mRNA destabilizing elements, one or more RNA stabilizing elements, one or more sequences that result in the formation of hairpin loops, one or more sequences that disrupt or eliminate hairpin loops, one or more reporter genes, one or more splice acceptor sequences, one or more splice donor sequences, one or more internal ribosome entry sites (IRES), one or more transposon sequences, one or more site-specific recombination site sequences, one or more restriction enzyme sequences, one or more nucleotide sequences encoding a fusion partner protein or peptide (e.g., glutathione-S-transferase (GST), hexahistidine ($His_6$) or thioredoxin), one or more selectable markers or selection modules, one or more bacterial sequences useful for propagating the insertional mutagenic polynucleotide molecules in a host cell, one or more 5' gene traps, one or more screenable markers, STOPs in 3 frames, one or more 3' gene traps, one or more nucleotide sequences encoding localization signals such as nuclear localization signals or secretion signals, one or more nucleotide sequences encoding one or more transmembrane regions (e.g., one or more amino acids, and typically one or more hydrophobic amino acids, capable of anchoring a polypeptide into a cellular membrane), one or more origins of replication, one or more protease cleavage sites, one or more desired proteins or peptides encoded by a gene or a portion of a gene, one or more sequences encoding one or more 5' or 3' polynucleotide tails (particularly a poly (A) tail), and the like. As the ordinarily skilled artisan will readily understand, the insertional mutagens of the invention can comprise one or more of these or other nucleotide sequences, in any order and combination, and can comprise more than one of a given nucleotide sequence.

In certain embodiments, the insertional mutagens comprise one or more nucleotide sequences capable of mutating an open reading frame (ORF). For example, the insertional mutagen can contain a number of nucleotides that is not divisible by 3, and which, therefore, would result in a frameshift upon insertion of the polynucleotide into an ORF.

In another embodiment, the insertional mutagen comprises one or more primer recognition sites, thereby facilitating the detection of the mutated gene using primer-based amplification or sequencing methods such as PCR.

In certain other embodiments of the invention, the insertional mutagens can additionally or alternatively comprise one or more stop codons. Stop codons are useful for terminating translation of genes, thereby facilitating mutation of a functional protein. The stop codons can be located on one or both strands of a double stranded insertional mutagen and can be nested to terminate translation in all three reading frames.

In certain other embodiments of the invention, the insertional mutagens can additionally or alternatively comprise one or more mRNA destabilizing elements. Upon integration into a gene and incorporation into an mRNA produced by the gene, the RNA instability element will decrease the amount of mRNA from the gene. A number of mRNA instability elements are known in the art and useful in the present invention (see, for example, Shaw et al., *Cell* 46:659-667 (1986); Ishida et al., *Nucleic Acids Research* 27: e35 (1999) each incorporated herein by reference for teaching RNA instability elements and methods of using such elements).

In certain other embodiments of the invention, the insertional mutagens can additionally or alternatively comprise one or more selectable markers. A selectable marker is a gene that encodes an expression product that can be selected for or against. Examples of selectable markers include but are not limited to: (1) polynucleotide segments that encode products which provide resistance against otherwise toxic compounds (e.g., antibiotics or other drugs); (2) polynucleotide segments that encode products which are otherwise lacking in the recipient cell (e.g., tRNA genes, auxotrophic markers); (3) polynucleotide segments that encode products which suppress the activity of a gene product; (4) polynucleotide segments that encode products which can be readily identified (e.g., phenotypic markers such as β-galactosidase, green fluorescent protein (GFP), and cell surface proteins); (5) polynucleotide segments that bind products that are otherwise detrimental to cell survival and/or function; (6) polynucleotide segments that otherwise inhibit the activity of any of the polynucleotide segments described in (1)-(5) above (e.g., antisense oligonucleotides); (7) polynucleotide segments that bind products that modify a substrate (e.g., methylases and restriction endonucleases); (8) polynucleotide segments that can be used to isolate or identify a desired molecule (e.g. specific protein binding sites); (9) polynucleotide segments that encode one or more screenable markers; (10) polynucleotide segments, which when absent, directly or indirectly confer resistance or sensitivity of the cell to particular compounds; (11) polynucleotide segments that encode products which are toxic in recipient cells; (12) polynucleotide segments that inhibit replication, partition or heritability of nucleic acid molecules that contain them; and (13) polynucleotide segments that encode conditional replication functions, e.g., replication in certain hosts or host cell strains or under certain environmental conditions (e.g., temperature, nutritional conditions, etc.). In the present invention, selectable markers allow the detection of integration of the insertional mutagens into the host cell genome. In addition, selectable markers can be positioned on the insertional mutagens to allow selection for insertion events that occur in transcriptionally active or silent regions of the genome (see FIGS. 2-6 for non-limiting examples). The selectable marker can be expressed from a promoter on the insertional mutagen that is inserted or from a promoter located in the polynucleotide to be mutated (see FIG. 7 for non-limiting examples). Selectable markers suitable for use in accordance with this aspect of the invention include positive selectable markers and negative selectable markers.

A positive selectable marker allows cells expressing the selectable marker to survive selection, whereas cells not expressing the selectable marker die during selection. Examples of positive selectable markers include, but are not limited to, neomycin resistance gene (neo), puromycin resistance gene (puro), zeomycin resistance gene (zeo), hygromycin resistance gene (hyg), histidine D (his D), dihydroorotase, glutamine synthetase (gs), aspartate transcarbamylase, xanthine guanine phosphoribosyl transferase (gpt), carbamyl phosphate synthase (cad), multidrug resistance 1 (mdr1), thymidine kinase (tk), and hypoxanthine phosphoribosyl transferase (HPRT). Other suitable positive selectable markers are known in the art and will be familiar to the ordinarily skilled artisan. In accordance with the invention, the selectable marker can be expressed from a promoter on the insertional mutagen that is inserted, or from a promoter located in the DNA to be mutated. Accordingly, in the present invention, a positive selectable marker can be used, for example, to select for cells that have integrated the insertional mutagen (regardless of location in the genome) (FIG. 7, selection for SM) or for cells in which the insertion is into a transcriptionally active gene (for examples, see FIGS. 2-6).

A negative selectable marker causes cells expressing the selectable marker to die during selection, whereas those cells not expressing the selectable marker survive selection. Examples of negative selectable markers include but are not limited to HPRT, thymidine kinase, cholera toxin, pertussis toxin, tetanus toxin, and diphtheria toxin. Other negative selectable markers are known in the art and will be familiar to the ordinarily skilled artisan. The negative selectable marker used in accordance with the invention can be advantageously expressed from a promoter on the insertional mutagen, or from a promoter located in the DNA to be mutated. In the present invention, a negative selectable marker can be used, for example, to select against cells where insertion is into a transcriptionally active gene. The presence of a negative selectable marker in combination with site-specific recombination signals can also be used to select against cells that have failed to delete the sequences between the recombination signals (see, e.g., FIGS. 8C, 9A-9D and 9F for non-limiting examples of insertional mutagens useful in accordance with this embodiment of the invention).

In certain such embodiments, the insertional mutagen can contain one or more positive selectable markers and one or more negative selectable markers. In such embodiments in which the insertional mutagen contains both a positive and a negative selectable marker, the markers can be present as separate open reading frames or as a single fusion open reading frame (see FIG. 9F for a non-limiting example of such a polynucleotide). When the selectable markers are present in the polynucleotides as separate open reading frames, the positive selectable marker and negative selectable marker can be expressed as a single polycistronic transcript (see FIG. 9G for a non-limiting example of such a insertional mutagen) or as separate transcripts (see FIGS. 8C and 9A-9C for non-limiting examples of such insertional mutagens). The presence of both a positive selectable marker and a negative selectable marker in the same insertional mutagen can be used, for example, to select against actively expressed genes and for developmentally regulated genes, and vice versa. Alternatively, the presence of both a positive selectable marker and a negative selectable marker can be used to select for actively expressed genes that are down-regulated in response to developmental or environmental cues. Vectors and methods for trapping and selecting for developmentally regulated genes are well-known in the art (see, e.g., Gogos et al., *J. Virol.* 71:1644-1650 (1997); Wempe et al., *Genome Biol.* 2:

research 23.1-23.10 (2001); and Medico et al., *Nature Biotech.* 19:579-582 (2001); the disclosures of all of which are incorporated herein by reference in their entireties for these vectors and methods).

In certain other embodiments of the invention, the insertional mutagens can additionally or alternatively comprise one or more recombination sites, for example one or more site-specific recombination sites or signals (see FIGS. 8 and 9). These recombination sites are discrete segments on the nucleic acid molecules that are recognized and bound by certain recombination proteins during the initial stages of integration or recombination between two nucleic acid molecules that each comprise such a recombination site. As discussed in detail above, such site-specific recombination sites or signals are useful for deleting (or inverting) the inserted insertional mutagen or a portion thereof from the DNA into which the insertional mutagen as inserted. This is useful, for example, for reverting the cellular phenotype(s) caused by the inserted insertional mutagen, which can be useful for confirming that a particular change in cellular phenotype is caused by a mutation induced by the insertion of the insertional mutagen. This approach is also useful for removing certain sequences from the inserted insertional mutagens, such as selectable markers, while leaving other sequences in the insertional mutagen, such as sequences that disrupt one or more genes in the DNA in which the insertional mutagen has inserted. Any site-specific recombination system can be used that is capable of deleting or inverting an inserted insertional mutagen. Examples of useful recombination signals include loxP, FRT, and att which are useful in conjunction with Cre, FLP (or FLPe) and PhiC31 recombinases, respectively (see, e.g., Hoess and Abremski, in: *Nucleic Acids and Molecular Biology*, vol. 4. Eds.: Eckstein and Lilley, Berlin-Heidelberg: Springer-Verlag; pp. 90-109 (1990), Broach, et al., *Cell* 29:227-234 (1982); Ishida et al., *Nucl. Acids Res.* 27:e35 (1999); O'Gorman et al., *Science* 251:1351-1355 (1991); Bergemann et al., *Nucl. Acids Res.* 23:4451-4456 (1995); Sauer, B., *Curr. Opin. Biotech.* 5:521-527 (1994); Schwenk et al., *Nucleic Acids Res.* Jun. 1, 2002; 30(11):2299-306; Schaft et al.; *Genesis.* September 2001; 31(1):6-10; Farley et al.; *Genesis*, November-December 2000; 28(3-4):106-10; Rodriguez et al.; *Nat Genet.* June 2000; 25(2):139-40; Buchholz et al.; *Nat Biotechnol.* July 1998; 6(7):657-62; Olivares et al.; *Gene*. Oct. 31, 2001; 278(1-2):167-76; Lee L, Sadowski P D, *J Biol Chem*. Aug. 17, 2001; 276(33):31092-8; Kolb AF, *Anal Biochem*. Mar. 15, 2001; 290(2):260-71; Araki et al., *Nucleic Acids Res*. Feb. 15, 1997; 25(4):868-72; Albert et al., *Plant J.* April 1995; 7(4):649-59; Santoro et al., *Proc Natl Acad Sci USA* Apr. 2, 2002; 99(7):4185-90; Trinh et al., *J Immunol Methods*, Oct. 20, 2000; 244(1-2):185-93; Soukharev et al., *Nucleic Acids Res.* Sep. 15, 1999; 27(18):e21 and U.S. Pat. Nos. 4,959,317, 5,434,066, 5,888,732, 6,080,576 and 6,136,566; each incorporated herein by reference for teaching vectors and methods of site specific recombination in mammalian cells). Other examples of suitable recombination sites for use in the insertional mutagens of the present invention include the attB, attP, attL, and attR sequences which are recognized by the recombination protein β Int, and by the auxiliary proteins integration host factor (IHF), FIS and excisionase (Xis). See Landy, *Curr. Opin. Biotech.* 3:699-707 (1993); see also U.S. Pat. Nos. 5,888,732, 6,143,557, 6,171,969 and 6,277,608, each of which is incorporated by reference herein in its entirety. Additional examples of recombination systems include Hin, Gin, Pin, Cin, and VDJ recombination, all of which are well-known in the art and which will be familiar to the ordinarily skilled artisan. Other site-specific recombination systems known in the art would also be recognized as useful by the ordinarily skilled artisan, and therefore can be used in accordance with the methods and compositions of the present invention. The site specific recombination signals may be wildtype or mutant. Mutant signals can be used, for example, to control the reversibility of the recombination reaction (reference Araki et al., *Nucleic Acids Res*. Feb. 15, 1997; 25(4):868-72; Dale et al., *Plant J.* April 1995; 7(4):649-59; Trinh et al., *J Immunol Methods*, Oct. 20, 2000; 244(1-2):185-93; Soukharev et al. *Nucleic Acids Res*. Sep. 15, 1999; 27(18):e21 incorporated in its entirety). The site-specific recombinases used in accordance with this aspect of the invention may be wildtype, mutant, or fusion proteins. Examples of modified recombinases useful in this aspect of the invention include, but are not limited to, cell-permeable CRE and CRE-ER (Jo et al., *Nature Biotech*. 19:929-933 (2001); Vallier et al., *Proc. Natl. Acad. Sci. USA* 98:2467-2472 (2001); each of which is incorporated by reference herein in its entirety). The recombinases used in the invention can be delivered to cells by infection or transfection of an expression vector encoding the recombinase (Westerman et al., *Proc. Natl. Acad. Sci. USA* 93:8971-8976 (1996), which is incorporated by reference herein in its entirety), transfection of the protein (e.g., via electroporation; Ager et al., *Radiat. Res*. 128:150-156 (1991); Chung et al., *Radiat. Res*. 125:107-113 (1991); each of which is incorporated by reference herein in its entirety), or through the use of a cell-permeable recombinase (Jo et al., *Nature Biotech.* 19:929-933 (2001); Vallier et al., *Proc. Natl. Acad. Sci. USA* 98:2467-2472 (2001); each of which is incorporated by reference herein in its entirety). Alternatively, the recombinase gene may itself be present on the insertional mutagen. The site-specific recombinase gene and/or recombination site from any of these systems can be included on the insertional mutagens of the invention, or can be introduced into the host cell separately to achieve the desired recombination event.

Using insertional mutagens containing one or more recombination sites, mutated cells or organisms (e.g., cells or organisms containing one or more mutated genes) produced by the methods of the invention can optionally be analyzed to confirm that any change in phenotype observed in the mutated cell or organism is the result of at least one insertionally mutated gene. One such method involves the use of site-specific recombination to reverse the phenotypic change, typically by inducing a reversion of the mutation to the wildtype by deleting or inverting the inserted insertional mutagen. In one such embodiment, site-specific recombination signals recognized by specific recombinase enzymes (e.g., the att/Int system from bacteriophage β, the lox/Cre system from bacteriophage P1, and the frt/FLP system from the *Saccharomyces cerevisiae* 2μ circle plasmid) can be included on the insertional mutagen (see FIGS. 9A-9H for non-limiting examples of such insertional mutagens containing site-specific recombination signals). Generally, such recombination sites are positioned on the insertional mutagen to allow the entire insertional mutagen, or a portion of the insertional mutagen responsible for mutating the gene, to be removed from or inverted within the DNA into which the insertional mutagen has inserted by introducing the appropriate recombinase enzyme into the cell. Optionally, as discussed below, use of a negative selectable marker or a reporter gene can facilitate identification or isolation of cells in which the mutagenic portion of the insertional mutagen has been deleted or inverted, and any change in cellular phenotype as a result of such deletion or inversion can be assessed so as to determine the phenotypic effects of the insertional mutagenesis (e.g., reversal or alteration of the cellular phenotype that is obtained upon insertional mutagenesis indicates that at least one insertional mutation is likely responsible for the observed change in phenotype from the wildtype).

The invention can also be used to identify developmentally regulated genes. In one embodiment, the presence of both a positive selectable marker and a negative selectable marker in the same insertional mutagen can be used, for example, to select against actively expressed genes and for developmentally regulated genes. Alternatively, the presence of both a positive selectable marker and a negative selectable marker can be used to select for actively expressed genes that are down-regulated in response to developmental or environmental cues. Vectors and methods for trapping and selecting for developmentally regulated genes are well-known in the art (see, e.g., Gogos et al., *J. Virol.* 71:1644-1650 (1997); Wempe et al., *Genome Biol.* 2:research 23.1-23.10 (2001); and Medico et al., *Nature Biotech.* 19:579-582 (2001); the disclosures of all of which are incorporated herein by reference in their entireties for these vectors and methods). Other methods for identifying trapped developmentally regulated genes in accordance with the invention involve the use of insertional mutagens that function as gene trap vectors such as those depicted in FIGS. 9B, 9C and 9H. These will comprise, for example, at least two site-specific recombination signals (e.g., at least two lox sites (e.g., loxP), at least two att sites (e.g., attP, attB, attL and/or attR), at least two FRT sites, or the like), which flank the positive selectable marker (as in FIG. 9B), the negative selectable marker (as in FIG. 9C), or both the positive and negative selectable markers (as in FIGS. 9G and 9H).

In a first such embodiment, the insertional mutagens depicted in FIGS. 9B, 9H, 11, and 13, can be integrated using standard methods of introduction of nucleic acid molecules into host cells that are well-known in the art and that therefore will be familiar to the ordinarily skilled artisan. Once the insertional mutagen has been integrated, cells can be selected based on the positive selectable marker carried by the insertional mutagen (and therefore integrated into DNA in the host cell). Surviving clones will contain the insertional mutagen integrated into a transcriptionally active gene, since it is only in such cells that the positive selectable marker will also be expressed. Cells can then be treated to delete the positive selectable marker (FIG. 11) or invert the positive marker (FIG. 13 legend) and create an operable linkage between the trapped gene and the negative selectable marker. In certain such aspects of the invention, this result is obtained through a site-specific recombination reaction: cells are treated with a site-specific recombinase, the identity of which will depend upon the specific recombination site used in construction of the insertional mutagen (e.g., Cre recombinase is used with lox recombination sites; Int recombinase is used with att recombination sites; FLP recombinase is used with frt recombination sites; etc.). Such treatment results in recombination between opposing recombination sites (see, e.g., FIG. 9B), thereby deleting or inverting the positive selectable marker from (and operably linking the negative selectable marker and the trapped gene) the genome of the cell. Cells can then be cultured under new conditions and/or treated with selection agents, and cells can be selected for lack of expression of the negative selectable marker to identify cells in which transcription of the trapped gene has been reduced or eliminated (e.g., cells that survive the negative selection). This process is illustrated schematically in FIG. 11 and described in FIG. 13 legend.

In another such embodiment, the insertional mutagens depicted in FIGS. 9C and 9H can be integrated using standard methods of introduction of nucleic acid molecules into host cells that are well-known in the art and that therefore will be familiar to the ordinarily skilled artisan. Once the insertional mutagens have been integrated, cells can be selected based on the negative selectable marker carried by the insertional mutagen. Cells in which the insertional mutagen has integrated into (e.g., that have trapped) a transcriptionally active gene will die during selection since it is only in such cells that the negative selectable marker will also be expressed, whereas cells in which the insertional mutagen has integrated into a transcriptionally silent region of the genome will survive. Cells can then be treated to delete the negative selectable marker and create an operable linkage between the trapped gene and the positive selectable marker, for example using site-specific recombination as outlined above. Such treatment results in recombination between opposing recombination sites (see, e.g., FIG. 9C), thereby deleting (FIG. 12) or inverting (FIG. 13) the negative selectable marker such that the positive selectable marker becomes operably linked to the trapped gene. Cells can then be cultured under new conditions or treated with agents capable of inducing gene expression, and cells can be selected for expression of the positive selectable marker to identify cells in which transcription of the trapped gene is increased (e.g., cells that survive the positive selection). This process is illustrated schematically in FIGS. 12 and 13.

In certain other embodiments of the invention, the insertional mutagens can additionally or alternatively comprise one or more reporter genes, also known as screenable markers. A reporter gene is a gene that encodes an expression product that can be detected in the cell. In accordance with the invention, the reporter gene may be expressed from a promoter on the insertional mutagen, or from a promoter in the DNA into which the insertional mutagen is inserted. Detection of the reporter gene allows the artisan to screen for cells that are or are not expressing the reporter gene. In the present invention, reporter genes allow insertions to be detected. In addition, reporter genes can be positioned on the insertional mutagen to allow screening for insertion events that occur in transcriptionally active or silent regions of the genome (see FIGS. 2-6). Reporter genes suitable for use in accordance with the invention can be any gene that encodes an expression product for which an assay exists. Examples of such suitable reporter genes include, but are not limited to, enzymes, structural proteins, cell surface proteins, and fluorescent proteins. Specific reporter genes known in the art include β-lactamase, β-galactosidase, luciferase, chloramphenicol acetyl transferase, green fluorescent protein and its derivatives, yellow fluorescent protein and its derivatives, blue fluorescent protein and its derivatives, cyan fluorescent protein and its derivatives, and red fluorescent protein and its derivatives. Many other reporter genes are known in the art and would be recognized by the artisan as being useful in the present invention.

Assays for detecting reporter genes include, but are not limited to, enzyme activity assays, cell microfluorimetry or fluorescence-activated cell sorting (FACS®), magnetic bead cell sorting, ELISA, ELISA Spot, transcriptional reporter assays, and cellular phenotypic assays such as proliferation, transformation, morphology, and the like.

Reporter genes can be used optionally in place of or in addition to the site specific recombination sequences to identify developmentally regulated genes and to revert phenotypes.

In certain other embodiments of the invention, the insertional mutagens can additionally or alternatively comprise one or more selectable markers and one or more reporter genes. The one or more selectable markers and one or more reporter genes can be present as a fusion gene or as two discrete open reading frames. Any combination of selectable markers and reporter genes can be used, including those detailed above. An example of a useful selectable reporter gene fusion is β-geo, a fusion of the neomycin resistance gene and the β-galactosidase gene. Other fusion genes known in the art, and which therefore are familiar to the ordinarily skilled artisan, can also be used in the present invention.

In certain other embodiments of the invention, the insertional mutagens can additionally or alternatively comprise one or more splice acceptor sequences operably linked to a promoter or not having an operably-linked promoter. Upon introduction into the target DNA, the one or more splice acceptor sequences can become paired with one or more splice donor sequences in the target DNA, thereby directing splicing from the gene in the DNA to the inserted insertional mutagen. This splicing, in turn, facilitates mutation of a gene in the target DNA through the creation of a fusion mRNA molecule. Any sequence capable of functioning as a splice acceptor site can be used in accordance with this aspect of the present invention. The splice acceptor site can be naturally occurring or non-naturally occurring. Splice acceptor sites and methods for testing the splicing activity of candidate or putative splice acceptors are known in the art, and therefore will be familiar to the ordinarily skilled artisan. In human cells, splice acceptor sites have a characteristic sequence represented as: YYYYYYYYYYNYAG, wherein Y denotes any pyrimidine and N denotes any nucleotide (see *Nucleic Acids Research* 19:3715-3799 (1991)).

In other embodiments of the invention, the insertional mutagens can additionally or alternatively comprise one or more splice donor sequences. Upon introduction into the target DNA, the one or more splice donor sequences can become paired with one or more splice acceptor sequences in the target DNA, thereby directing splicing from the polynucleotide to a gene in the target DNA. This splicing, in turn, facilitates mutation of the gene through the creation of a fusion mRNA molecule. The splice donor site may optionally be paired with a splice acceptor site on the insertional mutagen. Typically, in such a configuration, the order of these elements will be the splice acceptor followed by the splice donor (see FIGS. 1H-1J, 2D and 2H for non-limiting examples). The splice donor site may optionally be operably linked to a promoter on the insertional mutagen to produce a promoter-splice donor 3' gene trap (see FIGS. 5B-5E for non-limiting examples of such vectors). Any sequence capable of functioning as a splice donor site can be used. The splice donor site can be naturally occurring or non-naturally occurring. Splice donor sites and methods for testing splicing activity of candidate or putative splice donor sites are known in the art, and therefore will be familiar to the ordinarily skilled artisan. In human cells, splice acceptor sites have a characteristic consensus sequence represented as: (A/C)AG GURAGU, wherein R denotes a purine nucleotide (see *Nucleic Acids Research* 19:3715-3798 (1991)). The insertional mutagen may contain one or more exon sequences. These can be naturally, occurring or non-naturally made, as by recombinant DNA or synthetic methods. The exons may be derived from eukaryotic genes. Further, the one or more exons can be in tandem.

In other embodiments, the insertional mutagens can additionally or alternatively comprise one or more sequences that direct the addition of 5' or 3' polynucleotide tails on mRNA molecules transcribed from the DNA into which the insertional mutagen integrates. Such sequence can encode any polynucleotide tail, such as poly (A) tails, poly (G) tails, poly (U) tails, poly (C) tails, poly (I) tails, and the like. In one embodiment, the insertional mutagen comprises one or more polyadenylation signals that direct the addition of poly (A) tails on mRNA molecules transcribed from the DNA into which the insertional mutagen integrates. Polyadenylation signals can be derived from naturally occurring or non-naturally occurring sequences. Examples of useful polyadenylation signals include, but are not limited to, those derived from SV40 genes, growth hormone genes (e.g., bovine growth hormone), β-globin genes, actin genes, serum albumin genes, and retrovirus genes. Other polyadenylation signals are known in the art and will therefore be familiar to the ordinarily skilled artisan.

In certain other embodiments of the invention, the insertional mutagens can additionally or alternatively comprise one or more internal ribosomal entry sites (IRES). The IRES allows translation of internal open reading frames and are useful for expressing open reading frames located on the insertional mutagens upon integration into transcriptionally active genes. In certain embodiments, the ORF on the insertional mutagen is a selectable marker and/or reporter gene. Any IRES can be used to express an ORF located on the insertional mutagen. Examples of useful IRESs and methods of measuring IRES activity are known in the art (see, for example, Zhou et al., *PNAS* 98:1531-1536 (2001), Owens et al., *PNAS* 99:1471-1476 (2001); Venkatesan et al., *Mol Cell Biol.* 8: 2826-2837 (2001); Jackson et al., *Trends Biochem. Sci.* 15: 477-483 (1990); and Jang et al., *J. Virol.* 62:2636-2643 (1988); each incorporated herein by reference for teaching IRES sequences and methods for measuring IRES activity).

In certain other embodiments of the invention, the insertional mutagens can additionally or alternatively comprise one or more transposon signals. 1. Cui et al., *J Mol Biol.* May 17, 2002; 318(5):1221-35; 2. Izsvak et al., *J Biol Chem.* Jun. 24, 2002; 3. Dupuy et al., *Proc Natl Acad Sci USA*. Apr. 2, 2002; 99(7):4495-9; 4. Horie et al., *Proc Natl Acad Sci USA.* Jul. 31, 2001; 98(16):9191-6; 5. Dupuy et al., *Genesis*. June 2001; 30(2):82-8; 6. Fischer et al., *Proc Natl Acad Sci USA*. Jun. 5, 2001; 98(12):6759-64; 7. Ivics et al., *Cell*. Nov. 14, 1997; 91 (4):501-10. Other transposons also function in mammals: 8. Zagoraiou et al., *Proc Natl Acad Sci USA*. Sep. 25, 2001; 98(20):11474-8; 9. Sherman et al., *Nat Biotechnol.* November 1998; 16(11):1050-3; 10. Kawakami et al., *Proc Natl Acad Sci USA*. Oct. 10, 2000; 97(21):11403-8; 11. Fadool et al., *Proc Natl Acad Sci USA*. Apr. 28, 1998; 95(9): 5182-6; 12. Plasterk R H, *Cell*. Sep. 10, 1993; 74(5):781-6; 13: Kaufman et al., *Nucleic Acids Res*. Nov. 25, 1991; 19(22): 6336; 14. Rubin et al., *Nucleic Acids Res*. Sep. 24, 1983; 11(18):6341-51; 15. Spradling et al., *Science*. Oct. 22, 1982; 218(4570):341-7; Ac and Ds and other plant transposons transpose, integrate and are used as insertional mutagens in plants: 16. Grevelding et al, *Proc Natl Acad Sci USA*. Jul. 1, 1992; 89(13):6085-9; 17. Walbot V., *Curr Opin Plant Biol.* April 2000; 3(2):103-7; 18. Pereira et al, *Methods Mol Biol*. 1998; 82:329-38; 19. Cooley et al., *Mol Gen Genet.* Aug. 27, 1996; 252(1-2):184-94; 20. Bhatt et al, *Plant J.* June 1996; 9(6):935-45. P element transposon can integrate broadly throughout genomes: 21. Kassis et al., *Proc Natl Acad Sci USA*. Mar. 1, 1992; 89(5):1919-23; 22. Berg et al., *Genetics.* March 1991; 127(3):515-24; 23. Tower et al., *Genetics*. February 1993; 133(2):347-59; 24. Cooley et al., *Prog Nucleic Acid Res Mol Biol.* 1989; 36:99-109; 25. Cooley et al., *Science*. Mar. 4, 1988; 239(4844):1121-8; 26. Spradling et al., *Proc Natl Acad Sci USA*. Nov. 21, 1995; 92(24):10824-30.

Transposon signals allow the insertional mutagens to insert into the DNA by expressing or otherwise introducing transposase in the cell with the insertional mutagen. In a preferred embodiment, the insertional mutagen is first introduced into DNA in a cell, and subsequently transposed, or "hopped," in order to insertionally mutate one or more genes. This can be done in vitro, in vivo, and in situ. Methods for transposing vectors in situ are well known in the art (see, for example, Lucklow et al., *J Virol.* 67:4566-4579 (1993); Ivics et al., *Cell* 91:501-510 (1997); and Luo et al., *PNAS* 95:10769-10773 (1998); each incorporated herein by reference for teaching vectors and methods of transposition thereof).

There are many transposon systems and transposon signals known in the art that are useful in the present invention. These include TY from yeast (e.g, TY1; see Devine and Boeke *Nucl. Acids Res.* 22:3765-3772 (1994), which is incorporated by reference herein in its entirety), P-elements, Hobo, Minos, and Manner from *Drosophila*, Tn5, Tn7, T0, Tn10, and Mu from bacteria, En/Spm from maize, and TCI/Mariner (and its derivatives, such as Sleeping Beauty) and Minos from mouse and *C. elegans*. Many other transposon systems are known in the art and would be recognized by the artisan as useful in the present invention. In addition, modified transposon signals and mutant transposases with enhanced efficiency have been described and would be useful in the present invention.

Any of the insertional mutagens described herein for insertion can be produced as viral vectors, such as retroviral vectors (including lentivirus), Herpes viruses vectors (such as Epstein-Barr virus, cytomegalovirus (CMV), Herpes zoster, and Herpes simplex), papillomavirus, picornavirus, papovavirus (such as polyoma vectors and SV40), adenovirus, adeno-associated virus, and hepatitis virus. Particularly preferred vectors are retroviral. Viruses have the advantage of efficiently introducing the insertional mutagens into a cell, and, in the case of some viruses, facilitating efficient delivery of the insertional mutagen to the cell, and integration of the insertional mutagen into DNA in a cell.

Retroviral vectors of the invention and of use in the methods of the invention can contain retroviral LTRs, packaging signals, and any other sequences that facilitate creation of infectious retroviral vectors. Retroviral LTRs and packaging signals allow the insertional mutagens of the invention to be packaged into infectious particles and delivered to the cell by viral infection. Methods for making recombinant retroviral vectors are well known in the art (see for example, Brenner et al., *PNAS* 86:5517-5512 (1989); Xiong et al., *Developmental Dynamics* 212:181-197 (1998) and references therein; each incorporated herein by reference). In preferred embodiments, the retroviral vectors used in the invention are reverse orientation vectors, meaning that the gene mutation element in the insertional mutagen is in the opposite direction of viral transcription. The retroviral vectors can also be Self Inactivating viruses (SIN viruses). SIN viruses are not transcriptionally active upon insertion. Methods for making SIN viruses are known in the art (see for example, Hawley et al., *PNAS* 84:2406-2410 (1987); Brenner et al., *PNAS* 86:5517-5512 (1989); and Lih et al., *Gene* 164:289-294 (1995); each incorporated herein by reference for teaching vectors). Retroviral LTRs and packaging signals can be selected according to the intended host cell to be infected. Examples of retroviral sequences useful in the present invention include those derived from Murine Moloney Leukemia Virus (MMLV), Avian Leukemia Virus (ALV), Avian Sarcoma Leukosis Virus (ASLV), Feline Leukemia Virus (FLV), and Human Immunodeficiency Virus (HIV). Other viruses known in the art are also useful in the present invention and therefore will be familiar to the ordinarily skilled artisan.

In certain other embodiments, the insertional mutagens can additionally or alternatively comprise one or more bacterial sequences useful for propagating the insertional mutagens in prokaryotic or eukaryotic cells. Thus, the insertional mutagens of the invention can contain, for example, one or more antibiotic resistance markers, and/or one or more other art known sequences useful for propagating and analyzing the insertional mutagens.

Any of the insertional mutagens described herein can further or alternatively comprise one or more 3' gene traps. A number of 3' gene traps have been described and are useful in the present invention (see e.g., Harrington et al., WO 99/15650; Zambrowicz et al., U.S. Pat. No. 6,080,576; Sands et al., U.S. Pat. No. 6,136,566; Niwa et al, *J. Biochem.* 113: 343-349 (1993); Yoshida et al., *Transgenic Research* 4:277-287 (1995); all incorporated herein by reference in its entirety for teaching 3' gene traps). The 3' gene trap can be used to recover exons in the target DNA that are downstream of the insertional mutagen insertion site. Optionally, it can also be used to activate RNA or protein expression from genes in the target DNA. When a 3' gene trap is contained in a insertional mutagen of the present invention, it can be located upstream or downstream of a mutagenic portion of the insertional mutagen. In preferred embodiments, the 3' gene trap is located 3' of the mutagenic portion of the insertional mutagen.

In one specific embodiment, the insertional mutagen comprises a splice acceptor sequence that does not contain an operably-linked promoter 5' to the splice acceptor. This polynucleotide can serve as an essential 5' gene trap. In certain other specific embodiments, the insertional mutagen is found on a retroviral vector. The retrovirus can be infectious or non-infectious but in a preferred embodiment the retrovirus vector can form infectious retrovirus particles. In another specific embodiment, the insertional mutagen contains sequences required for transposition and accordingly forms a transposable element. In a further specific embodiment, the insertional mutagen comprises a polynucleotide having a splice acceptor with no operably-linked promoter, the splice acceptor having an optimal branch point, the mutagen also containing three stop codons in all three reading frames, an IRES that includes an exonic splicing enhancer, the mutagen further comprising a selectable marker with a polyadenylation site operably-linked, and a 3' gene trap component. The 3' gene trap component can optionally be constructed as described herein and as generally known in the art. Gene traps are also discussed in U.S. Pat. No. 6,410,266, incorporated herein by reference for disclosing 3' gene traps. In another embodiment, the insertional mutagen contains a splice acceptor without an operably-linked promoter 5', the splice acceptor containing an optimal branch point, the vector further containing three stop codons in all three reading frames, an IRES that does not contain the enhancer, a selectable marker with an operably-linked polyadenylation site, and wherein the vector does not contain the 3' gene trap.

Integration of the Insertional Mutagens

The insertional mutagens of the invention can be introduced into a cell and integrated into DNA by any method known in the art. In a preferred embodiment, they are introduced by transfection. Methods of transfection include, but are not limited to, electroporation, particle bombardment, calcium phosphate precipitation, lipid-mediated transfection (e.g., using cationic lipids), micro-injection, DEAE-mediated transfection, polybrene mediated transfection, naked DNA uptake, and receptor mediated endocytosis.

In another preferred embodiment, the insertional mutagens are introduced by viral transduction or infection. Suitable viral vectors useful in the present invention include, but are not limited to, adeno-associated virus, adenovirus vectors, alpha-herpesvirus vectors, pseudorabies virus vectors, herpes simplex virus vectors and retroviral vectors (including lentiviral vectors). Methods for making and using viral vectors are described above and elsewhere herein, and are well-known in the art and therefore familiar to the ordinarily skilled artisan (see, for example, Viral Vectors: Gene Therapy and Neuroscience Applications E. Caplitt and Loewy, Academic Press, San Diego (1995); incorporated herein by reference for teaching viral vectors and methods of using such vectors for introducing and expressing polynucleotides of interest).

In a preferred such embodiment, the vectors are retroviral vectors (including lentiviral vectors) and are introduced into the cell by infection. Vectors containing viral LTRs and packaging signals are described above. Methods for packaging retroviral vectors are also known in the art and can be used in the present invention (see, for example, U.S. Pat. No. 5,449,614, the disclosure of which is incorporated herein by reference in its entirety for teaching vectors, packaging cell lines, and methods of making and packaging viral vectors).

Following introduction into a cell by transfection or infection, the insertional mutagens of the invention integrate into the genome of the cell. The insertional mutagen can integrate into the target DNA by any method including, but not limited to, non-homologous recombination including retroviral insertion and transposition, site-specific recombination, homologous recombination and the like. In certain preferred embodiments, the insertional mutagen integrates by non-homologous recombination (e.g., integration by DNA end-joining, retroviral insertion, or transposition).

In certain preferred embodiments of the invention, the cell can be treated with one or more DNA-breaking agents prior to, during, or following introduction of the insertional mutagen into the cell. DNA-breaking agents increase the efficiency of integration. Examples of DNA-breaking agents suitable for use in accordance with this aspect of the invention include, but are not limited to, □γ-radiation, X-ray irradiation, UV irradiation, bleomycin, peroxides, and restriction enzymes. Other agents known to break DNA in living cells can also be used. Methods of using DNA breaking agents to enhance insertional mutagen insertion have been described (see, e.g., Harrington et al., WO 99/15650, incorporated herein by reference for teaching methods of enhancing non-homologous recombination).

In one embodiment, the initial integration is not the mutagenic event. Where the insertional mutagen contains a transposition signal, after the initial integration, the insertional mutagen can be induced to transpose ("hop") to a new location, where the mutagenic event can occur. Methods for transposing vectors in situ are well known in the art and therefore will be familiar to the ordinarily skilled artisan (see, for example, Ivics et al., Cell 91:501-510 (1997); and Luo et al., PNAS 95:10769-10773 (1998); each incorporated herein by reference for teaching transposition vectors and methods).

A variety of genes can be mutated using the methods of the invention. For example, known genes, including disease-causing genes (e.g., oncogenes, integrated viral genes (including HIV), genes causing genetic abnormalities such as cancers, multiple sclerosis, Alzheimer's disease, diabetes, muscular dystrophy, ALS, Gaucher's Disease, Tay-Sachs disease, hemophilia, β-thalassemia, cystic fibrosis, sickle cell trait, and the like) and normal genes (imparting any phenotype to a cell or organism) can also be mutated using the methods of the invention. In another embodiment, genes which have been previously unknown or incompletely characterized can be mutated using the methods of the invention. In another embodiment, genes can be mutated that are known or characterized but which were not known to be correlated to a desired phenotype produced by the mutagenesis methods of the invention. The invention thus provides a way to identify, isolate and characterize previously unknown or incompletely characterized genes in a variety of eukaryotic cells, and to examine the phenotypic importance of such genes by examining the effects on cellular phenotype when the genes are mutated.

It is also possible to introduce multiple (more than one per cell) insertional mutagens into each target cell to increase the probability that at least one gene will be mutated in the cell. Thus, cells created by the present methods can contain one or more integrated insertional mutagen. In certain embodiments, each of the target cells will contain 1-10 insertional mutagens, or 10 or more insertional mutagens. Introduction of two or more insertional mutagens into a single cell has the advantage of reducing the total number of cells that must be screened or selected to identify a cell with a mutation of a desired gene or of a gene(s) that causes a desired phenotype.

The number of insertional mutations that would be useful depends on the size of the genome of the host cell, its ploidy, gene structure, the average insertion window associated with gene mutation (e.g., size of the gene), the amount of genome coverage that is desired (e.g., the percentage of genes that are to be insertionally mutated), and the number of genes capable of producing a desired phenotype when mutated. In higher eukaryotic organisms, the genome is typically large. In mouse and human cells, for example, the haploid genome is estimated to be $3 \times 10^9$ base pairs (6 billion basepairs for the diploid genome). Therefore, $10^6$ insertions will result in an insertional mutagenic event frequency of 1 insertion per 3,000 base pairs. Assuming that an average human gene is approximately 25,000 base pairs, and assuming random insertion, $10^6$ insertions at a frequency of 1 in 3,000 base pairs will, on average, result in the mutation of one copy of each gene at least once. In practice, it can be necessary to create a larger number of insertions if integration is found not to be random. For example, it can be necessary to produce $10^7$ or more insertions to insertionally mutate the majority of genes at least once. It is also useful in certain situations or for certain applications to create fewer insertions. In preferred embodiments, an insertion library containing at least 10,000 insertions is created. In highly preferred embodiments, an insertion library containing at least 100,000 insertions is created.

Since genome sizes vary, it is possible to rely on general guidelines for determining the number of insertions necessary to create a library of a given complexity. As a general guideline it is useful to create 1 insertion per 1000 to 10,000 base pairs of the host cell genome. In one embodiment, 1 insertion is created per 30,000 base pairs of host cell genome. In highly preferred embodiments, the insertion frequency is adjusted to create at least one mutation per gene in the library. It should be understood that these are general guidelines and that other insertion frequencies are possible and recognized by those skilled in the art.

In embodiments where the insertional mutagen contains a selectable marker or reporter gene, cells can be selected or screened for integration by selecting or screening for expression of the marker or reporter. If the selectable marker is expressed from a promoter on the insertional mutagen (see, for example, FIG. 7), then any cell containing an integrated insertional mutagen should be recovered. If the selectable marker is not expressed from a promoter on the insertional mutagen, but is expressed from an upstream promoter on the target DNA (see FIGS. 2-6 for examples), then any cell containing the insertional mutagen integrated into a transcriptionally active gene can be selected for or against depending on whether a positive or negative selectable marker, respectively, is being used. Integration into transcriptionally active genes is desirable because in instances where the cells are going to be selected for a phenotype, mutation of a transcriptionally active gene is more likely to give a phenotype than mutation of a transcriptionally inactive gene. Alternatively, selection against a transcriptionally active gene can be useful for removing cells that have insertionally mutated a transcriptionally active gene so that other genes can be studied. For example, after removing cells containing mutated transcriptionally active genes, cells can be treated with agents that cause a change in gene expression within the cell and the artisan can now select for phenotypes that result from mutation of genes that were previously silent but became active. Reporter genes can also optionally be used to screen for integration into transcriptionally active or silent genes as above.

Library Screening or Selecting

Libraries of mutant cells can be screened or selected for mutation of a desired gene. Gene expression levels or gene product activity could be assayed or another phenotype that is associated specifically with the desired gene could be assayed. The assays can be used to identify cells with reduced or missing gene expression or function or with increased or restored gene expression or function. The tag is still useful in this embodiment. It can be used to verify that the mutation is in the desired gene or to ascertain if the desired gene is improperly expressed because of a mutation in a separate gene. The tag could also be useful as a way to isolate the mutated cell or clone of cells from a large number of cells when there is no assay that is sufficiently sensitive.

Examples of useful assays to detect a desired gene include, but are not limited to, ELISA, ELISA spot assays, PCR (e.g., rtPCR), transcription reporter assays, western blot, northern blots, Southern blots, electrophoretic mobility shift assays, transcriptional profiling (e.g., using gene chips), enzyme assays (e.g., protease, kinase, phosphatase, hydrolase, and other known assays), ligand binding assays, and Fluorescence Activated Cell Sorting (FACS®) and magnetic bead cell sorting.

Libraries of mutant cells produced by the present invention can also be screened or selected for desired phenotypes. Cells displaying the desired phenotype can then be used to identify one or more mutant genes responsible for the phenotype where the mutagenic polynucleotide comprises a tag that tags the mutated gene. This approach can be used, for example, to identify mutant genes that play a role in a cellular or biochemical process. By such methods of the invention, changes in a variety of cellular phenotypes that may be associated with genetic mutations may be analyzed, including without limitation: cell proliferation, cell transformation, cell migration, cell differentiation, signal transduction, cell morphology, cell transport, protein degradation, apoptosis, chemoresistance, chemosensitivity, inflammatory response, nuclear translocation of proteins, protein secretion, cellular activation, gene activation, protein expression, receptor activation, and metastasis. See also the previous list above. Many other assays are known in the art that the ordinarily skilled artisan would recognize as useful in the present invention.

The methods of the present invention can also be used in screens for the presence of conditional mutations in cells or organisms. Conditional mutations allow a mutation in a given gene to remain silent until a phenotypic screen (often dependent upon expression of the gene) is performed. This approach is particularly advantageous in situations where, for example, a mutation is toxic to the host cell, creates a slow-growth or no-growth phenotype, kills the cell, induces terminal differentiation, or is otherwise deleterious to the cell.

Examples of such conditional mutations that may be used in accordance with, or that may be detected by, the methods of the present invention include but are not limited to temperature sensitive mutations (heat- or cold-sensitive mutations), sensitivity to chemicals such as dimethylsulfoxide, site-specific recombination in vitro or in vivo, translation read-through, and the like.

Conditional mutations that produce phenotypes only after imposing specific experimentally controlled conditions can also be generated using the procedures described in this application. These conditional mutations can be useful in enabling more detailed investigation of gene function and access to a wider range of phenotypes that become possible as a consequence of the inherent ability to precisely control the timing and degree of function of conditionally mutant gene products. Examples of conditional mutations include the creation of cold or heat sensitive mutant cells or organisms that exhibit the loss of mutant gene function and the consequent appearance of mutant phenotypes only under conditions of depressed or elevated temperature, respectively (references 1-6), or the creation of chemically destabilized alleles that depend upon, for example, DMSO exposure, to uncover the altered function of the mutant alleles (reference 7).

The examples described above identify alleles that are conditional upon changes in the environment of the cell or organism. Other alleles that are conditional upon changes that are intrinsic to the mutated cell can also be identified. In this embodiment, experimentally controlled changes in the activity of components of the cell or organism would alter the function of conditionally mutant gene products, and this regulation of mutant gene function would serve to also regulate the appearance of the mutant phenotype. For example, Hsp90 and other chaperonin proteins have been shown to be required to maintain the active conformation of many marginally stable proteins including proteins that contain destabilizing sequence changes as a result of mutation (reference 8-11). Engineering cells to express Hsp90 only under the regulation of an inducible promoter (for example by using tetracycline, ecdysone, or other inducible promoter systems to control Hsp90 gene expression), or treating cells with chemicals that abbrogate Hsp90 function would generate cells in which many mutant proteins could be destabilized and their loss of function phenotypes revealed by experimentally controlled manipulation of Hsp90 activity (references 8-11). Thus the expression of mutant phenotypes would become dependent upon the experimentally induced reduction in Hsp90 or other chaperonin activity. Hsp90 activity might also be manipulated, for example, by creating cells that express their only Hsp90 protein as a fusion protein consisting of a steroid hormone binding (or other regulatory) domain fused to Hsp90 protein. Such a regulatory domain-chaperonin fusion protein would only exhibit chaperone active when bound with the appropriate steroid hormone (or other regulatory ligand; references 12-15) and conditional mutations and phenotypes would depend upon the concentration of the regulatory ligand in these cells. 1: Tasaka S E, Suzuki D T. *Genetics*. July 1973; 74(3):509-20; 2: Suzuki D T. *Science*. Nov. 13, 1970; 170 (959):695-706; 3: Suzuki D T, Piternick L K, Hayashi S, Tarasoff M, Baillie D, Erasmus U. *Proc Natl Acad Sci USA*. April 1967; 57(4):907-12; 4: Pringle J R. *Methods Cell Biol.* 1975; 12:233-72; 5: Basilico C. *Adv Cancer Res.* 1977; 24:223-66; 6: Meiss H K, Talavera A, Nishimoto T. *Somatic Cell Genet.* January 1978; 4(1):125-30; 7: Poloni D, Simanis V. *FEBS Lett*. Jan. 30, 2002; 511(1-3):85-9; 8 Morimoto R I, Kline M P, Bimston D N, Cotto J J. *Biochem.* 1997 32: 17-29; 9: Jakob U, Lilie H, Meyer I, Buchner J. *J Biol. Chem.* 1995 270:7288-94; 10: Rutherford S L, Lindquist S. *Nature*. Nov.

26, 1998; 396(6709):336-42; 11: Queitsch C, Sangster T A, Lindquist S. *Nature.* Jun. 6, 2002; 417(6889):618-24; 12: Angrand P O, Woodroofe C P, Buchholz F, Stewart A F. *Nucleic Acids Res.* Jul. 1, 1998; 26(13):3263-9; 13: Tada M, O'Reilly M A, Smith J C. *Development.* June 1997; 124(11): 2225-34; 14: Takebayashi H, Oida H, Fujisawa K, Yamaguchi M, Hikida T, Fukumoto M, Narumiya S, Kakizuka A. *Cancer Res.* Sep. 15, 1996; 56(18):4164-70; 15: Metzger D, Clifford J, Chiba H, Chambon P. *Proc Natl Acad Sci US A.* Jul. 18, 1995; 92(15):6991-5.

Uses of Mutated Cells

Once a cell with a desired phenotype is identified, the mutated gene can be identified via the tag present on its protein or mRNA or by analyzing the genomic integration site of the insertional mutagen, as discussed below. Methods for isolating the tagged gene include, but are not limited to, 5' RACE, inverse PCR, and cDNA library construction and hybridization. Methods for cloning genes that have been mutated or activated are known in the art (see for example, Harrington et al., U.S. patent application Ser. No. 09/276,820 filed Mar. 26, 1999; Zambrowicz et al., U.S. Pat. No. 6,080, 576; Sands et al., U.S. Pat. No. 6,136,566; Niwa et al., *J. Biochem.* 113:343-349 (1993); Yoshida et al., *Transgenic Research* 4:277-287 (1995); Baker et al., *Dev. Biol.* 185:201-214 (1997); each incorporated herein by reference for teaching methods of identifying genes mutated by the mutagenic polynucleotides).

The present invention can also be used to discover novel drugs and drug targets for use in diagnosing, treating or preventing a variety of diseases and physical disorders. For example, cDNA molecules and genomic fragments containing mutated genes of interest can be used to produce a gene product in vitro or in a cell or animal, to screen drugs, develop new diagnostic methods or assays related to the genotype or phenotype of interest, or to express proteins for therapeutic use (e.g., the gene may encode a protein such as erythropoietin, that can be administered to patients to treat a condition). The mutant gene or gene product also can be used to identify the corresponding wild-type gene or gene product. The wild-type gene can be used to produce a wild-type gene product in vitro or in a cell or animal, to screen drugs, to develop new diagnostic methods or assays related to the genotype or phenotype of interest, or to express proteins for therapeutic use (e.g., the gene may encode a protein such as erythropoietin that can be administered to patients to treat a condition).

Mutated cells made using the present invention can be used in drug screening. For example, mutated cells displaying a therapeutically relevant genotype or phenotype can be isolated from a library of mutated cells. Once isolated, the mutated cells can be exposed to test compounds to identify compounds that inhibit, further stimulate, or otherwise modulate the genotype or phenotype of interest. By carrying out this process, drugs and/or drug leads can be identified. Examples of phenotypes relevant to drug screening include, but are not limited to, apoptosis, cell proliferation, chemosensitivity, chemotherapeutic resistance, cell migration, cell activation (e.g., T cell activation), cell transformation, metastasis, cellular differentiation, signal transduction, transcriptional activation, protein expression, protein degradation, protein secretion, and other phenotypes known in the art that will be readily apparent to the ordinarily skilled artisan.

Mutated cells prepared according to the present invention can also be used for manufacturing or other commercial purposes. For example, cells of the invention displaying high growth rates, high protein expression levels, high levels of protein secretion, optimized post-translational modification of expressed proteins, ability to grow in serum-free or other defined or inexpensive culture media, etc., offer an advantage in commercial applications such as in manufacturing proteins, foods, beverages, therapeutics, etc.

Mutated cells prepared according to the methods of the present invention can also be used to study gene function in vivo. In one embodiment, cells mutated by the present invention are introduced into an animal by adoptive transfer. Cells displaying a desired phenotype in the animal can then be recovered and isolated. Alternatively, mutated cells that display a desired phenotype in culture can be introduced into an animal by adoptive transfer to study the in vivo phenotype of the cell. Examples of in vivo assays include, but are not limited to, tumor formation, metastasis, graft versus host disease, autoimmune disease, transplant rejection, reconstitution of missing or non-functional cell types (e.g., bone marrow transplantation), cell differentiation, and other assays known in the art. Methods for introducing cells into an animal by adoptive transfer are well known in the art (see, for example, Roth et al., *J Exp Biol.* 200:2057-2062 (1997); Mosier *Adv Immunol.* 50:303-325 (1991); Mule et al., *J. Immunother.* 12:196-198 (1992); each incorporated herein by reference for teaching methods and uses of adoptive transfer). Optionally, the mutated gene can be identified from the mutated cell.

In another embodiment, mutated cells (e.g., somatic or germ cells, embryonic stem cells or adult multipotential stem cells) can be used to create a transgenic animal. Methods for making transgenic animals from embryonic stem cells are well known in the art (see for example, Jackson and Abbott (2000) *Mouse Genetics and Transgenics*, Oxford University Press, pgs. 266-284; and Hogan, Beddington, Costantim, and Lacy (1994) *Manipulating the Mouse Embryo*, Cold Spring Harbor Press, all pages; Joyner, *Bioessays* 13:649-656 (1991); each reference incorporated herein by reference for teaching methods of producing transgenic animals from stem cells). Similarly, methods for making transgenic animals from somatic or germ cells are well known in the art (see, e.g., U.S. Pat. Nos. 5,322,775, 5,366,894, 5,476,995, 5,650,503 and 5,861,299, all of which are incorporated herein by reference in their entireties for teaching methods of producing transgenic animals from mutated or genetically manipulated somatic or germ cells). One such method is nuclear transfer cloning, in which the nucleus of a donor somatic cell is genetically modified (e.g., using the mutational methods of the present invention), and then the nucleus is removed from the donor cell and placed into a recipient cell (preferably, an oocyte) to produce a transgenic animal containing the genetic modifications from the donor nucleus. This process is well-known in the art and will be familiar to the ordinarily skilled artisan (see, e.g., Campbell et al., *Nature* 380:64-66 (1996); Cibelli et al., *Nature Biotech.* 16:620-621 (1998); McCreath et al., *Nature* 405:1066-1069 (2000); Hochedlinger et al., *Nature* 415:1035-1038 (2002); Schnieke et al., *Science* 278: 2130-2133 (1997); Kasinathan et al., *Nature Biotech.* 19:1176-1178 (2001); Wolf et al., *Arch. Med. Res.* 32:609-613 (2001); the disclosures of all of which are incorporated herein by reference in their entireties).

In one embodiment, transgenic animals that contain an insertional mutagen that is associated with a specific mutated gene can be prepared by, for example, insertionally mutating sperm cells in vivo and insertionally mutating oocytes in vitro or in vivo (e.g., one or more lentiviral vectors), and then fertilizing the mutated oocytes with the mutated sperm cells to produce a homozygous mutant zygote. This zygote can then be implanted into a recipient female and carried to term, thereby producing a transgenic animal homozygous for one or more mutations. Other methods for producing transgenic animals are well-known in the art, and will be familiar to the ordinarily skilled artisan (see, e.g., WO 90/05188; Hammer, R. E., et al., *J. Animal Sci.* 63:269-278 (1986); Pursel, V. G., et al., *J. Reprod. Fert. Suppl.* 40:235-245 (1995); Houdebine, L.-M., *J. Biotechnol.* 34:269-287 (1994); Hammer, R. E., et al., *Nature* 315:680-683 (1985); Mortensen, R. M., et al., *Mol. Cell. Biol.* 13:2391-2395 (1992); Deng, C., et al., *Cell* 82:675-684 (1995); and Murakami, T., et al., *Devel. Gen.* 10:393-401 (1989), the disclosures of all of which are incorporated herein by reference in their entireties).

Transgenic animals can be created in any eukaryotic organism. In preferred embodiments, the transgenic organism is a fly, a worm, a fish, or a mammal. In highly preferred embodiments, the organism is a human, a non-human primate, a mouse, a rat, a pig, a cow, a sheep, a dog, a cat, a bird, a zebrafish, *C. elegans*, or *Drosophila*. The transgenic animal can be used to carry out genetic screens for phenotypes of interest or for studying the function of individual genes. Examples of phenotypes include, but are not limited to, weight, height/length, organ histology, organ function, immune competency, blood chemistry (e.g., cholesterol levels, etc.), bone density and structure, gross morphology, and behavior. Additional phenotypic screens are known in the art and useful in the present invention (see for example Nolan et al., *Nature Genetics* 25:440-443 (2000); incorporated herein by reference for teaching phenotypic screens).

In another embodiment, multicellular organisms can be mutated directly by in vivo mutagenesis. An animal can be produced from a cell that is mutated in vitro. The cell can be a stem cell (embryonic or adult), somatic cell, or germ cell. The mutation that is introduced into the animal this way could be a heterozygous mutation in a gene where a homozygous mutation is necessary to produce a phenotype in an organism or in a cell in an organism. The organism can be mutagenized directly to produce the homozygous mutation. A gene responsible for the phenotype can be identified by a tag in the cell used to make the animal or in a cell insertionally mutagenized in the intact animal. The mutation that is introduced may be part of a set of mutations (i.e., mutation in two or more different genes) that are all required to produce a phenotype in an organism or in a cell in an organism. The organism can be mutagenized directly to produce the other required mutations.

Alternatively, transgenic plants can also be produced according to the methods of the present invention. In such methods, one or more, or suitably two or more, genes or alleles in a plant cell is mutated according to the methods of the invention. Transgenic plants may then be prepared using this mutated genomic DNA according to art-known plant genetic engineering techniques, such as nuclear transfer, transformation or protoplast fusion (see Hall, Robert D., *Plant Cell Culture Protocols*, Humana Press, New Jersey (1999); Gartland and Davey, *Agrobacterium Protocols*, Humana Press, New Jersey (1995); Kosuge et al., *Gen. Eng. of Plants* 26:5-25 (1983); Rogers et al., in: *Methods for Plant Molecular Biology*, A. Weissbach and H. Weissbach, eds., Academic Press, Inc., San Diego, Calif. (1988)). Such techniques are widely in use (see, e.g., Chaleff, R. S., *Genetics of Higher Plants: Applications of Cell Culture*, Cambridge: Cambridge University Press (1981)), and newly inserted foreign genes have been shown to be stably maintained during plant regeneration and are transmitted to progeny as typical Mendelian traits (Horsch et al., *Science* 223:496 (1984), and DeBlock et al., *EMBO* 3:1681 (1984)). These foreign genes retain their normal tissue specific and developmental expression patterns. The *Agrobacterium tumefaciens*-mediated transformation system has also proved to be efficient for transfer of genetic material, including many dicotyledonous plant species (Barton et al., *Cell* 32:1033(1983); Chang et al., *Planta* 5:551-558 (1994)) and monocotyledonous plants, e.g., in plants in the Liliaceae and Amaryllidaceae families (Hooykaas-Van Slogteren et al., *Nature* 311:763-764 (1984)) and in *Dioscorea bulbifera* (yam) (Schafer et al., *Nature* 327:529-532 (1987)).

It will be understood by one of ordinary skill in the relevant arts that other suitable modifications and adaptations to the methods, compositions and applications described herein are readily apparent from the description of the invention contained herein in view of information known to the ordinarily skilled artisan, and can be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE

Example 1

DKO vector construction and retrovirus production
1. Vector Design:

pDKO2 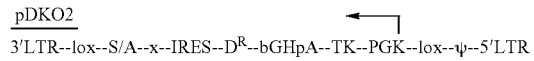
3'LTR--lox--S/A--x--IRES--$D^R$--bGHpA--TK--PGK--lox--$\psi$--5'LTR vector backbone: self-inactivating retroviral vector pSIR (Clontech)

S/A: branch site and splice acceptor from the intron of an immunoglobin gene heavy chain variable region; obtained by PCR from pCI vector (Promega)

x: stop codons in all 3 reading frames

IRES: wild type internal ribosomal entry site from EMCV; obtained by PCR from pE5LVP0 (ATCC#67525)

$D^R$: drug resistance gene for selection in the presence of neomycin, (pDKO vectors containing other selection markers, such as puromycin, hygromycin, zeocin. have been created in pDKO2 derivatives.)

bGHpA: bovine growth hormone polyA sequence; PCR from pcDNA3.1 (Invitrogen)

lox: lox71/lox66 sequences, cre recombinase recognition sites

TK: thymidine kinase

PGK: promoter $\psi$: retrovirus packaging signal

2. Function Tests:

This vector is designed to trap transcriptionally active genes using the function of the splice acceptor in the vector. When the vector is integrated into a gene, splicing can occur using endogenous splice donor at the end of exons and the splice acceptor provided by the vector. Once this splicing event occurs, a fusion transcript will be made resulting in a truncated protein of the trapped gene. IRES enables the expression of the drug selection marker when an active promoter is trapped, which allows selection of gene trap event.

IRES: We confirmed that the IRES does not have promoter activity, does function as an IRES TK: expression of TK causes cell death in gancyclovir containing media Cre/lox: transfection of cre expression plasmid into cells carrying above construct resulted in excision events occurring in ~80% of cells S/A--x--IRES--D$^R$--bGHpA: above construct was introduced into Jurkat cells. followed by drug selection (neomycin 1.5 mg/ml for Jurkat), drug resistant clones were harvested and assayed for the occurrence of gene trap event and gene trap efficiency by RT-PCR To confirm the ability of PDKO-2 to trap genes, RT-PCR was done using two nested gene specific primers (specific for DHFR, HPRT, FasR, and Casp8) paired with two nested vector specific primers. RT-PCR products were sequenced. All were confirmed to be true gene trap event with endogenous gene exon spliced onto the splice acceptor of pDKO2 vector

| | | | | Gene trap frequency: | | | |
|---|---|---|---|---|---|---|---|
| Cell type | # clones per pool | # pools total | # clones total | # of pools in which one of the following gene is trapped | | | |
| | | | | Hprt | DHFR | FasR | Casp8 |
| Jurkat | 7500 | 10 | 7.5 × 10$^4$ | 2 | 3 | 3 | 9 |

| Number of alleles and size of trapped genes: | | | | |
|---|---|---|---|---|
| Gene name | Hprt | DHFR | FasR | Casp8 |
| # hits | 2 | 3 | 3 | 9 |
| # alleles | 1 | 2 | 2 | 2 |
| gene size | 40 kb | 30 kb | 26 kb | 55 kb |

For 75,000 clones
(2+3+3+9)/(1+2+2+2)=2.4 hits per allele
for a diploid gene: 4.8 hits per 75,000 clones
number of clones needed to mutate one allele of each test gene once, on average=:1.56×10$^4$
average gene size considered here: (40+30+26+55)/4=38 kb
average human gene size 28 kb
number of clones needed to mutate one allele of each human gene once, on average=:2.×10$^4$ gene traps.
number of clones needed to mutate two alleles of each human gene in the same cell, on average =(2×10$^4$)$^2$=4× 10$^8$ gene traps 3. Retrovirus Production and Jurkat Infection:

pDKO2 vector was transfected in RetroPack PT67 cells (Clontech) via Exgen500 (MBI Fermentas). Individual stable colonies were picked and selected for high titer producers. High titer virus soup was harvested and used to infect Jurkat cells following spin-infection protocol. Briefly, 3×10$^6$ Jurkat cells were resuspended in 2 ml complete media plus 1 ml viral soup and polybrene at 8 ug/ml. We spininfected at 1000 g for 1 hour. Cells were then placed in 32C incubator overnight and then incubated at 37 C. for 24 hours to allow integration and expression of retrovirus. Titer was determined by limiting dilution and found to be 1-3×10$^4$ per ml.

What is claimed is:

1. A method for mutating both alleles of a gene in a cell by carrying out two independent insertional mutagenesis events in vitro, said method comprising inserting a first mutagen into one allele of said gene and independently inserting a second mutagen into the second allele of said gene, wherein both of said mutagens are inserted by non-homologous recombination.

2. A method for mutating a gene in a cell in vitro, said cell having a first mutagen inserted into one allele of said gene, said method comprising independently inserting a second mutagen into the second allele of said gene, wherein both of said mutagens are inserted by non-homologous recombination.

3. A method for mutating both alleles of a gene in a cell by carrying out two independent insertional mutagenesis events in vitro and identifying the mutated gene, said method comprising inserting a first mutagen into one allele of said gene and independently inserting a second mutagen into the second allele of said gene and identifying said gene by means of one or both of said mutagens, wherein both of said mutagens are inserted by non-homologous recombination.

4. A method for producing a cell in vitro with a homozygous mutation in a gene, said method comprising inserting a first mutagen comprising a selectable marker into one allele of said gene and independently inserting a second mutagen comprising a different selectable marker into the second allele of said gene, wherein both mutagens are inserted by non-homologous recombination.

5. A method for producing a cell with a homozygous mutation in a gene, the method comprising:
(1) inserting a mutagen comprising a selectable marker into one allele of a gene in a cell in vitro;
(2) selecting for said cell comprising the mutagen inserted into one allele of said gene by means of the selectable marker; and
(3) inserting a second mutagen comprising a different selectable marker into the second allele of said gene in the cell produced in (2);
thereby producing said cell with a homozygous mutation, wherein both of said mutagens are inserted by non-homologous recombination.

6. The method of claim 2, 3, or 4, wherein insertion of both mutagens is done sequentially.

7. The method of claim 2, 3, or 4, wherein insertion of both mutagens is done simultaneously.

8. The method of claim 2, 3, or 4, wherein said mutagens are identical.

9. The method of claim 2, 3, or 4, wherein said mutagens are not identical.

10. The method of claim 1 2, 3, 4 or 5, wherein said cell is a eukaryotic cell.

11. The method of claim 10, wherein said cell is a mammalian cell.

12. The method of claim 11, wherein said cell is a human cell.

13. The method of claim 11, wherein said cell is selected from the group consisting of rodent, rabbit, bovine, canine, feline, ovine and porcine.

14. The method of claim 1, 2, 3, or 4, wherein said mutagen comprises a marker gene.

15. The method of claim 14, wherein said mutagen further comprises a splice acceptor site operably linked to said marker gene.

16. The method of claim 3, wherein identifying said mutated gene comprises isolating and hybridizing DNA or RNA from said cell to a nucleic acid comprising a sequence from one or both of said mutagens.

17. The method of claim 1, 2, 3, or 4, wherein the first and second mutagens are introduced into the cell exogenously.

* * * * *

UNITED STATES PATENT AND TRADEMARK OFFICE
CERTIFICATE OF CORRECTION

PATENT NO. : 7,767,454 B2  Page 1 of 1
APPLICATION NO. : 10/288555
DATED : August 3, 2010
INVENTOR(S) : Harrington et al.

It is certified that error appears in the above-identified patent and that said Letters Patent is hereby corrected as shown below:

In the Claims

Column 62, line 35 - Claim 6 should read -- The method of claim 1, 2, 3, or 4... --.

Column 62, line 37 - Claim 7 should read -- The method of claim 1, 2, 3, or 4... --.

Column 62, line 39 - Claim 8 should read -- The method of claim 1, 2, 3, or 4... --.

Column 62, line 41 - Claim 9 should read -- The method of claim 1, 2, 3, or 4... --.

Signed and Sealed this

Thirtieth Day of November, 2010

David J. Kappos
*Director of the United States Patent and Trademark Office*